(12) United States Patent
Gordon et al.

(10) Patent No.: US 8,038,944 B1
(45) Date of Patent: Oct. 18, 2011

(54) ELECTROKINETIC DEVICE FOR CAPTURING ASSAYABLE AGENTS IN A DIELECTRIC FLUID

(76) Inventors: Julian Gordon, Lake Bluff, IL (US); Prasanthi Gandhi, Chicago, IL (US)

( * ) Notice: Subject to any disclaimer, the term of this patent is extended or adjusted under 35 U.S.C. 154(b) by 0 days.

(21) Appl. No.: 13/028,495

(22) Filed: Feb. 16, 2011

Related U.S. Application Data

(63) Continuation of application No. 12/955,150, filed on Nov. 30, 2010.

(51) Int. Cl.
*G01N 27/00* (2006.01)
(52) U.S. Cl. .................. 422/82.01; 435/7.1; 435/283.1; 435/287.1; 435/287.2; 435/288.3; 435/288.4; 436/518; 436/524; 436/525; 422/50
(58) Field of Classification Search .................. 422/50, 422/82.01; 435/7.1, 283.1, 287.1, 287.2, 435/288.3, 288.4; 436/518, 524, 525
See application file for complete search history.

(56) References Cited

U.S. PATENT DOCUMENTS

| 2,295,476 | A | 9/1942 | Ibison |
|---|---|---|---|
| 4,957,512 | A | 9/1990 | Denisov et al. |
| 6,548,311 | B1 * | 4/2003 | Knoll .............................. 436/524 |
| 7,341,841 | B2 * | 3/2008 | Metzger et al. ................ 435/7.2 |
| 7,767,150 | B1 | 8/2010 | Zaromb et al. |
| 2002/0137085 | A1 | 9/2002 | Herrick |
| 2007/0113685 | A1 | 5/2007 | Zaromb et al. |
| 2008/0220414 | A1 | 9/2008 | Jensen et al. |
| 2009/0274592 | A1 | 11/2009 | Bergeron |
| 2010/0000540 | A1 | 1/2010 | Pouteau et al. |
| 2010/0075317 | A1 | 3/2010 | Schneider et al. |
| 2010/0132561 | A1 | 6/2010 | Bromberg et al. |
| 2010/0186524 | A1 | 7/2010 | Ariessohn et al. |
| 2010/0261280 | A1 | 10/2010 | Black et al. |

OTHER PUBLICATIONS

An article entitled "Airborne Virus Capture and Inactivation by an Electrostatic Particle Collector" by Kettleson et al.; Environ. Sci. Technol., 2009, 43 (15), pp. 5940-5946. Retrieved from the internet: http://pubs.acs.org/doi/abs/10.1021/es803289w.
A Master's Thesis Entitled "Development of Electrostatic Sampling Systems for Monitoring Viable Bioaerosols" by Chi-Yu Chuang, presented Jan. 24, 2007. Retrieved from the internet: http://etdncku.lib.ncku.edu.tw/ETD-db/ETD-search/view_etd?URN=etd-0131107-131919.

* cited by examiner

*Primary Examiner* — Melanie J Yu
(74) *Attorney, Agent, or Firm* — Wood, Phillips, Katz, Clark & Mortimer

(57) ABSTRACT

Electrokinetic devices and methods are described with the purpose of collecting assayable agents from a dielectric fluid medium. Electrokinetic flow may be induced by the use of plasma generation at high voltage electrodes and consequent transport of charged particles in an electric voltage gradient. In one embodiment, the agents are directed electrokinetically to the sample collection assay device with no intermediate transfer steps. The agents are directed by creation of an electrokinetic potential well, which will effect their capture on to an assay device. Environmental agents such as biowarfare agents, pathogens, allergens or pollutants are collected autonomously on to the assay device, without any human intervention. The dielectric fluid medium, such as air, is sampled by electrokinetic propulsion with no moving parts or optionally, by transporting the dielectric fluid by a fan, pump or by breath. A further embodiment for collection of pathogen samples entails breathing into a tube where the sample is exposed to an electric plasma in the neighborhood of a high voltage electrode or electrodes, further transported by the breath through a potential well created at a sample collection device, where charge particles are electroprecipitated. The dielectric fluid medium may further include non-conductive liquids, such as oils. Oils may be sampled for the presence of contaminants, contaminating organisms or bio-degrading organisms.

17 Claims, 68 Drawing Sheets

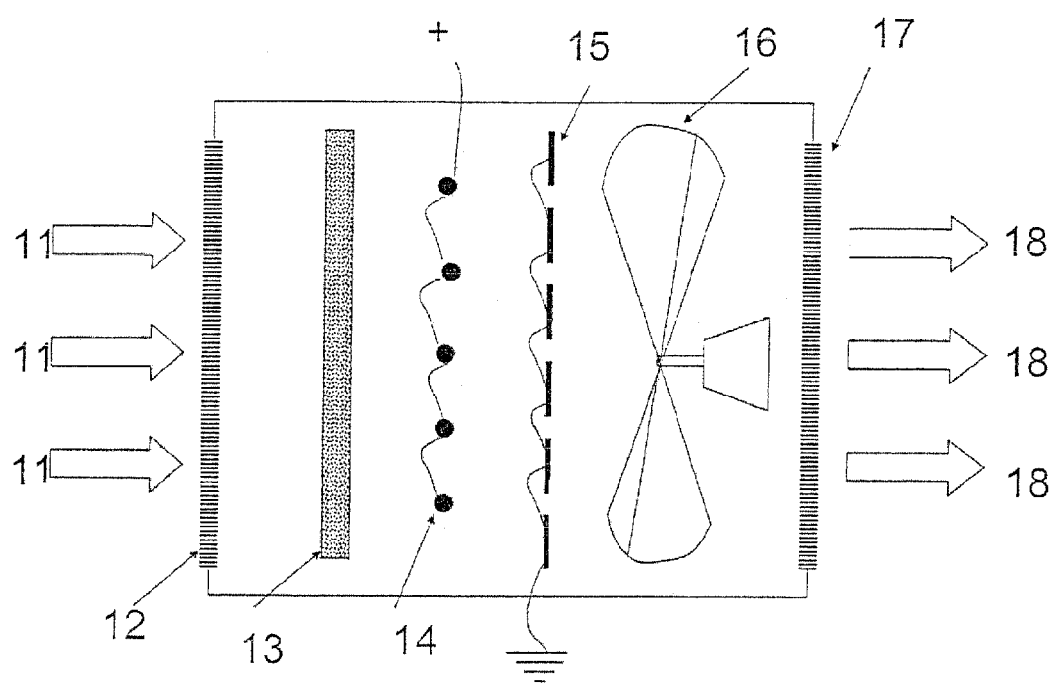

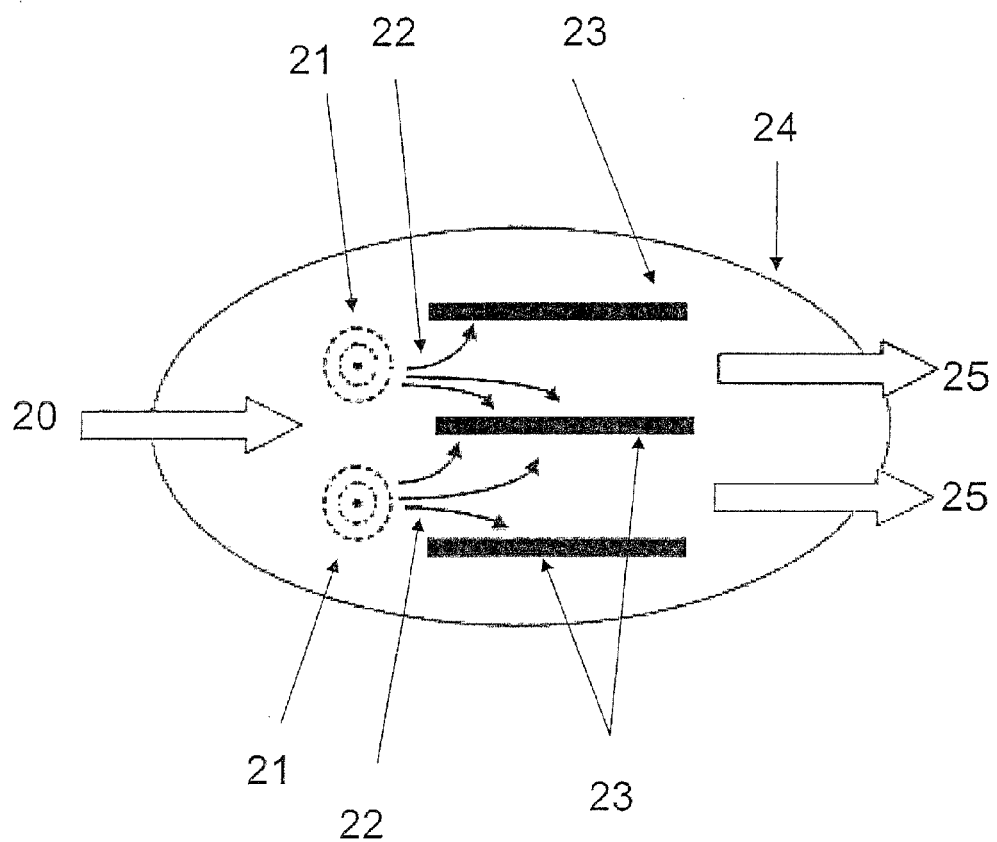

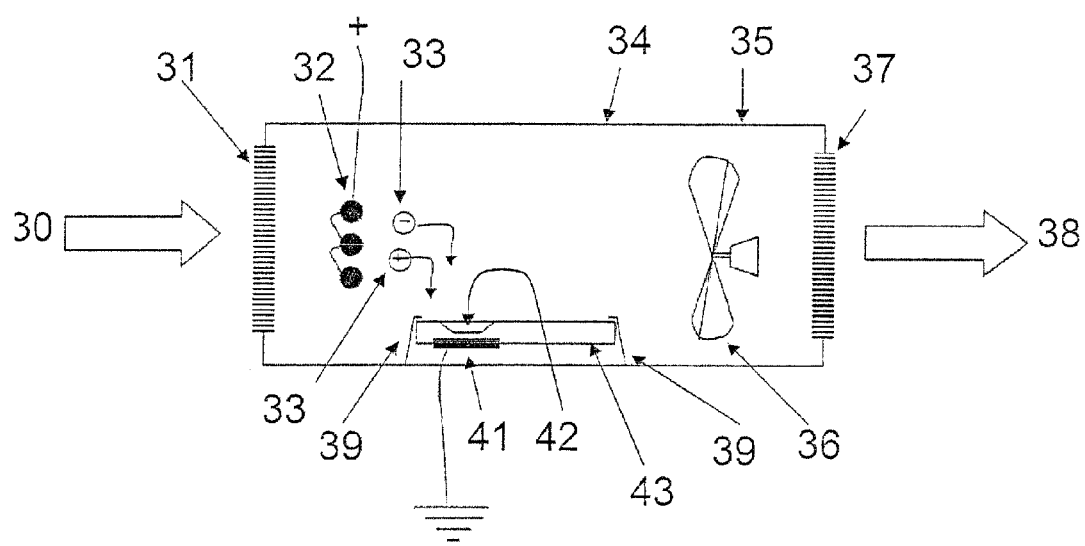
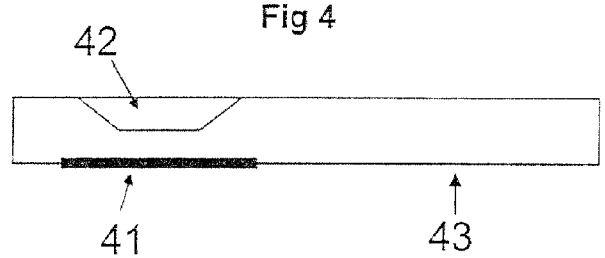
Fig 4

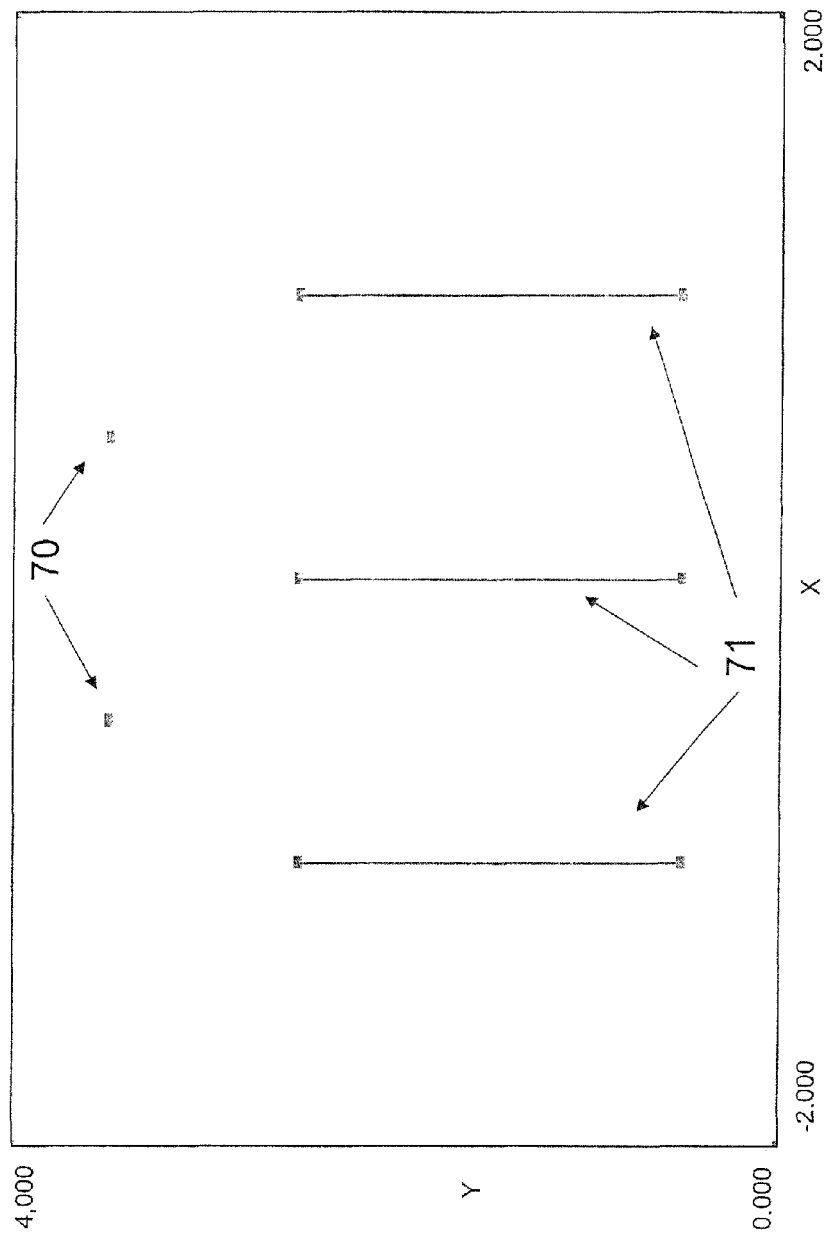

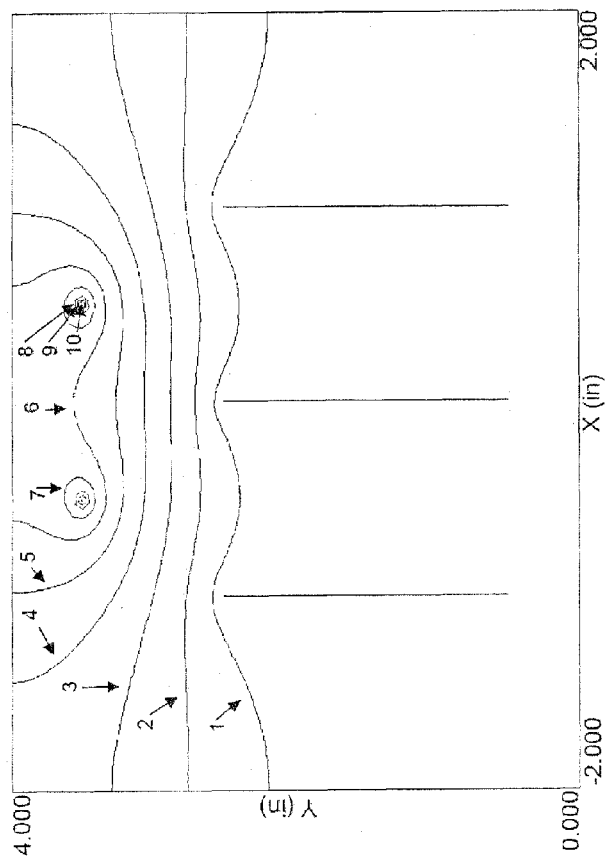

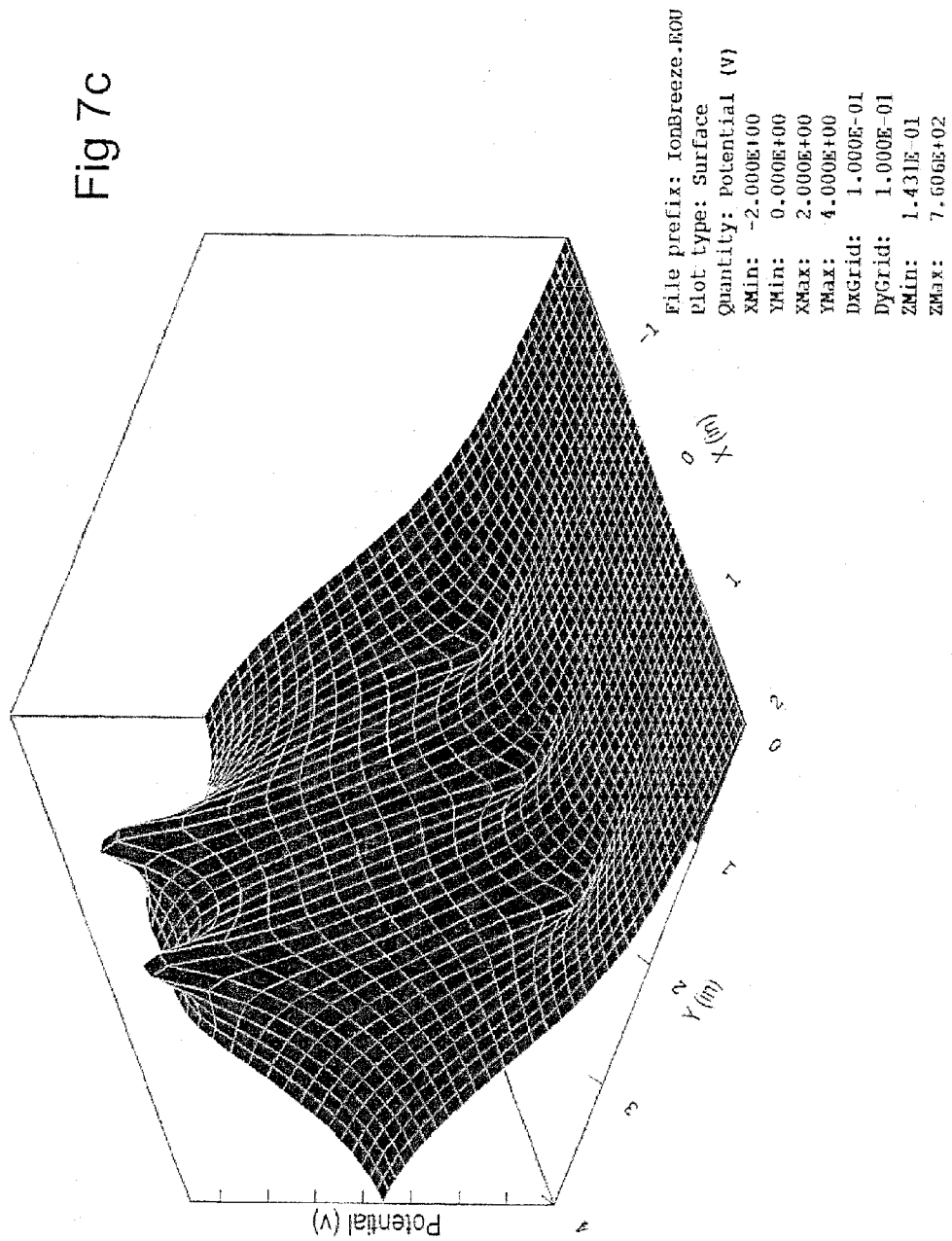

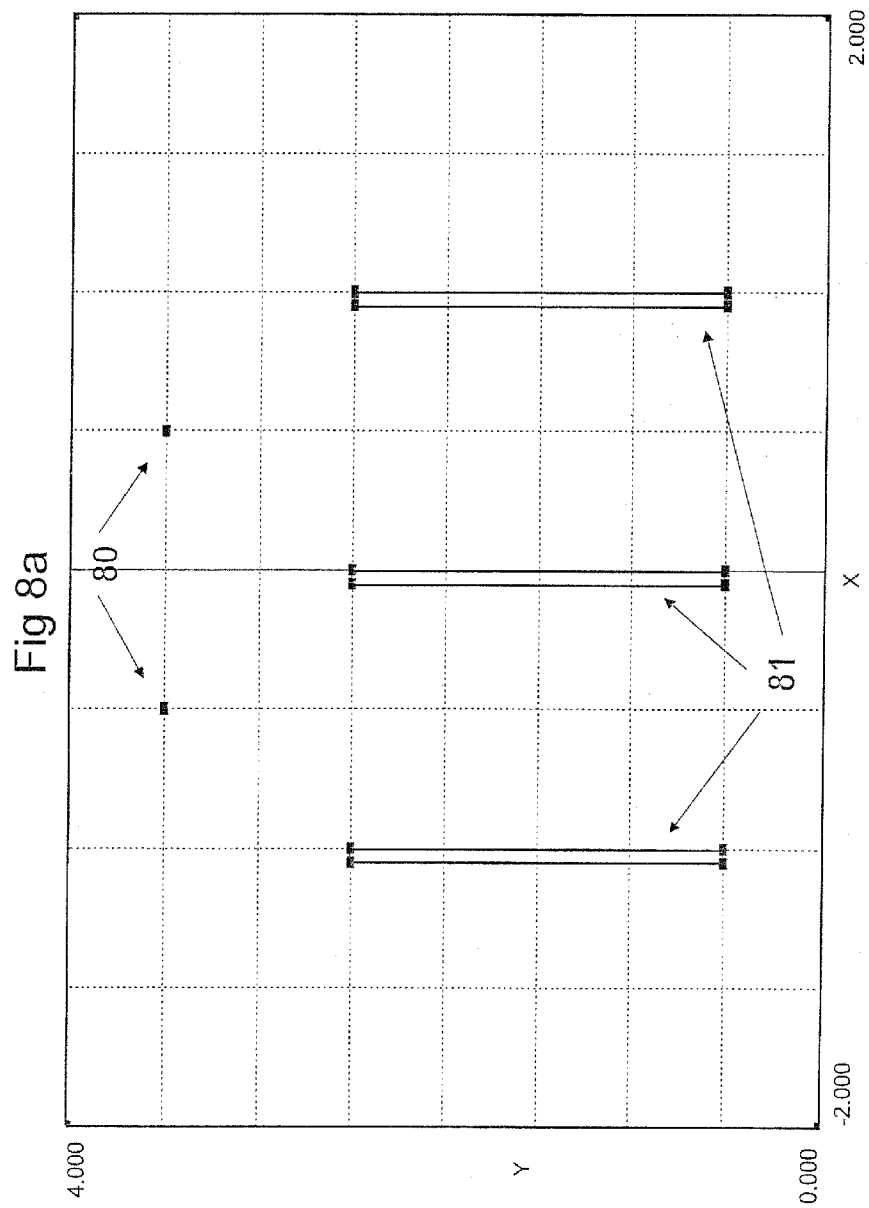

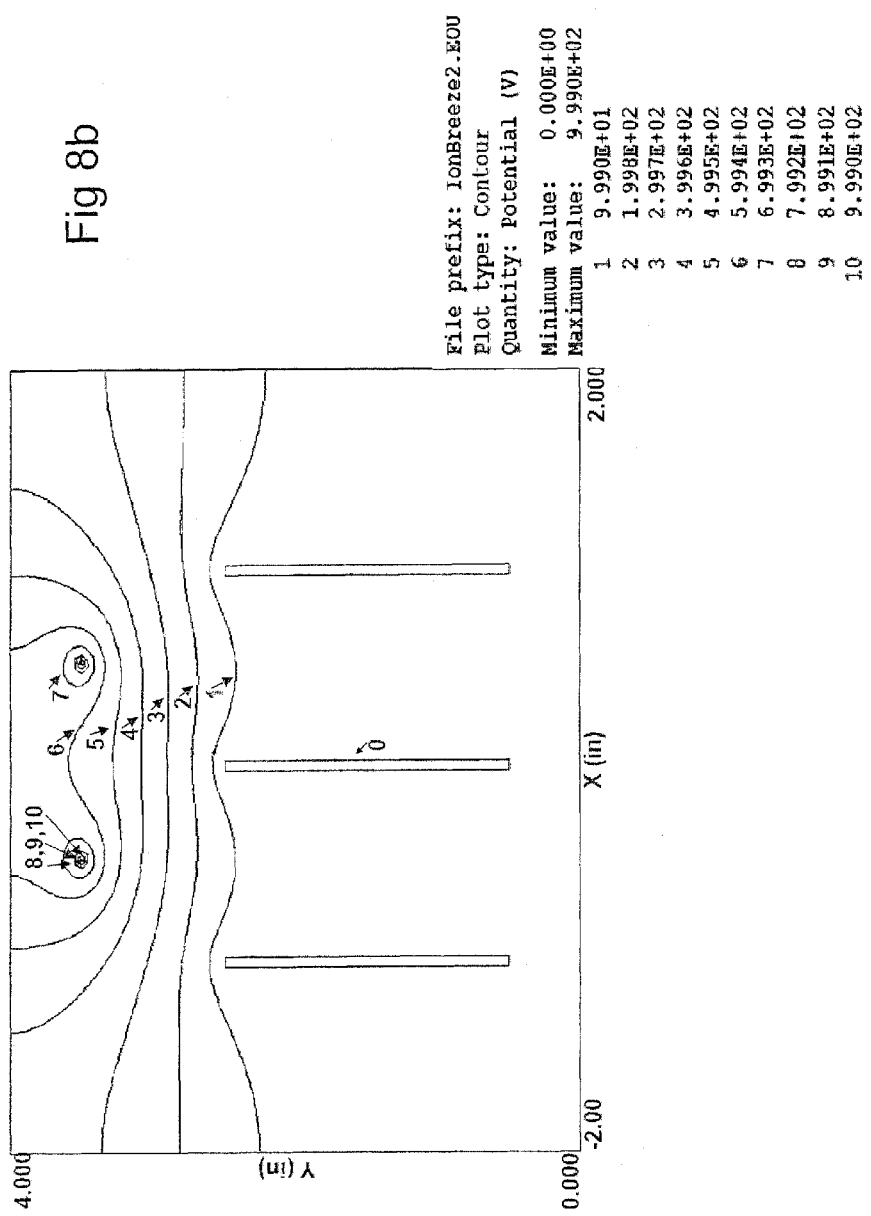

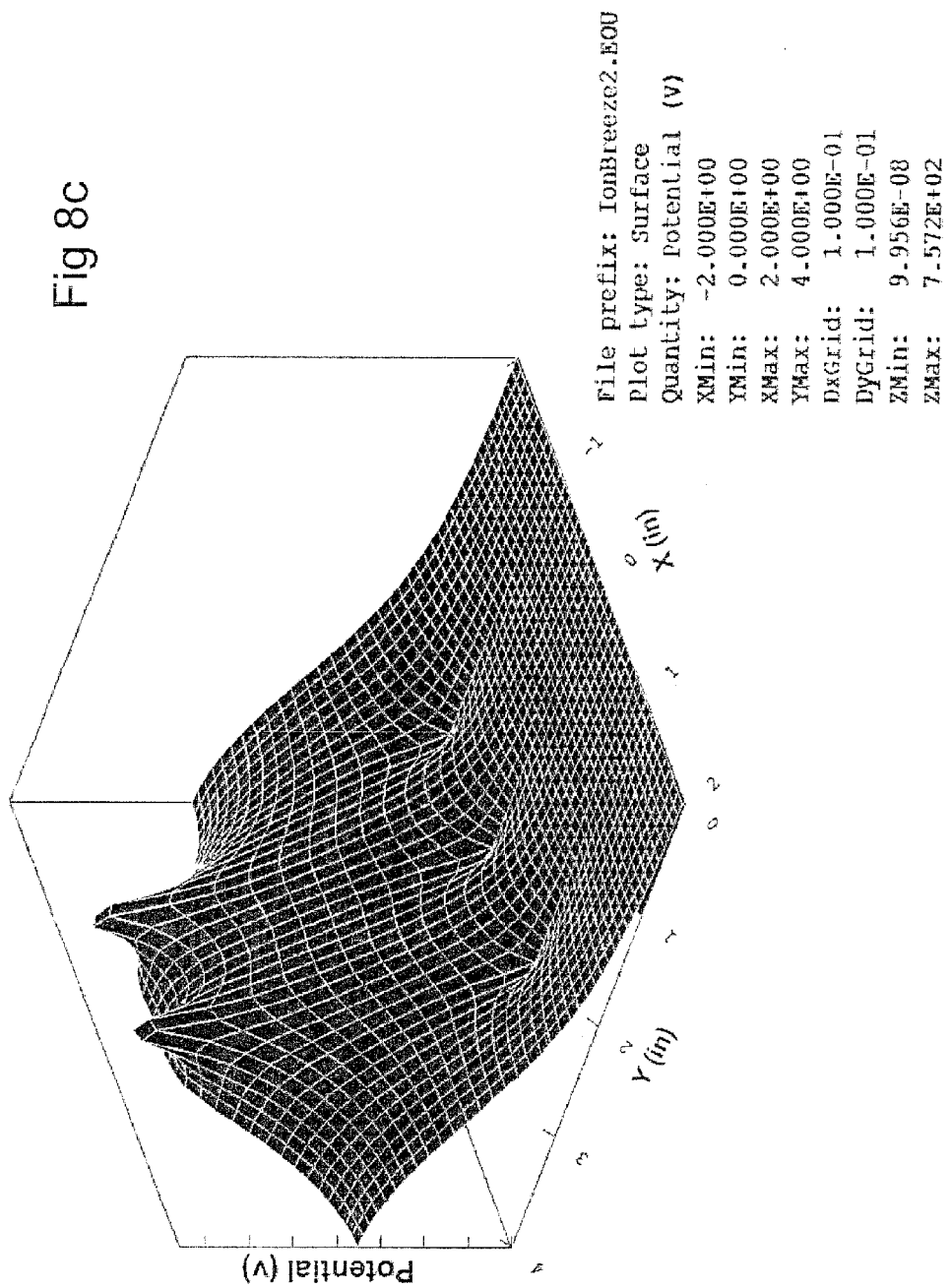

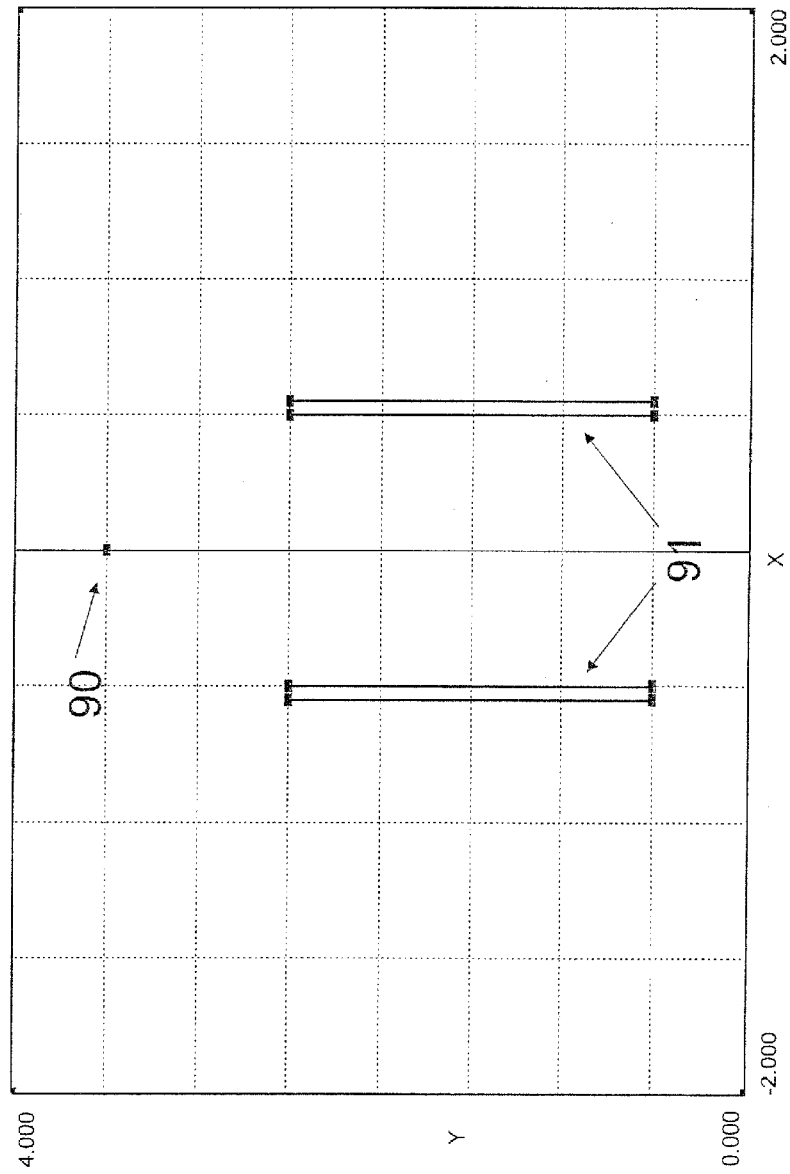

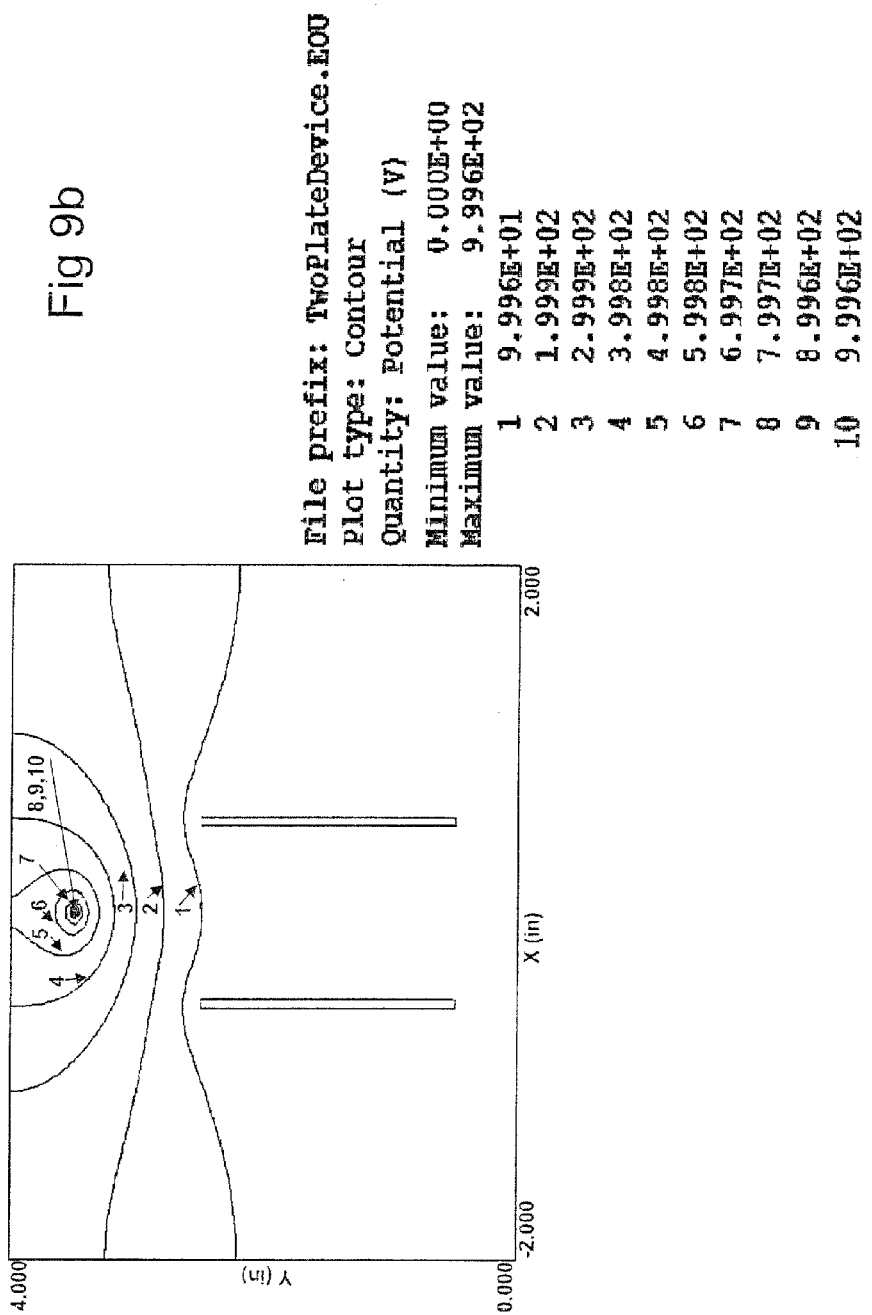

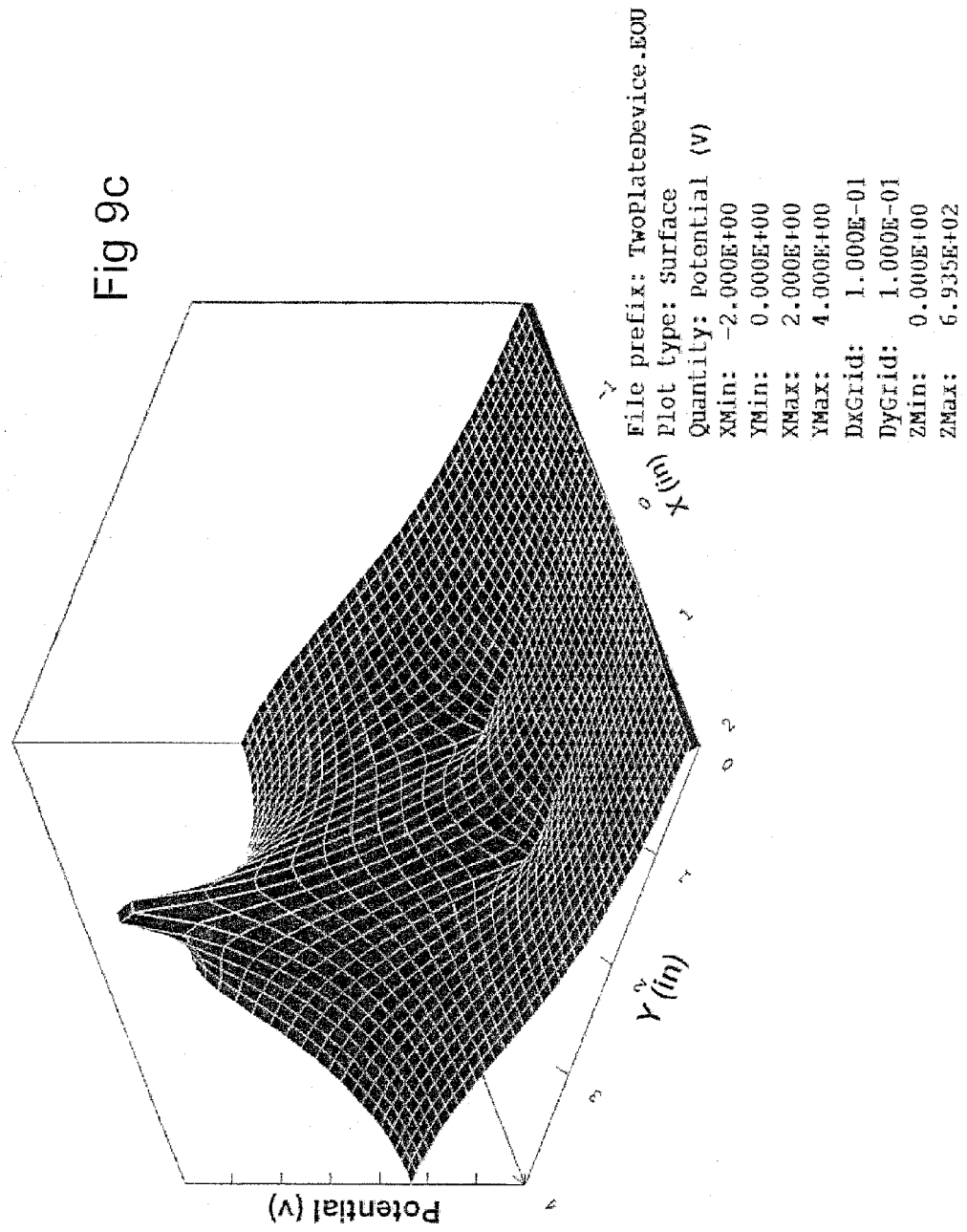

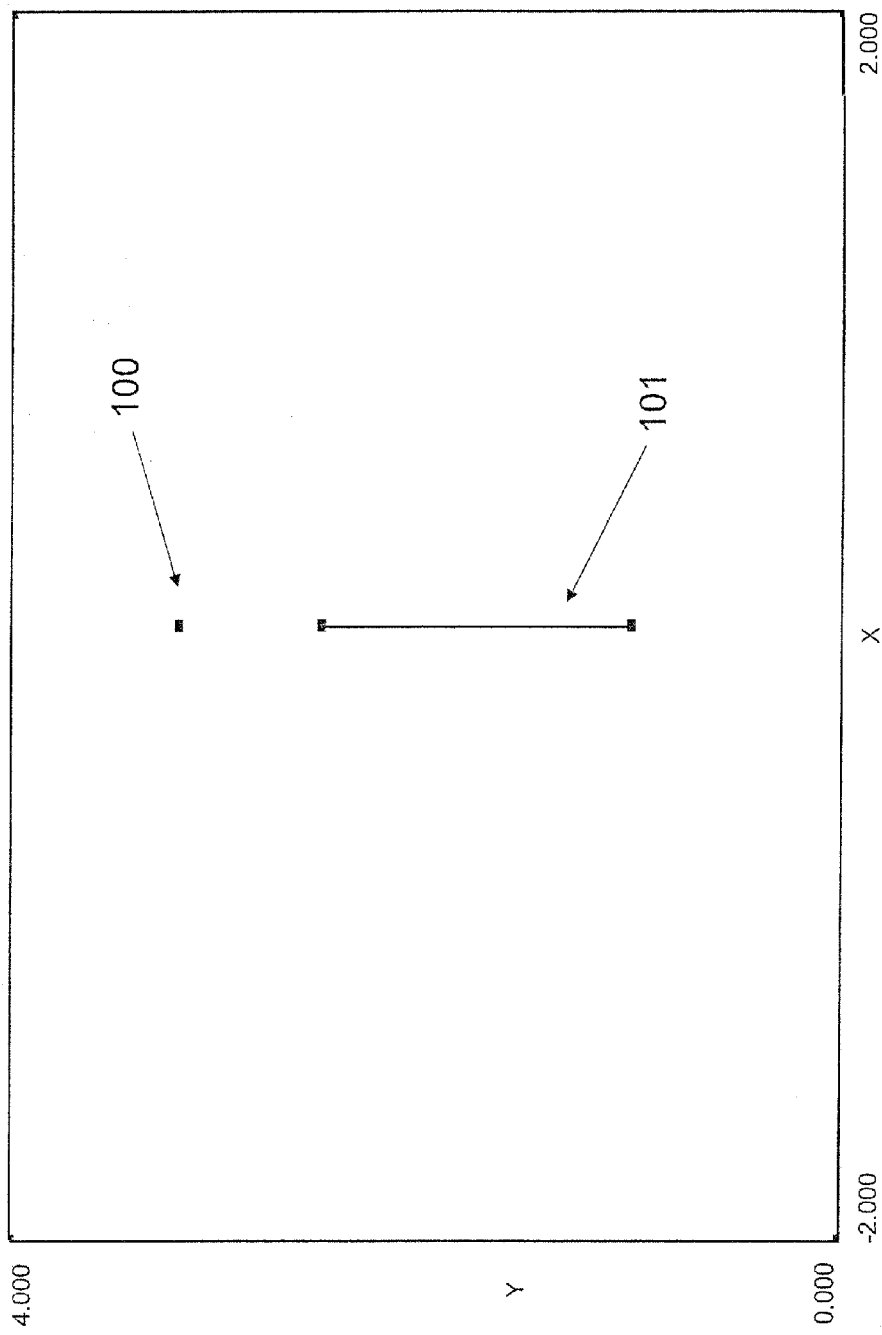

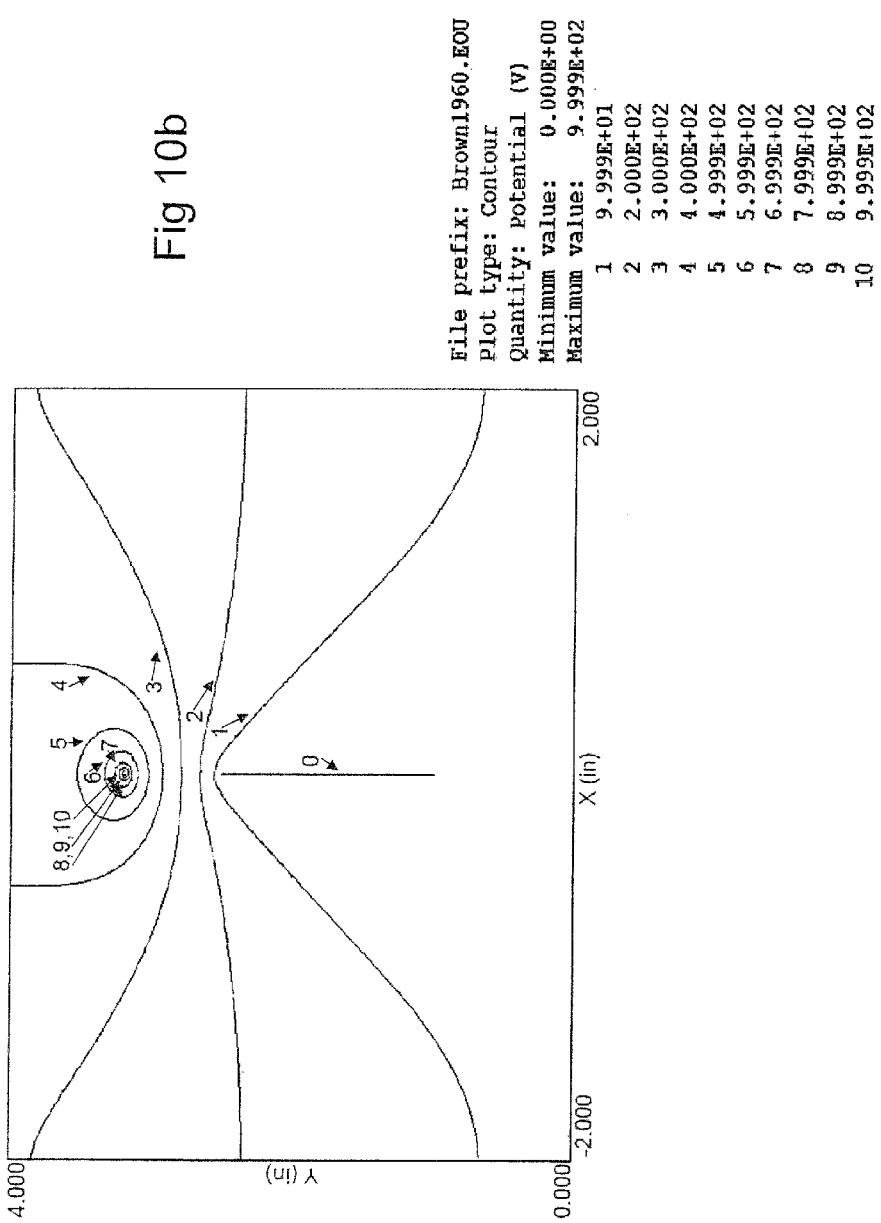

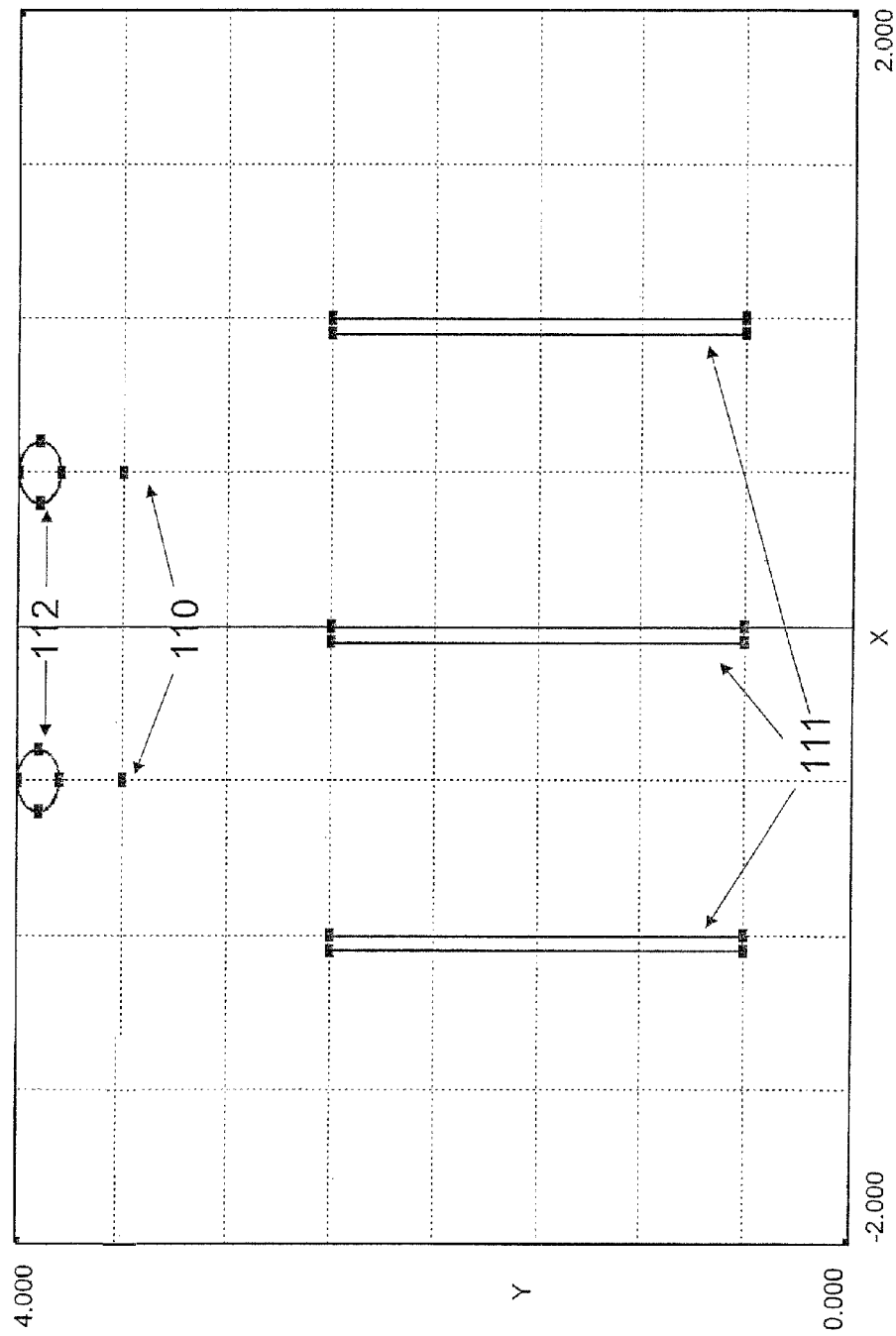

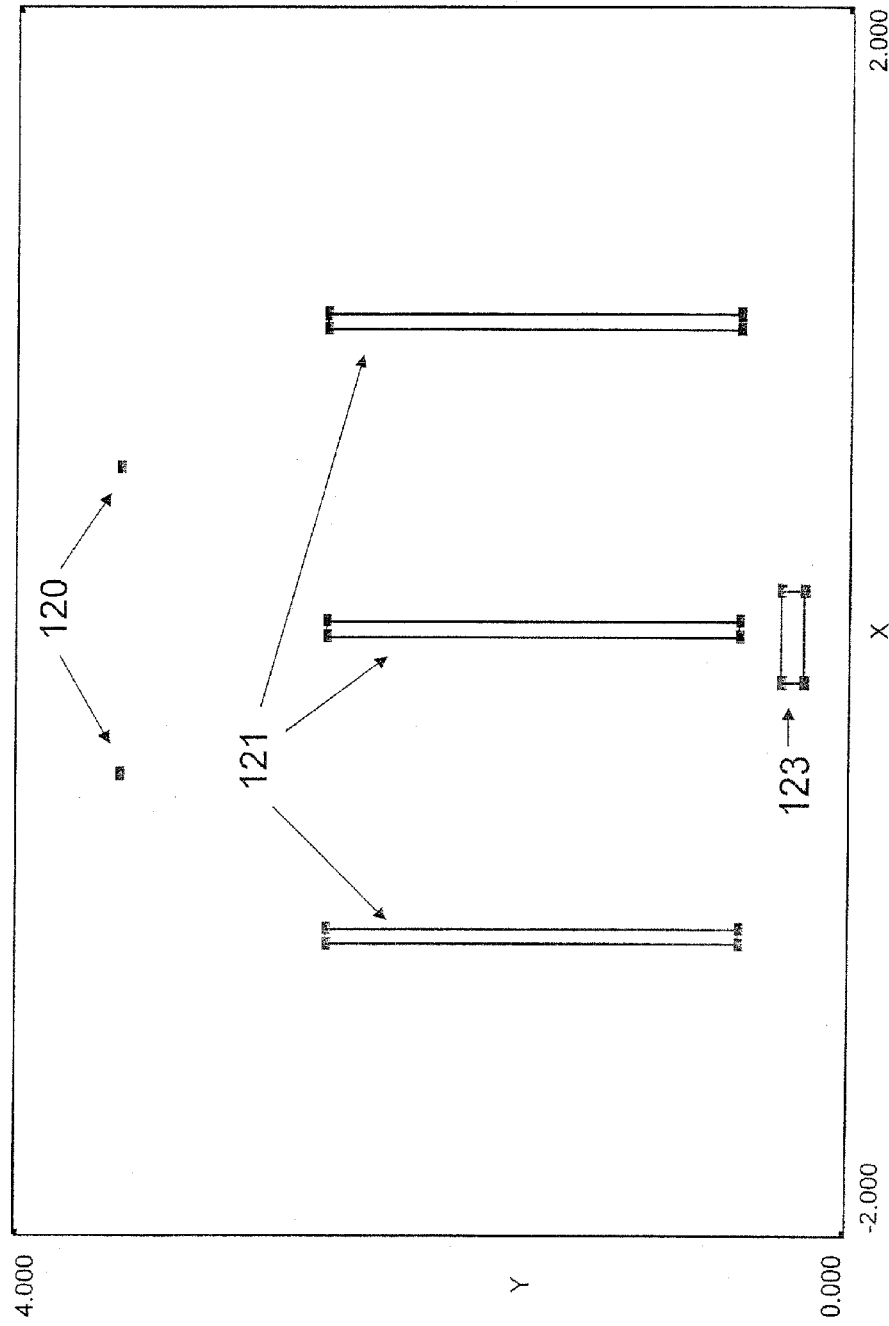

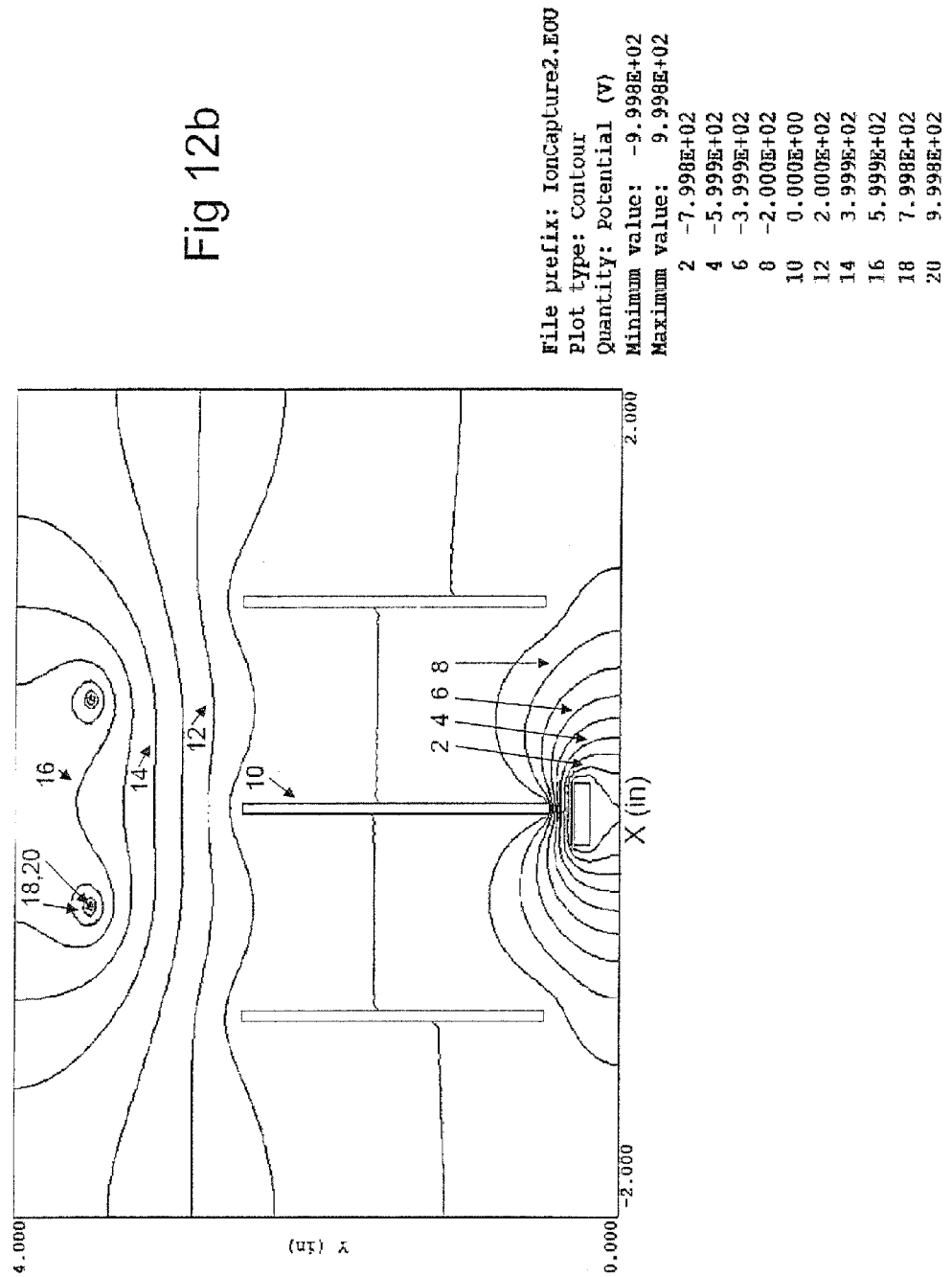

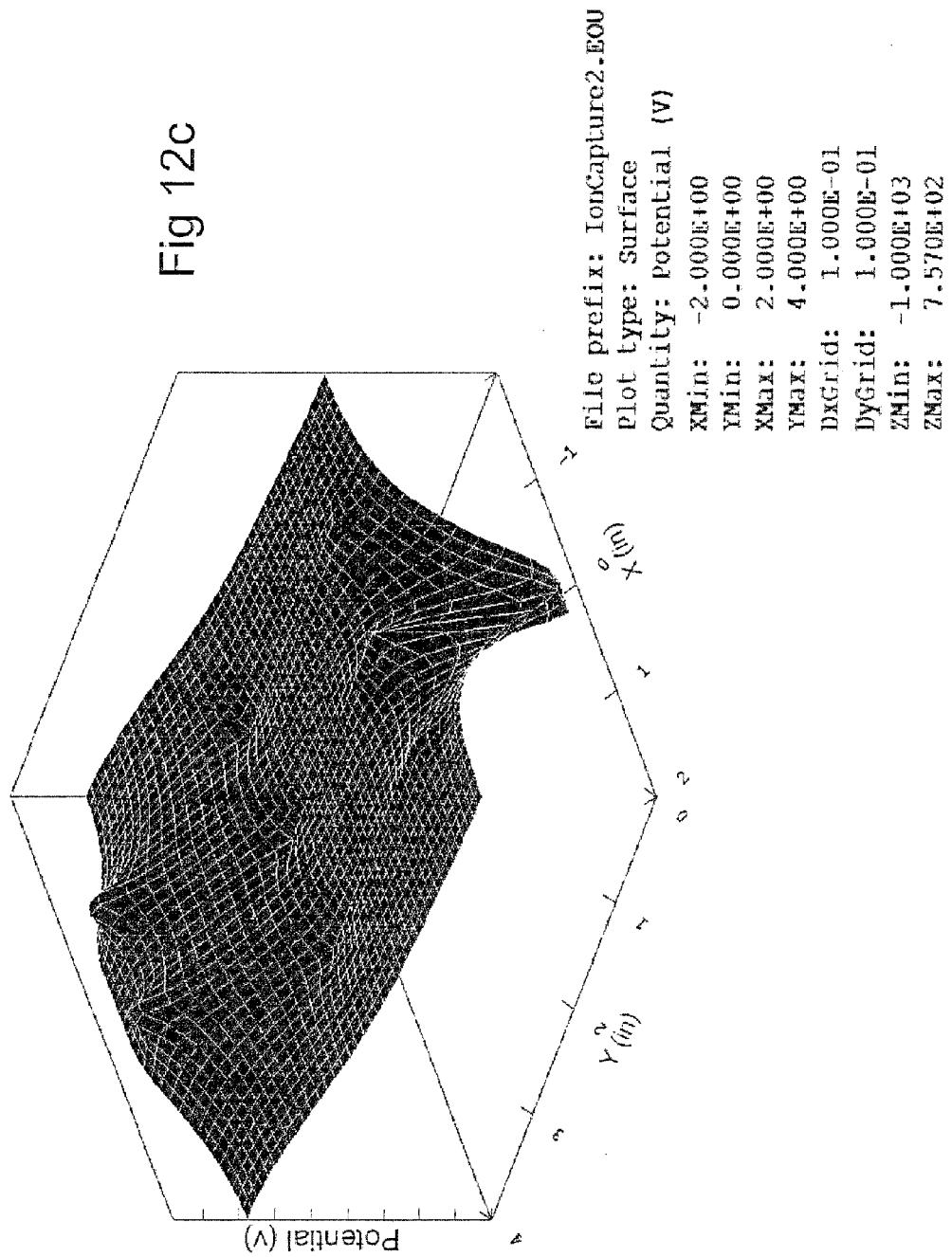

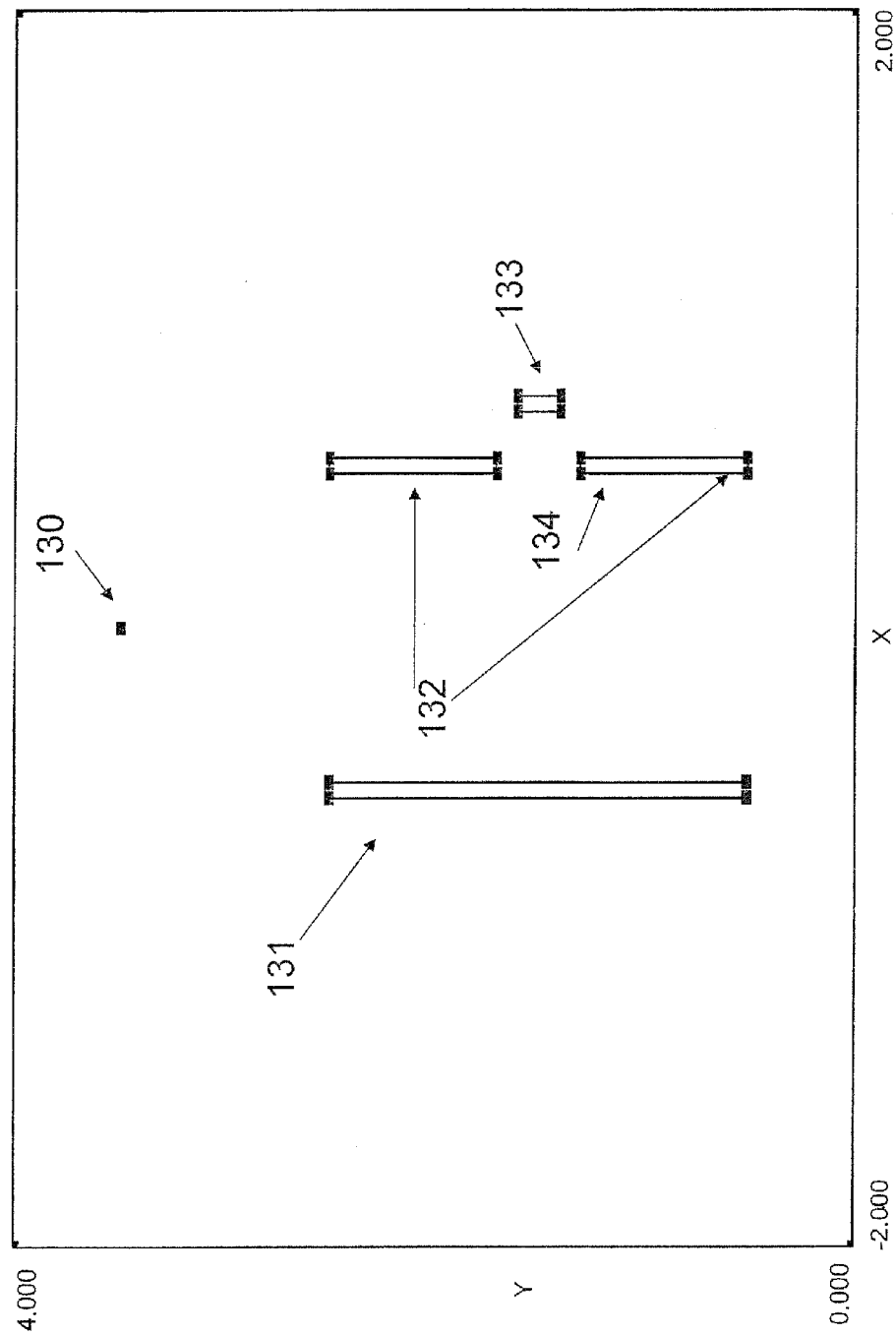

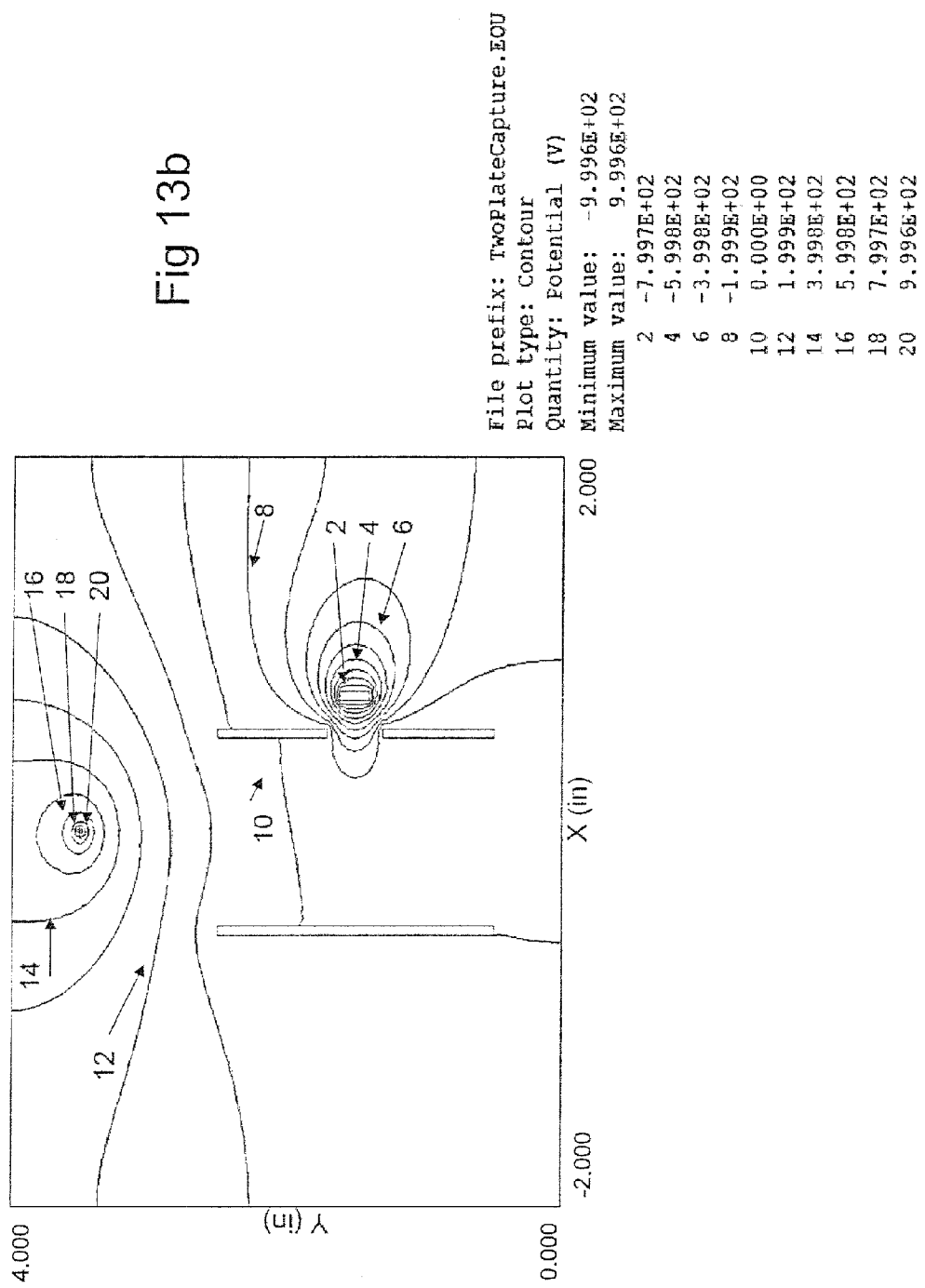

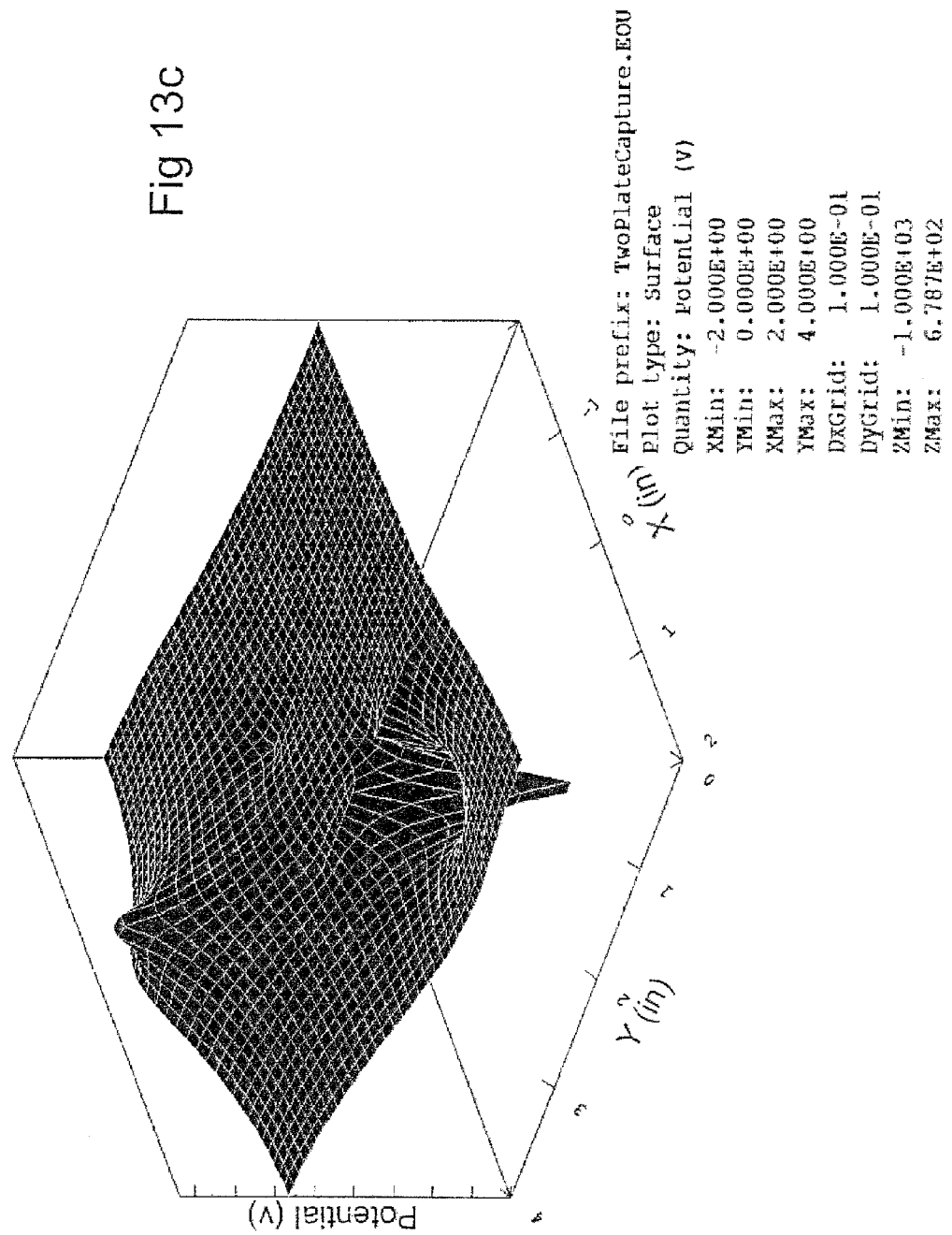

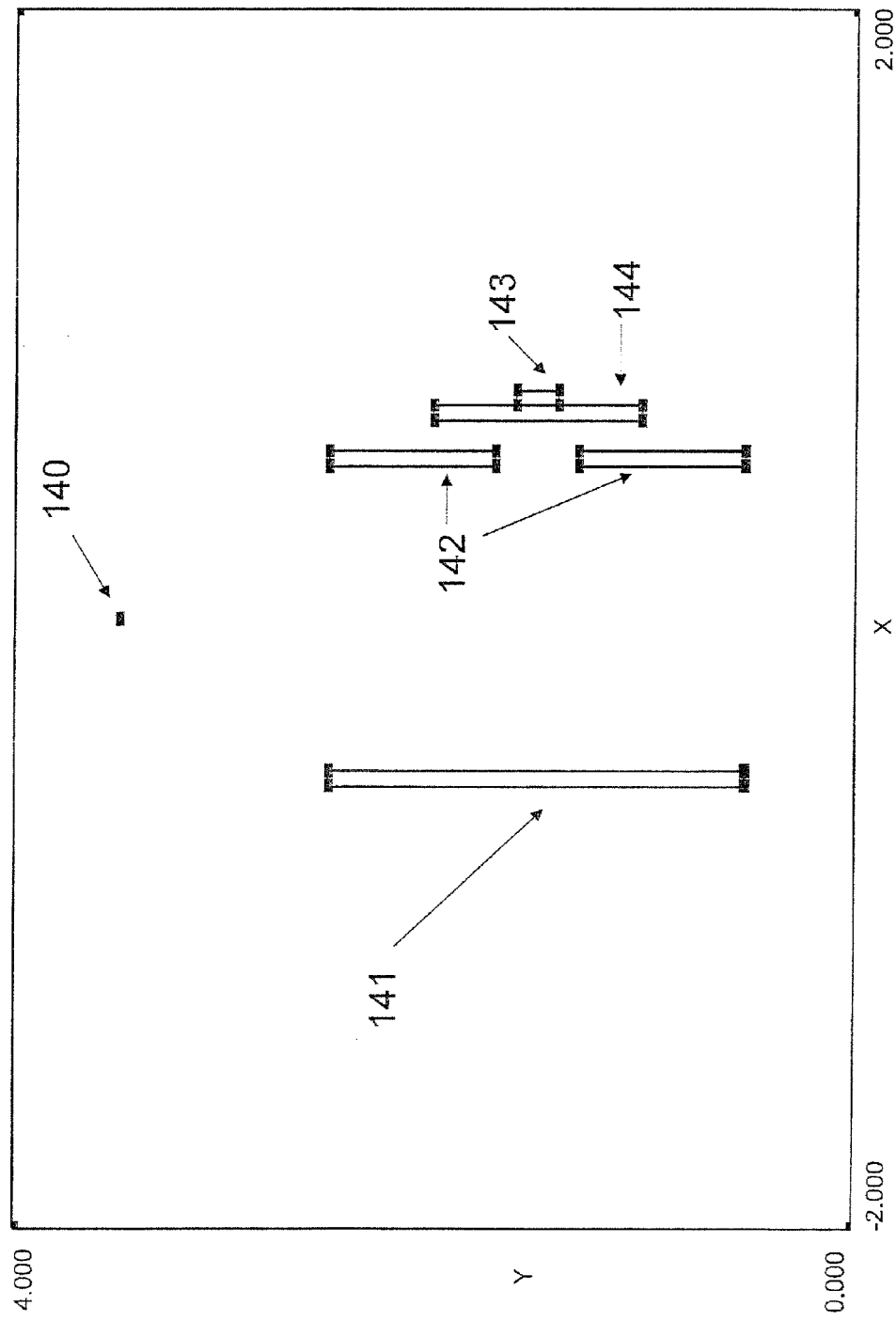

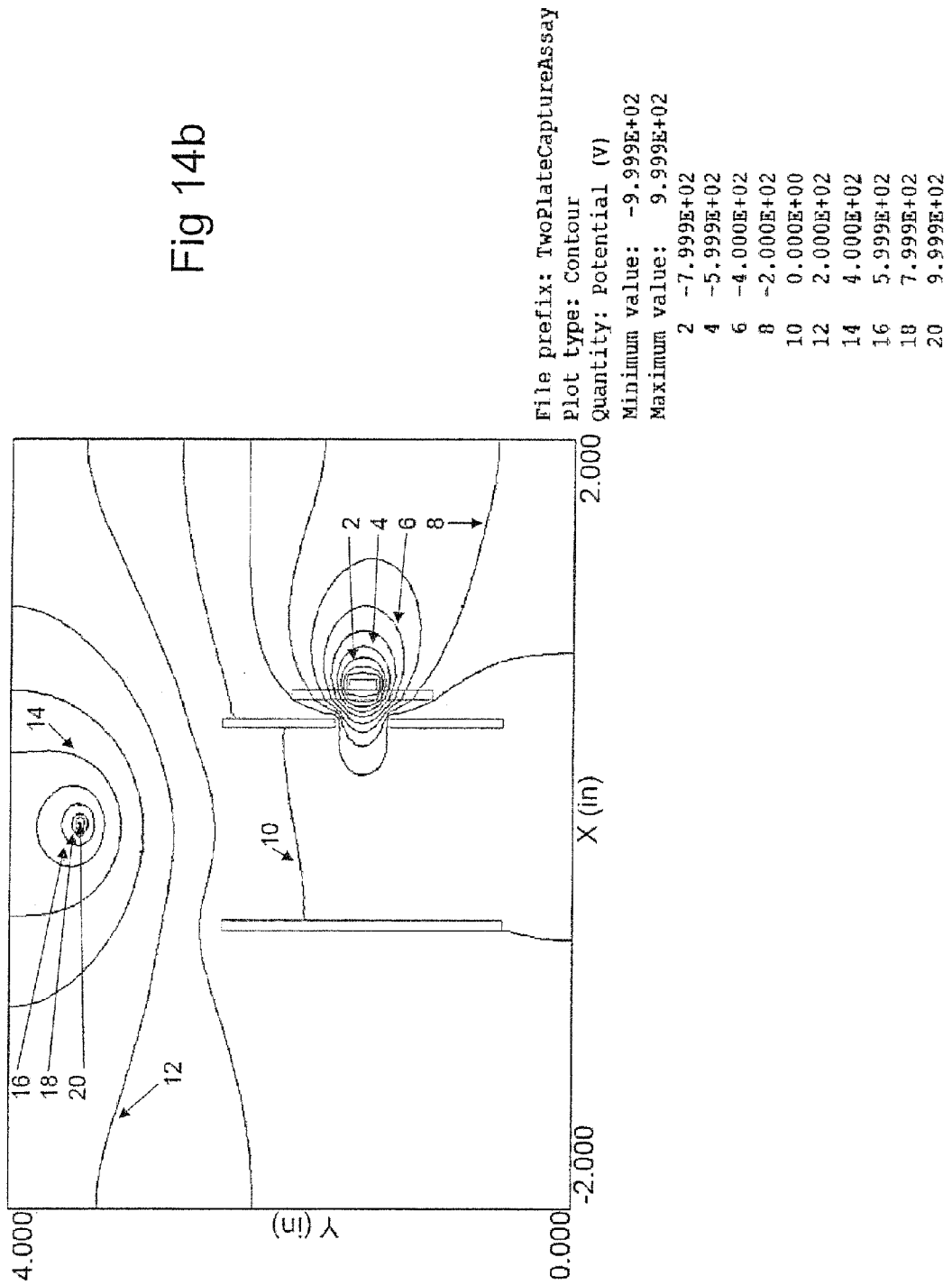

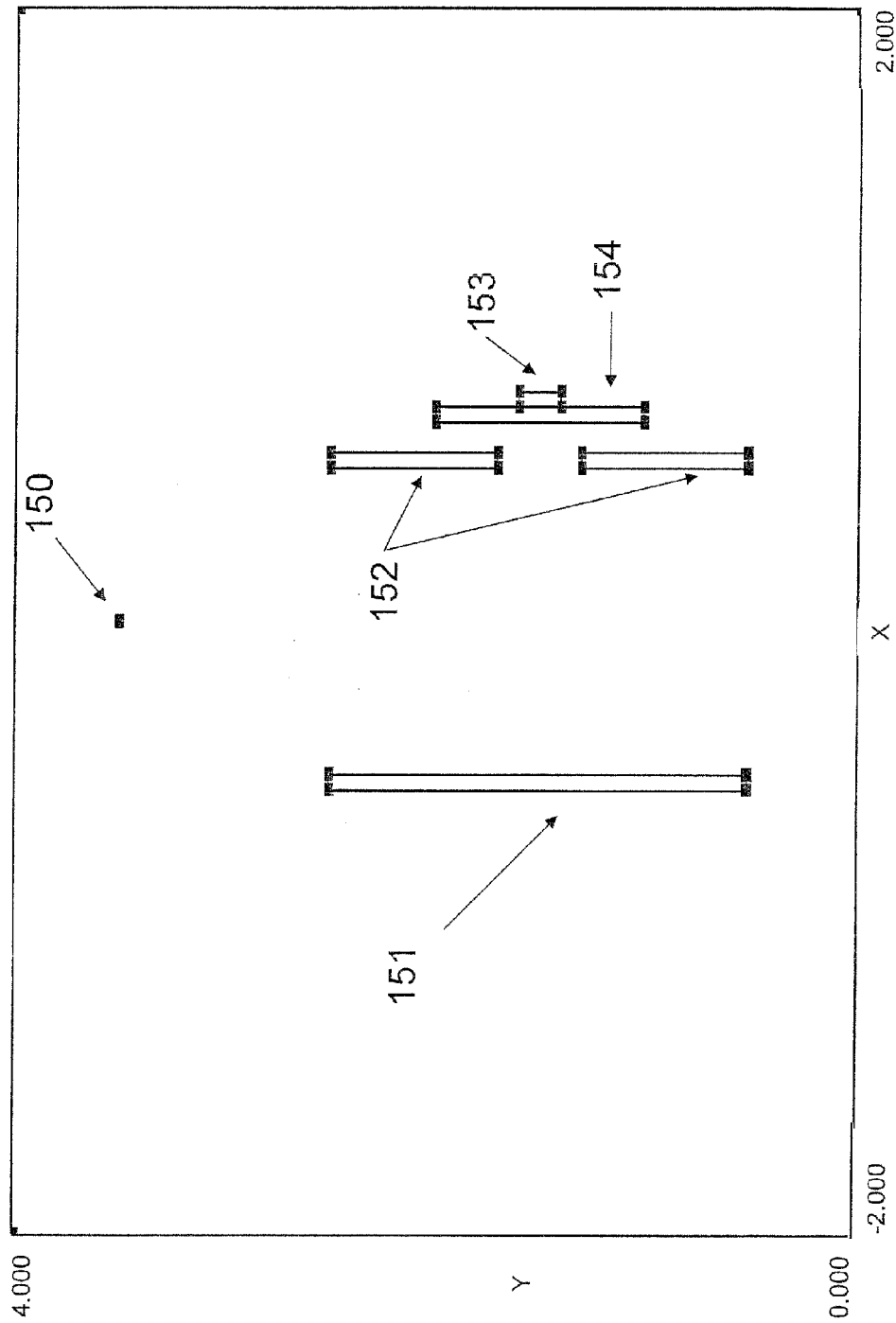

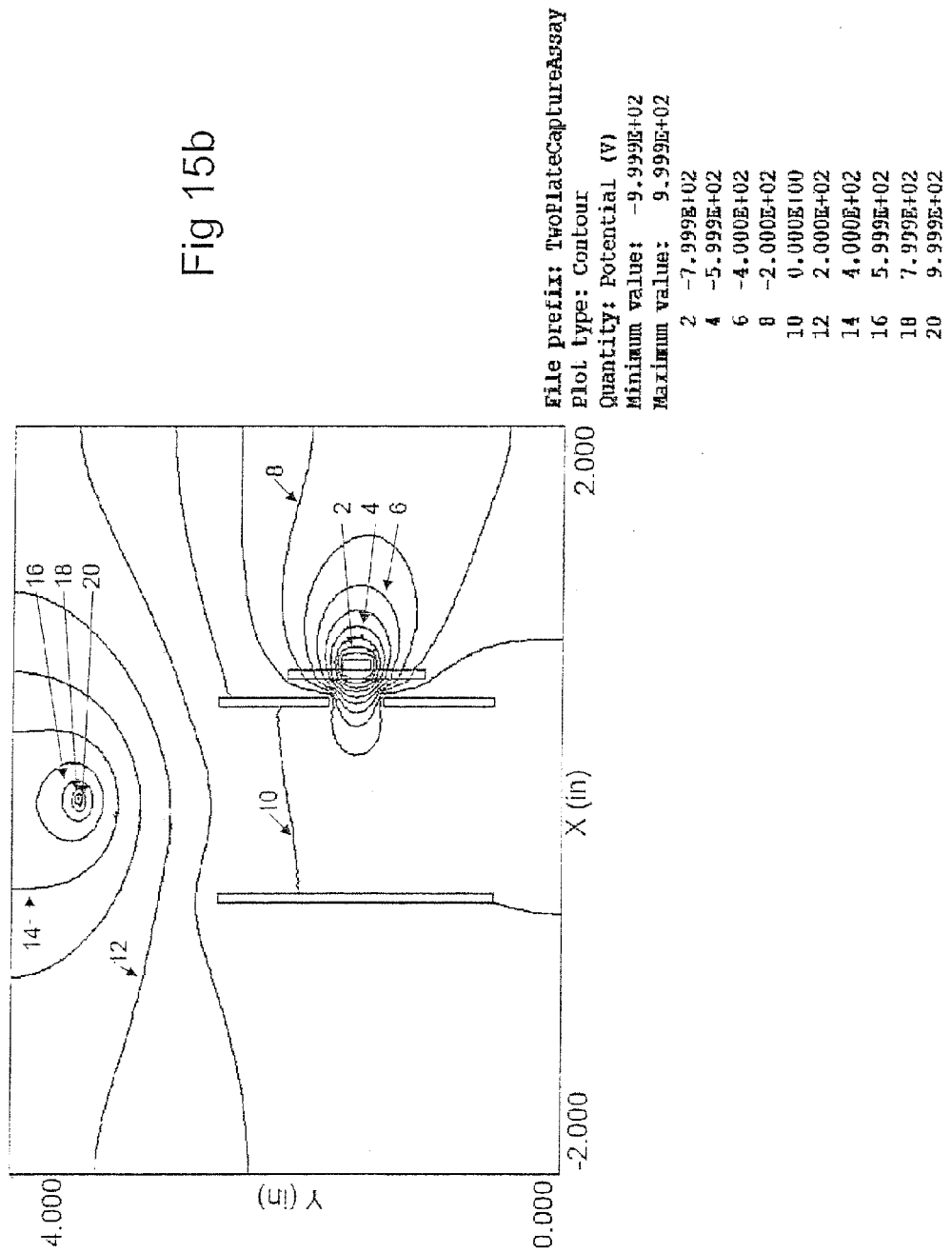

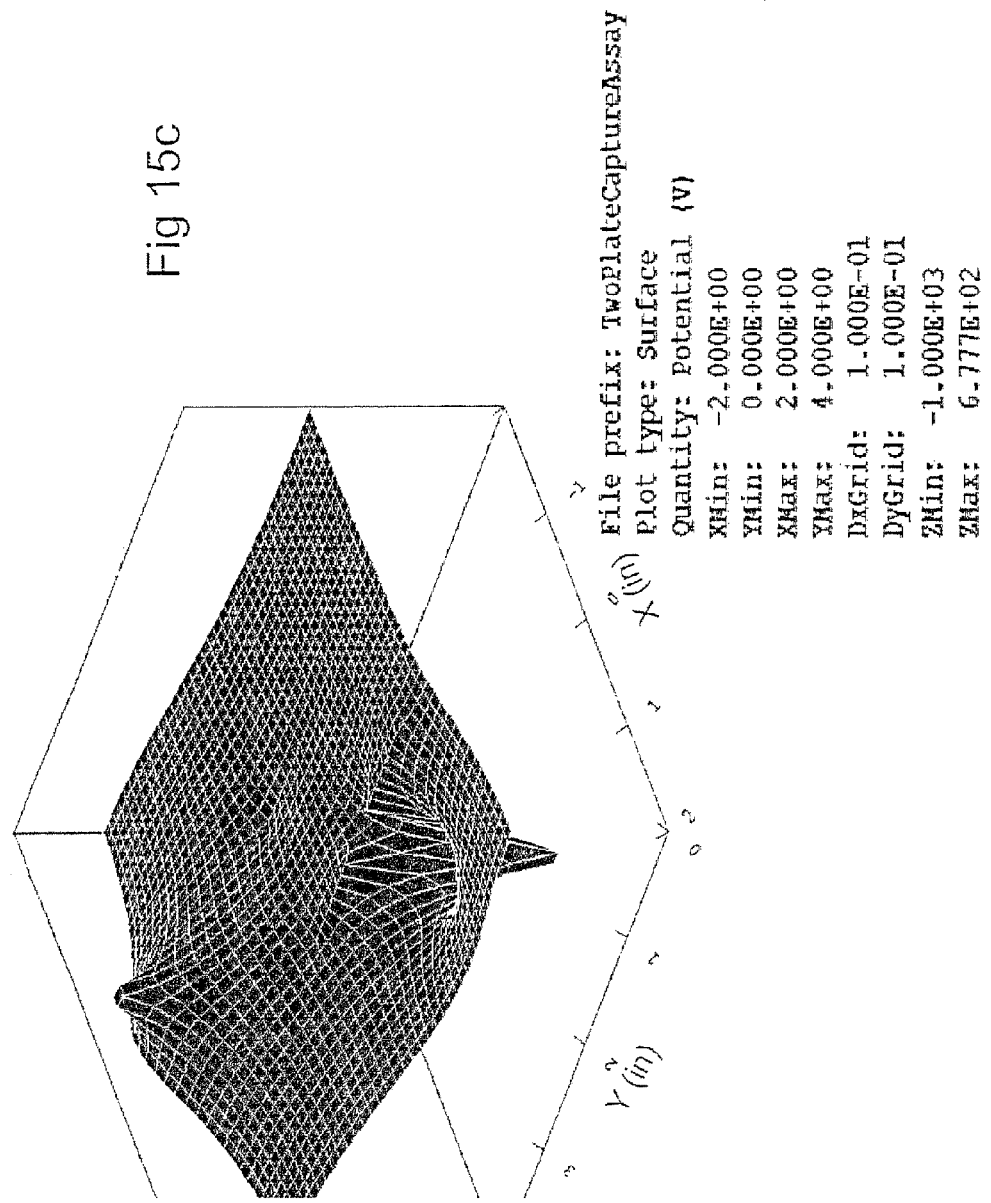

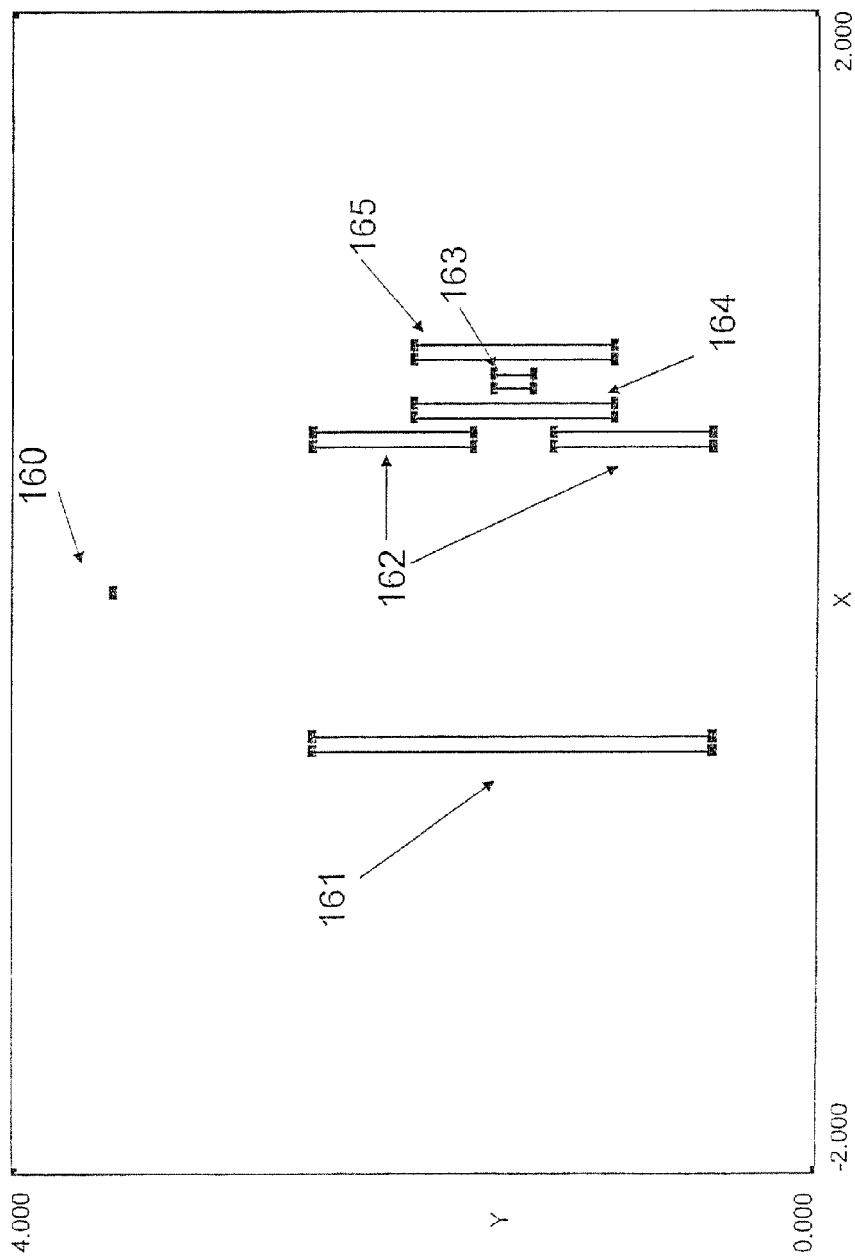

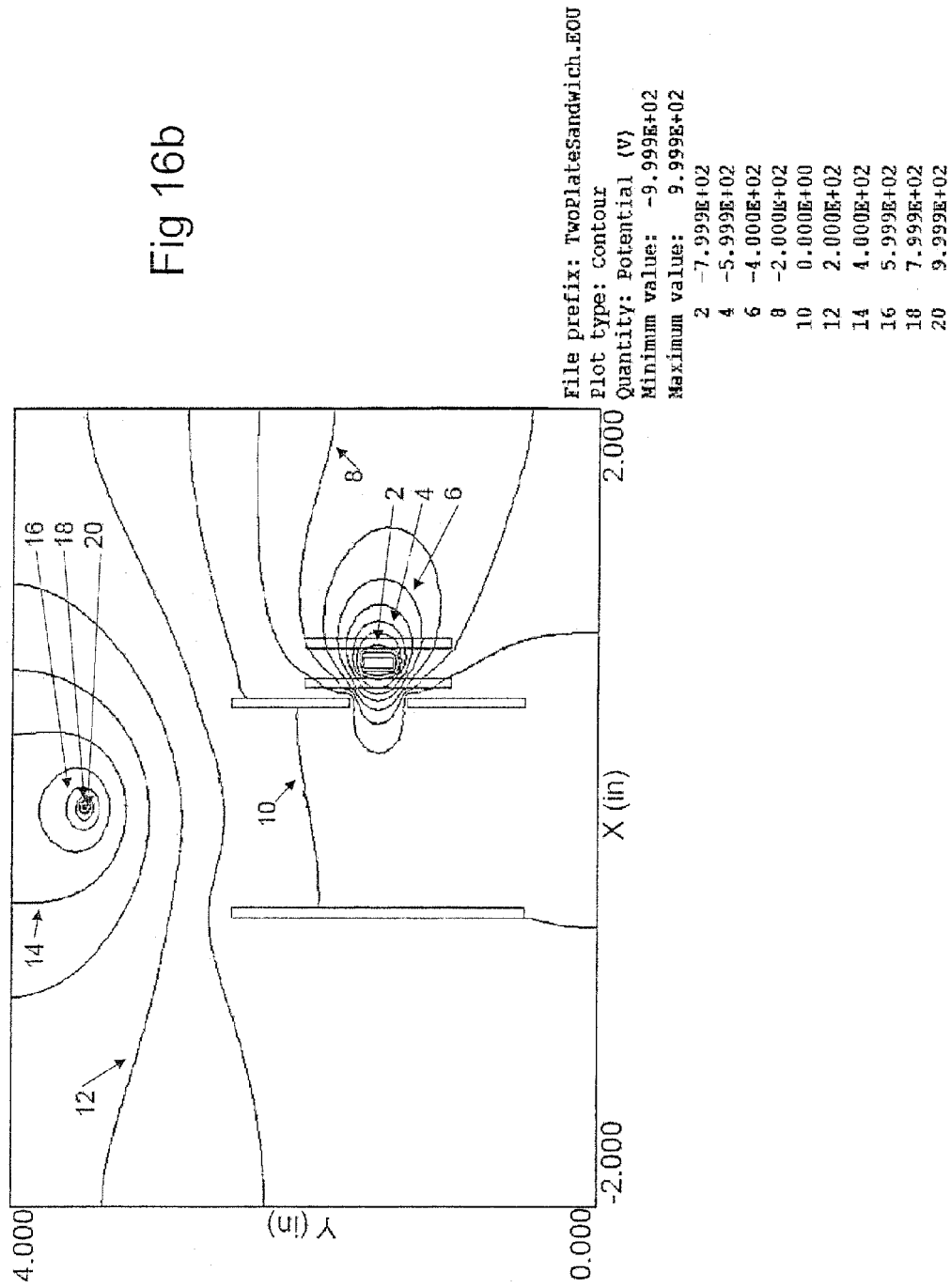

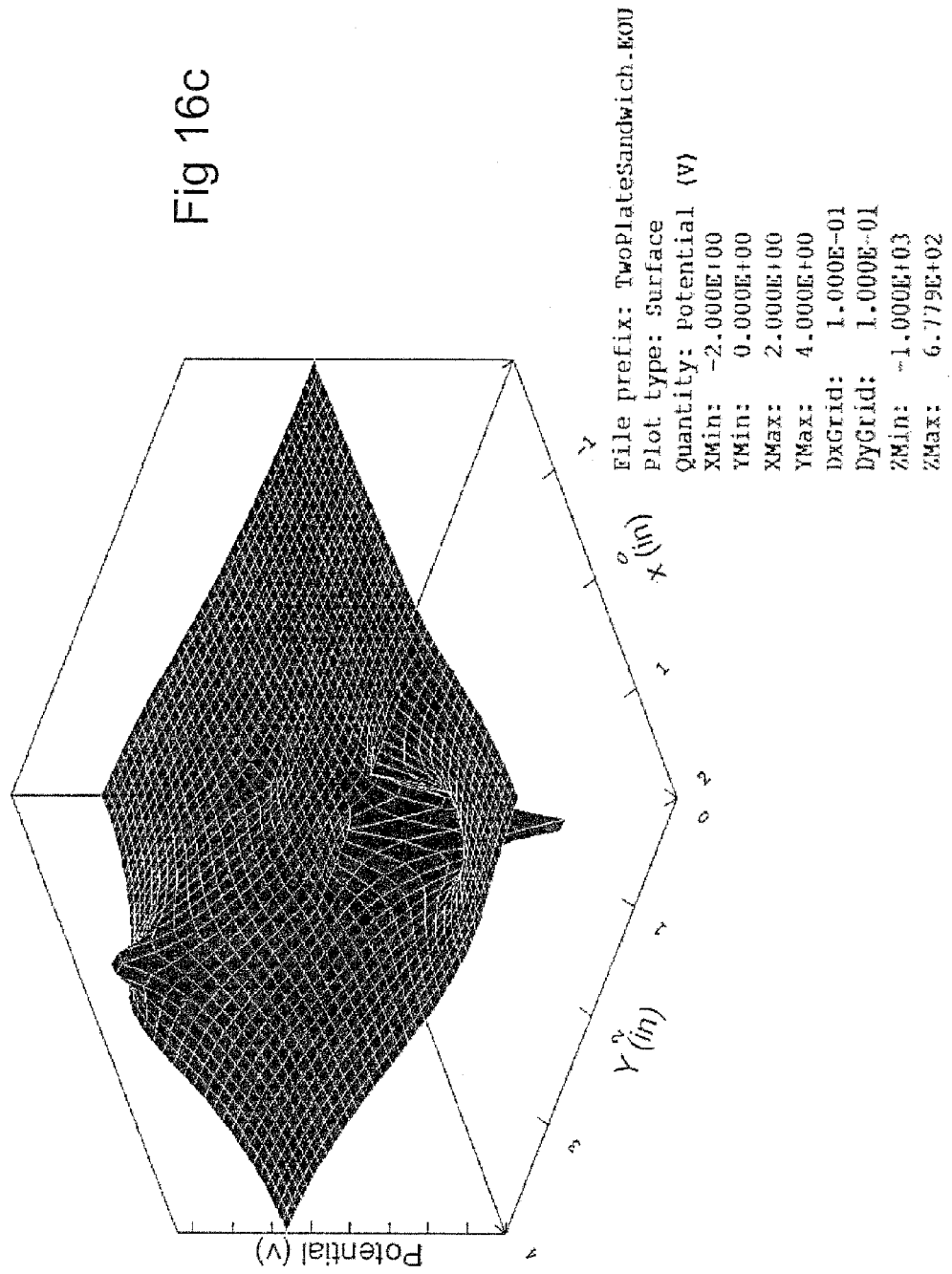

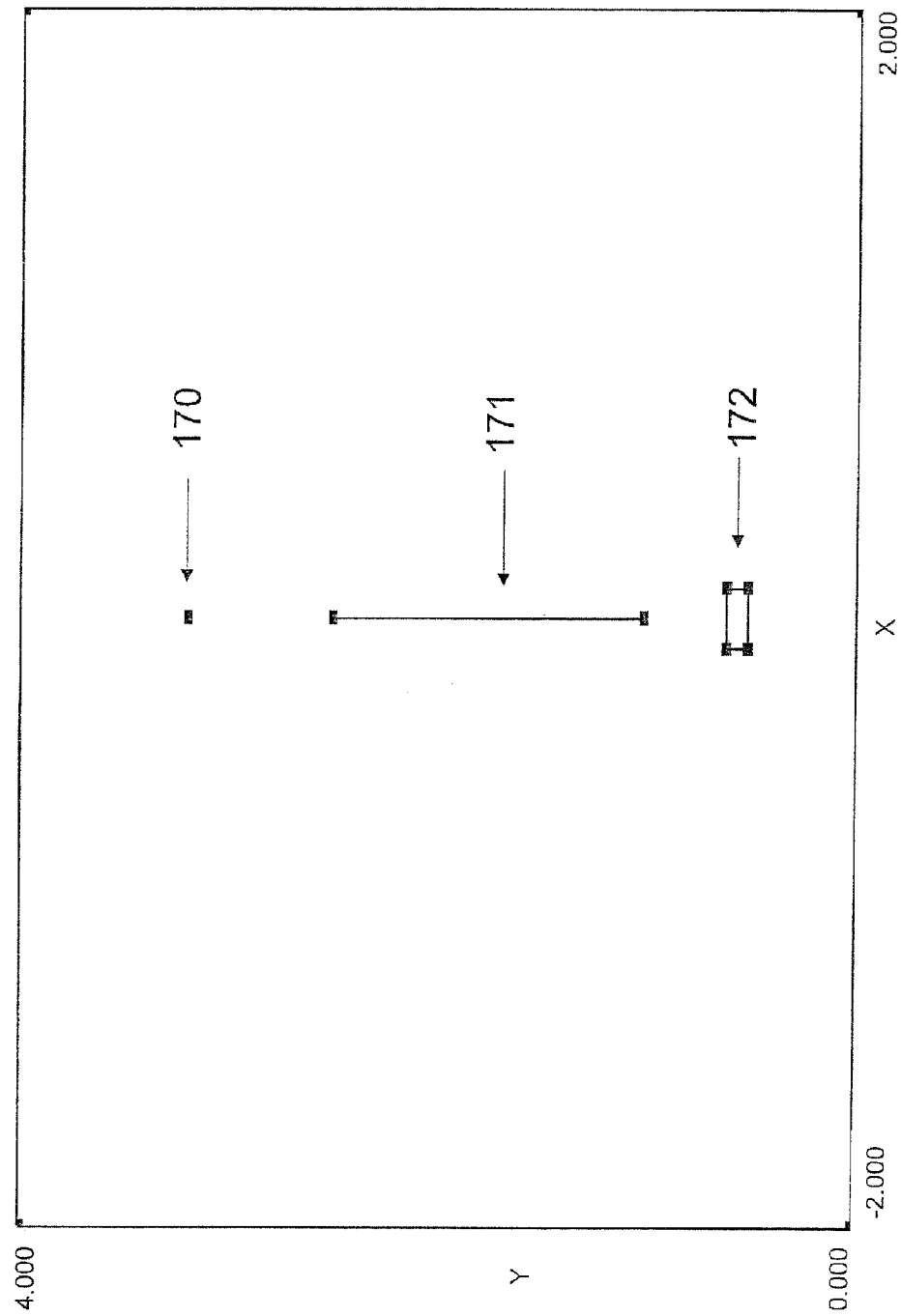

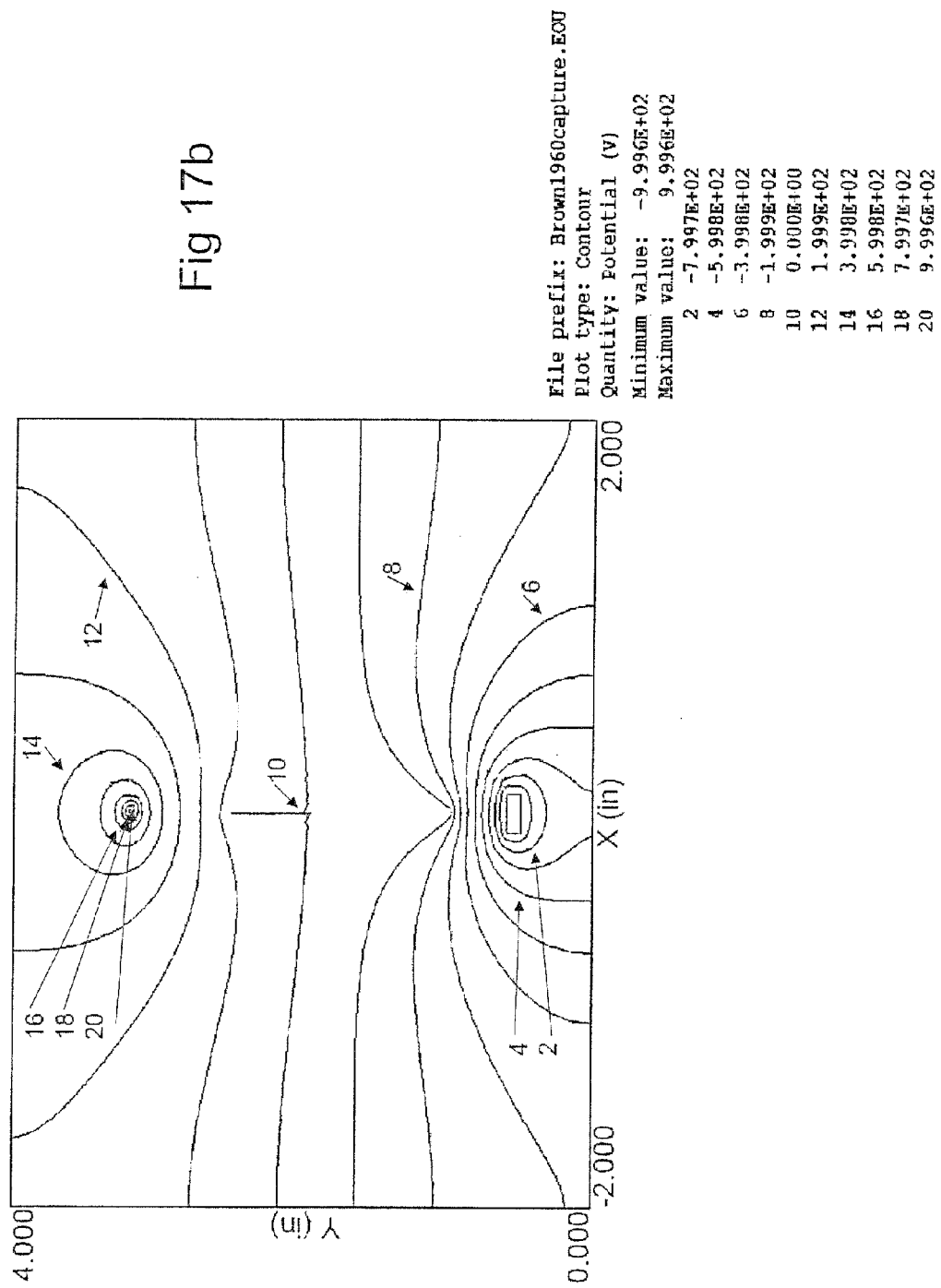

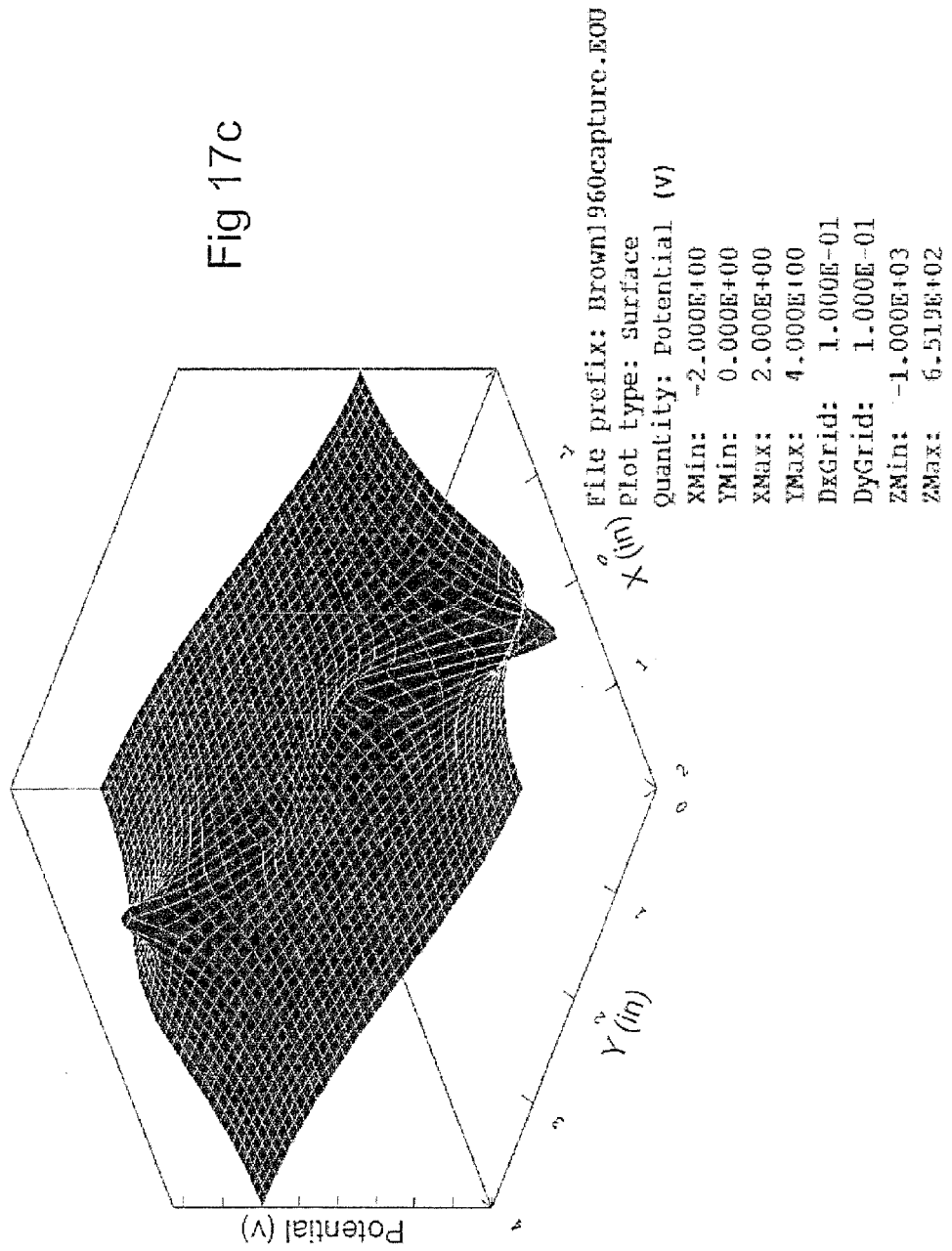

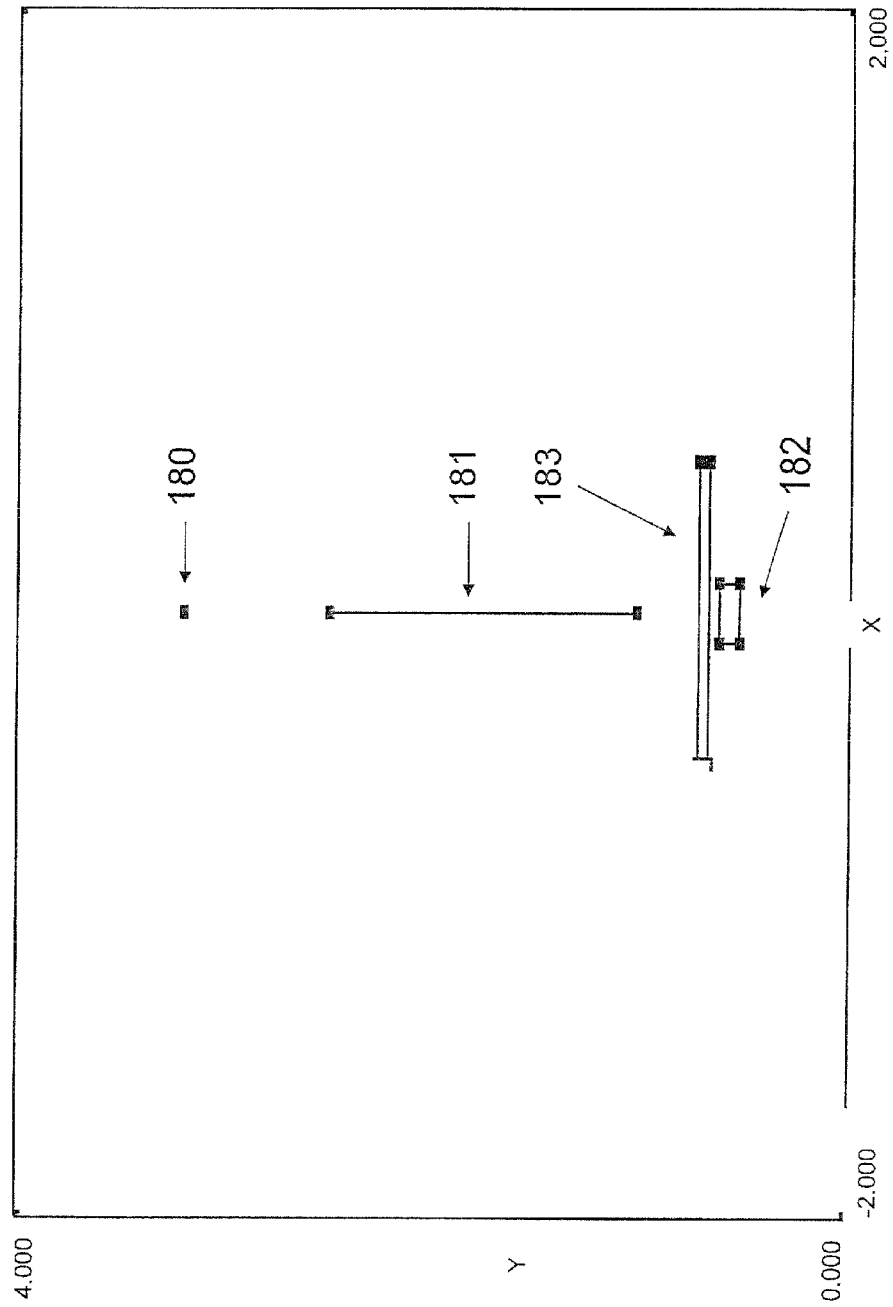

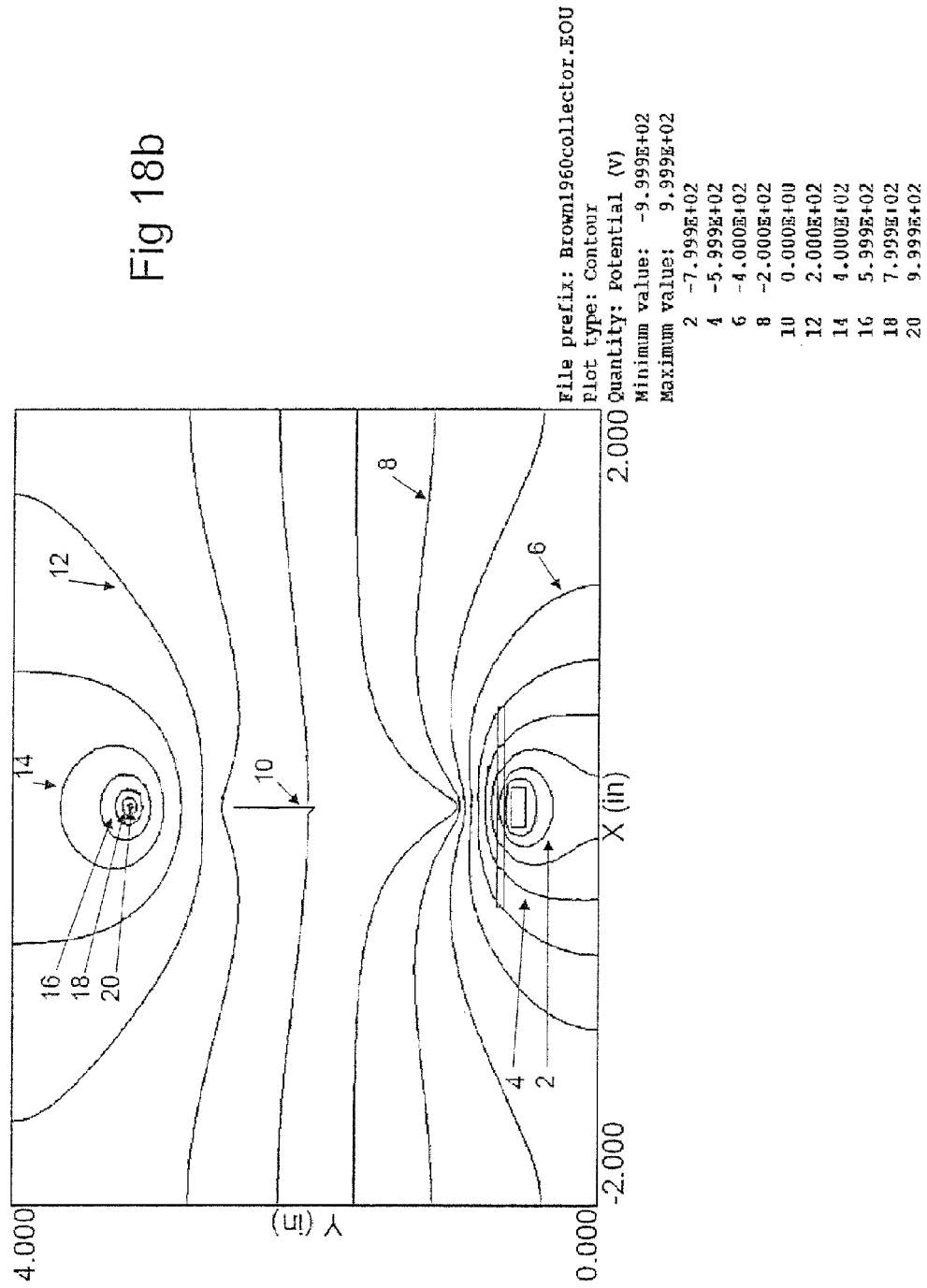

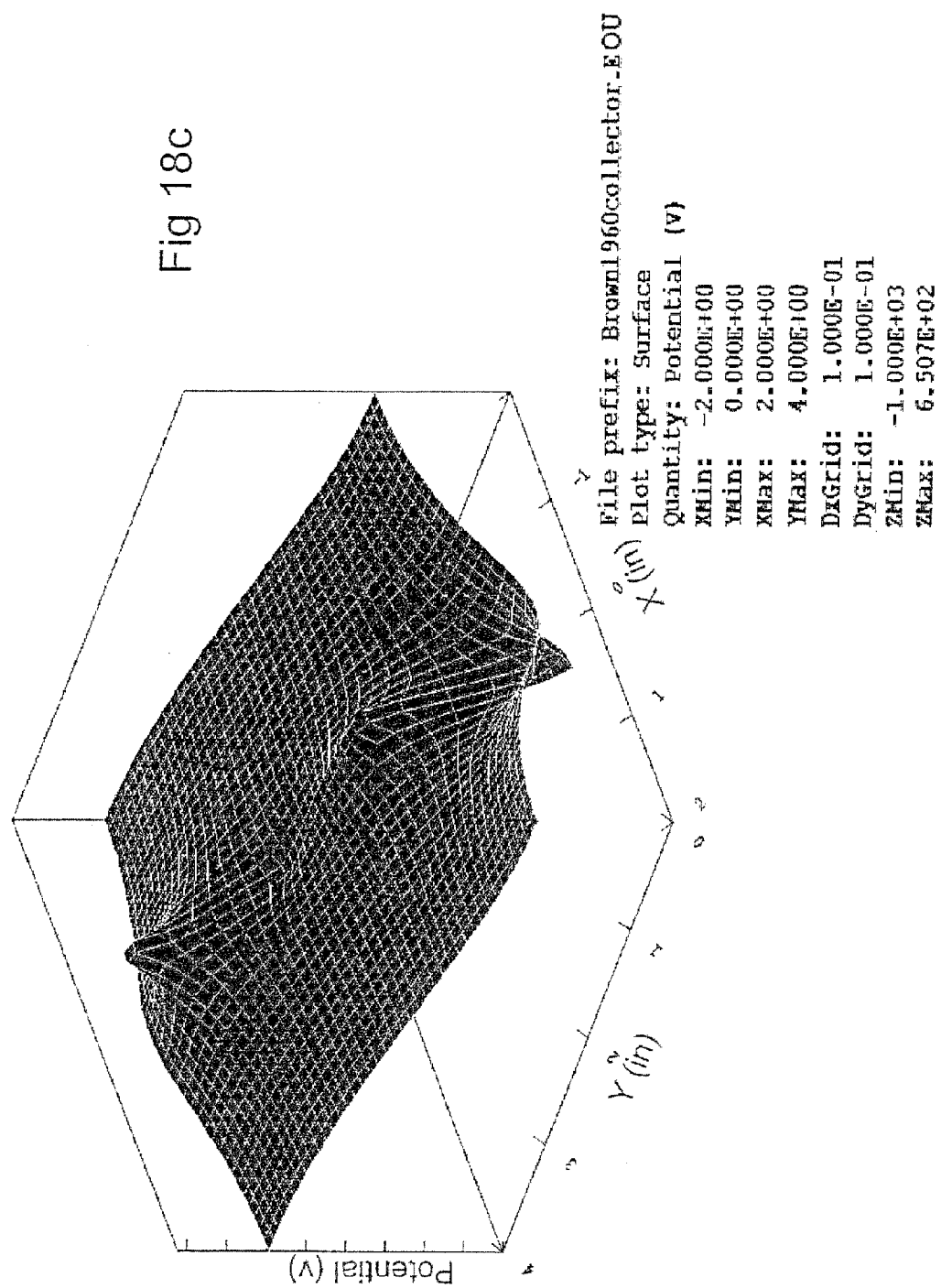

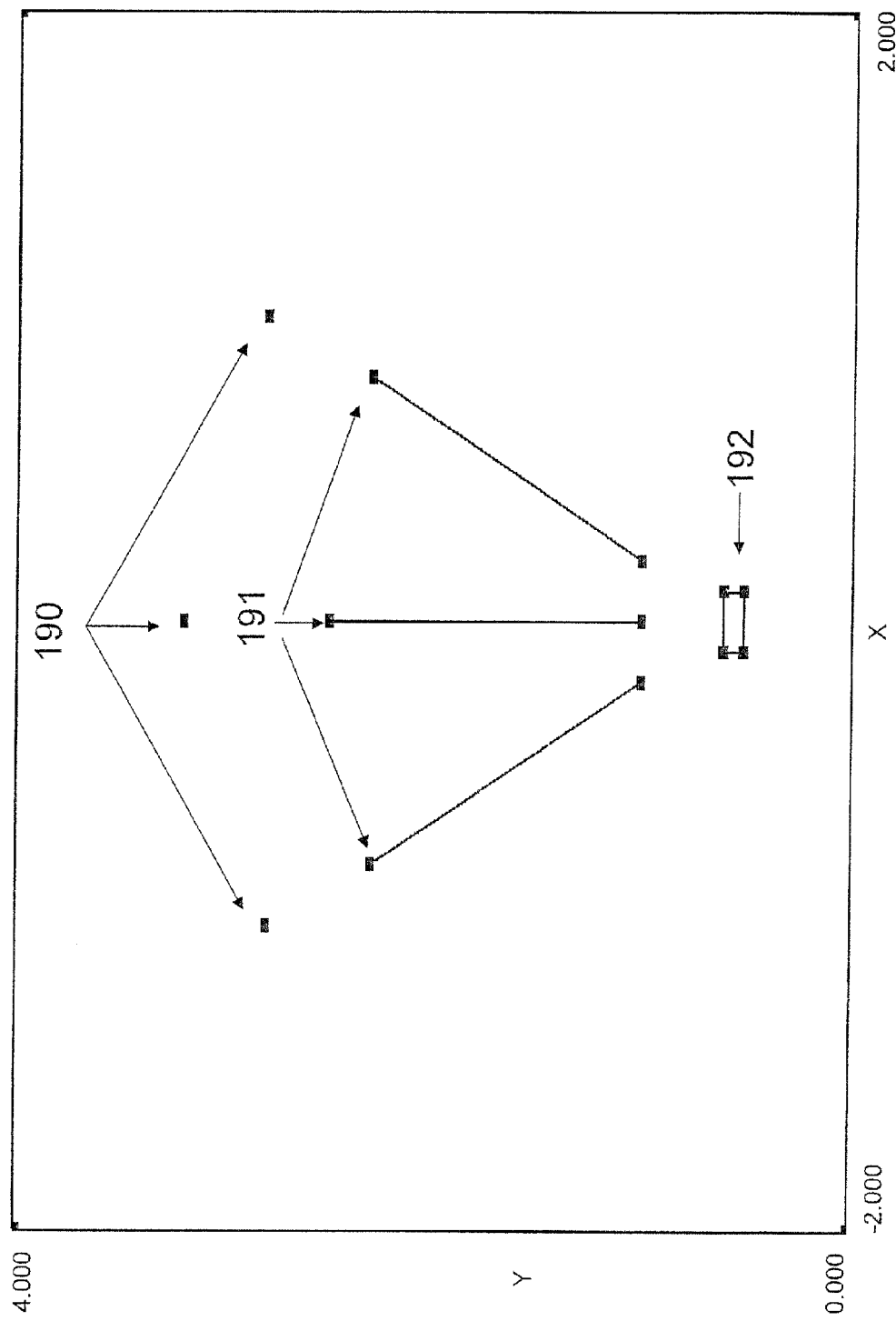

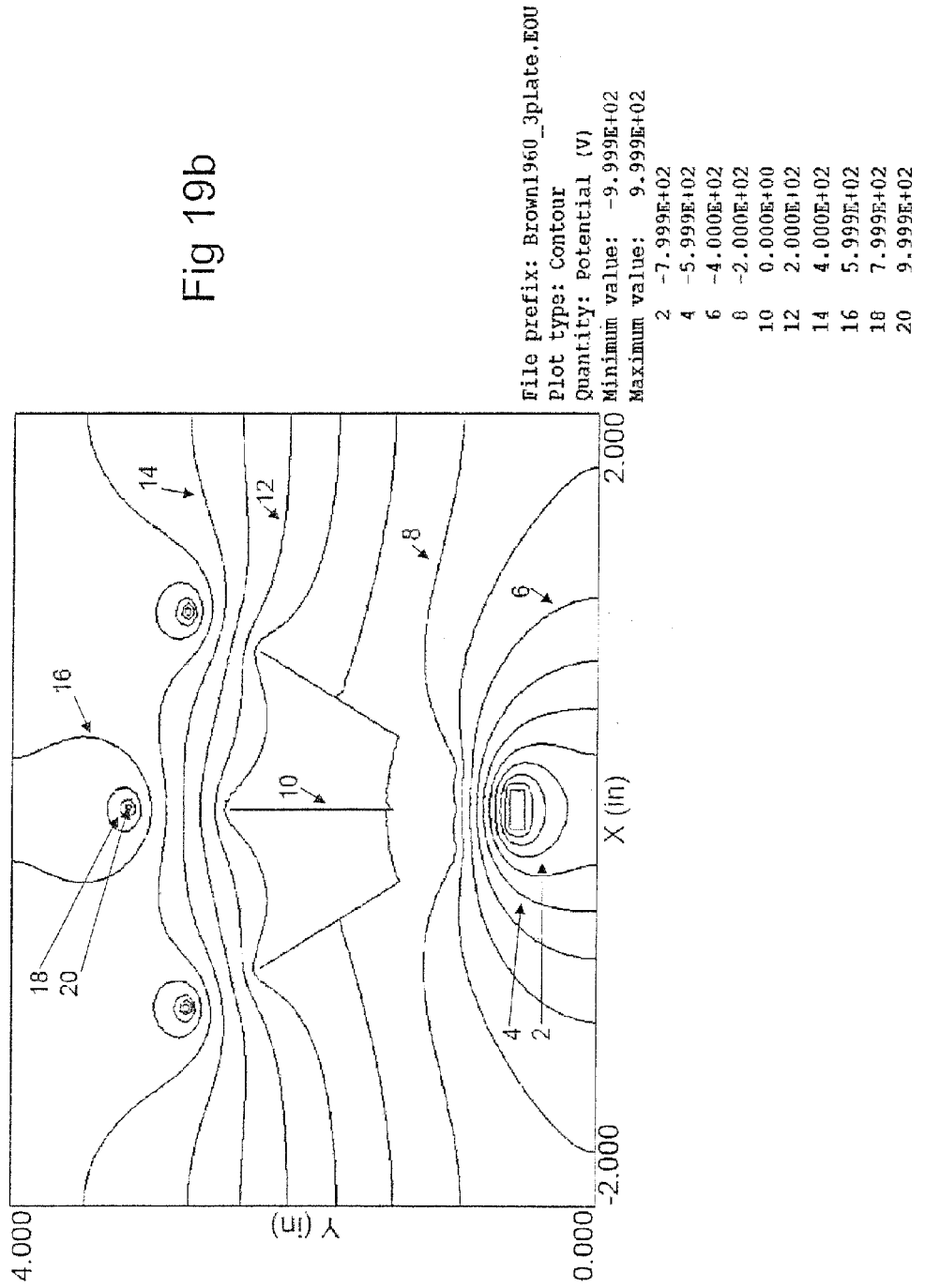

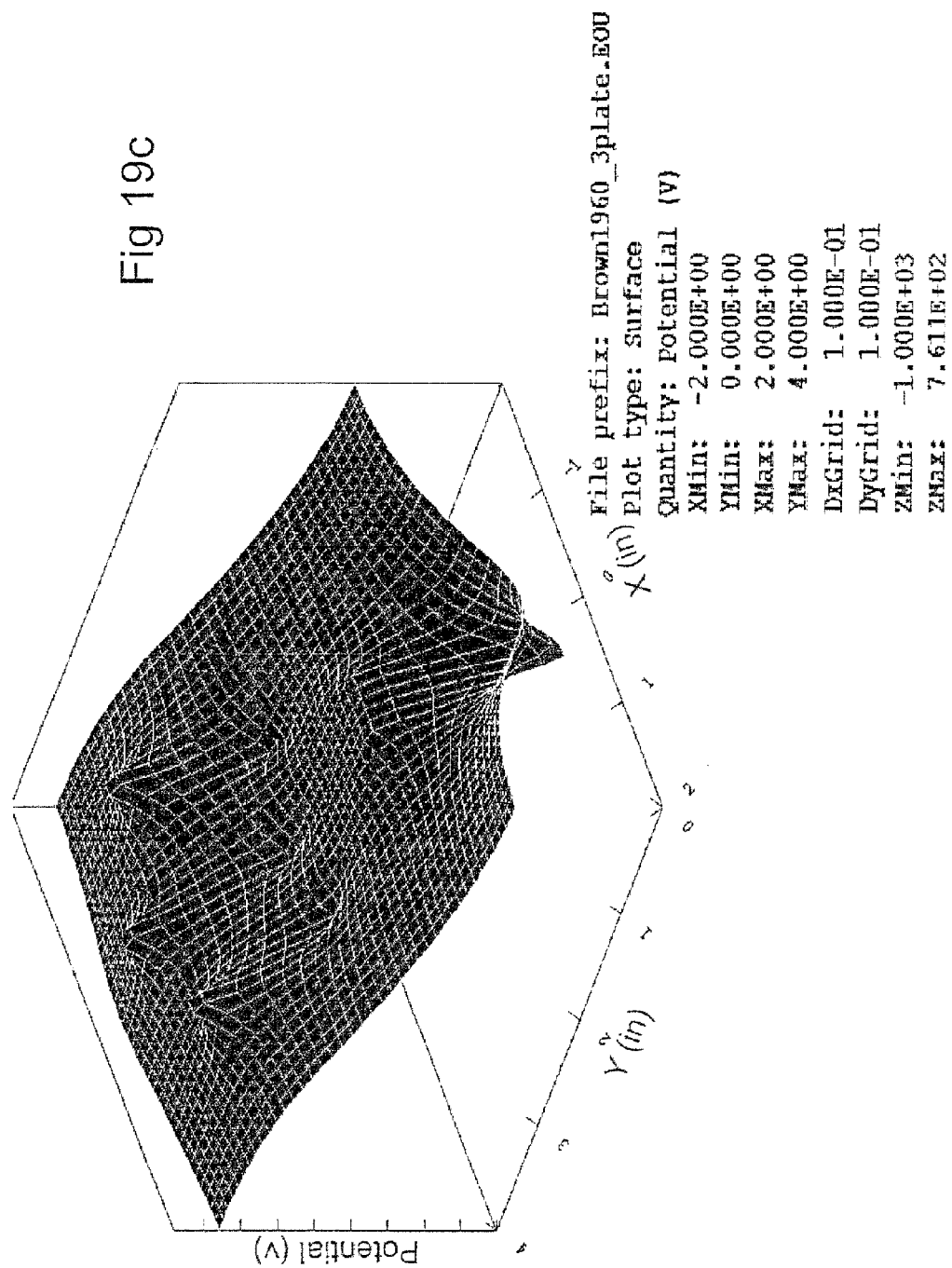

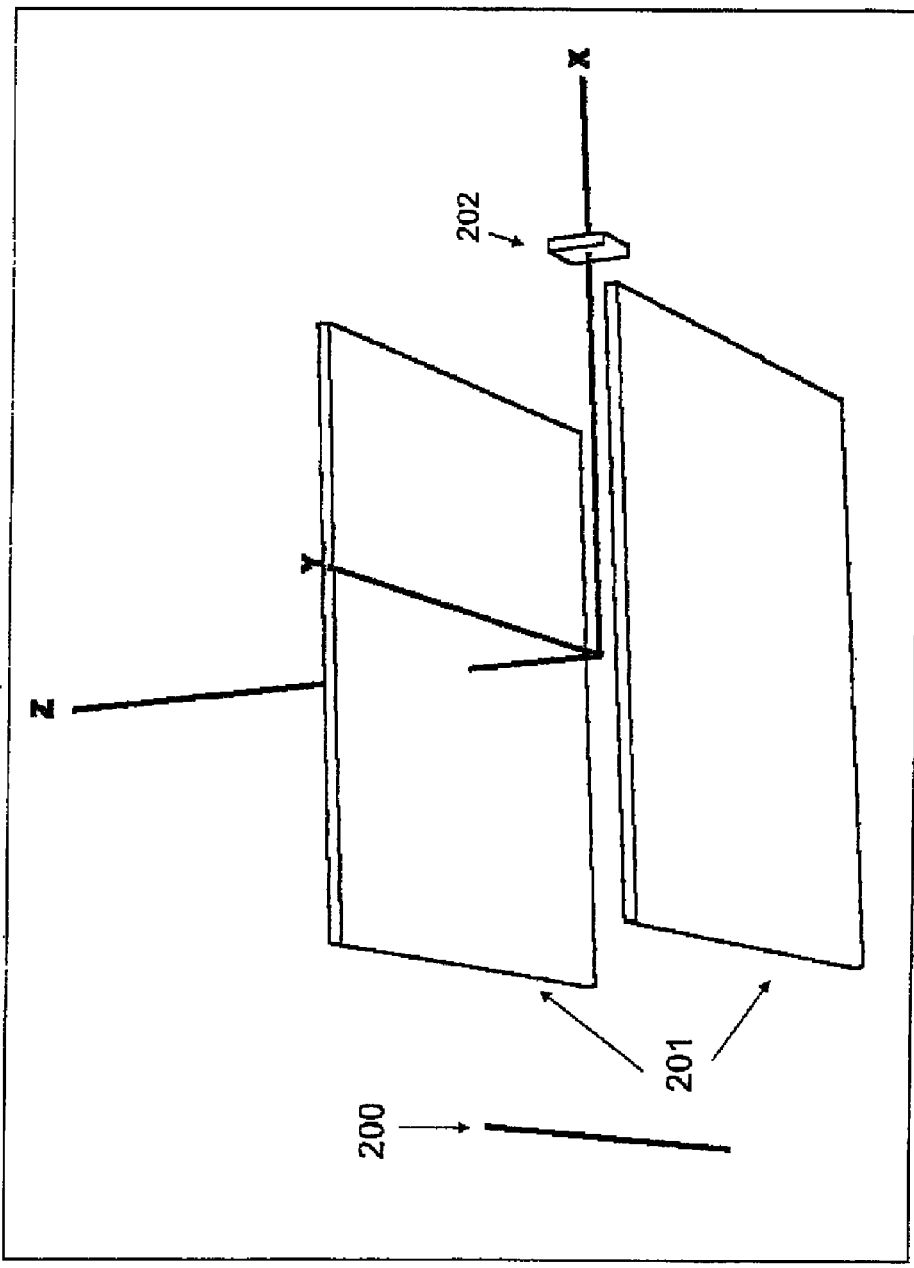

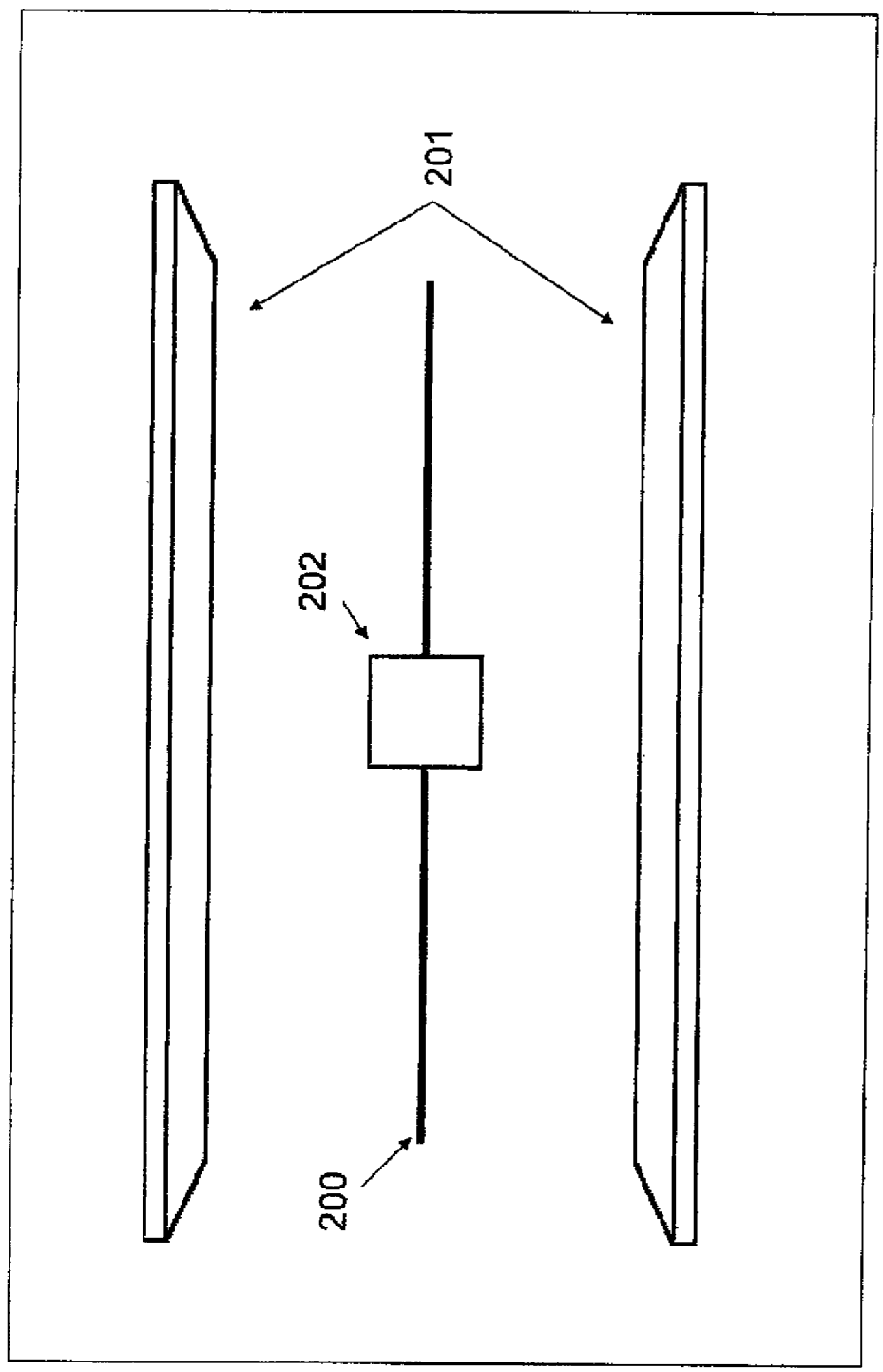

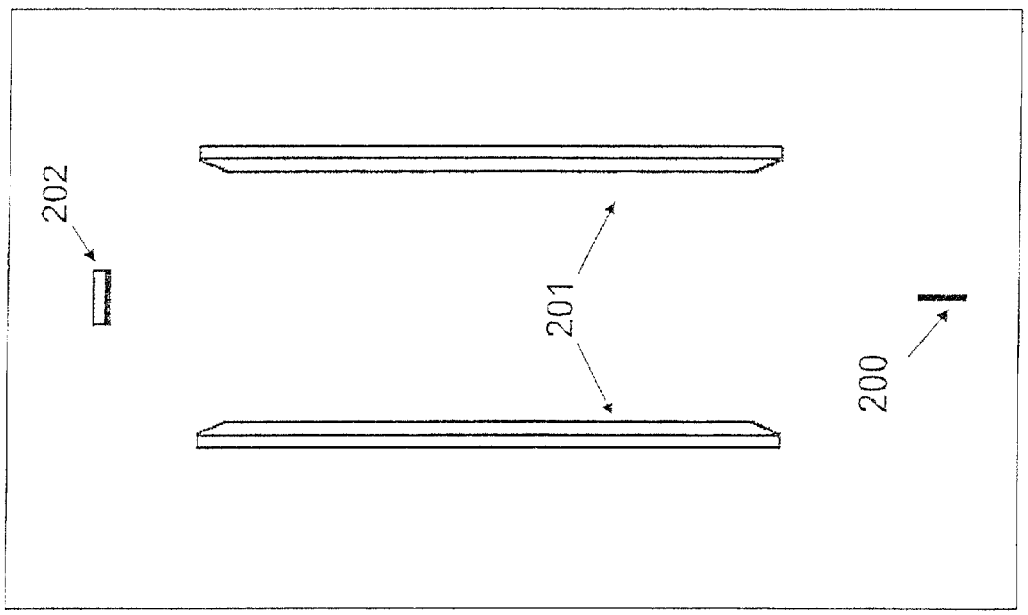

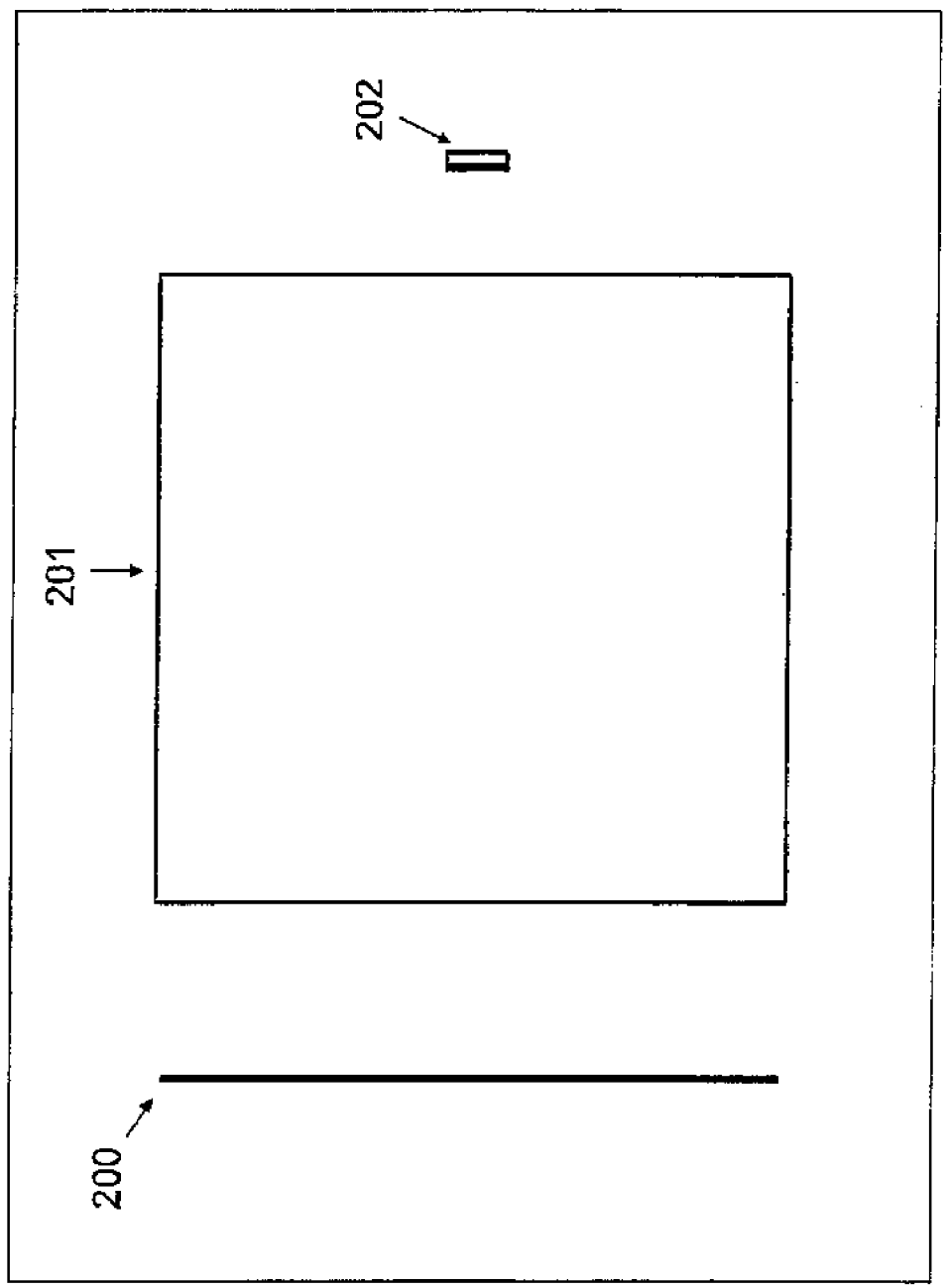

X=-4.95

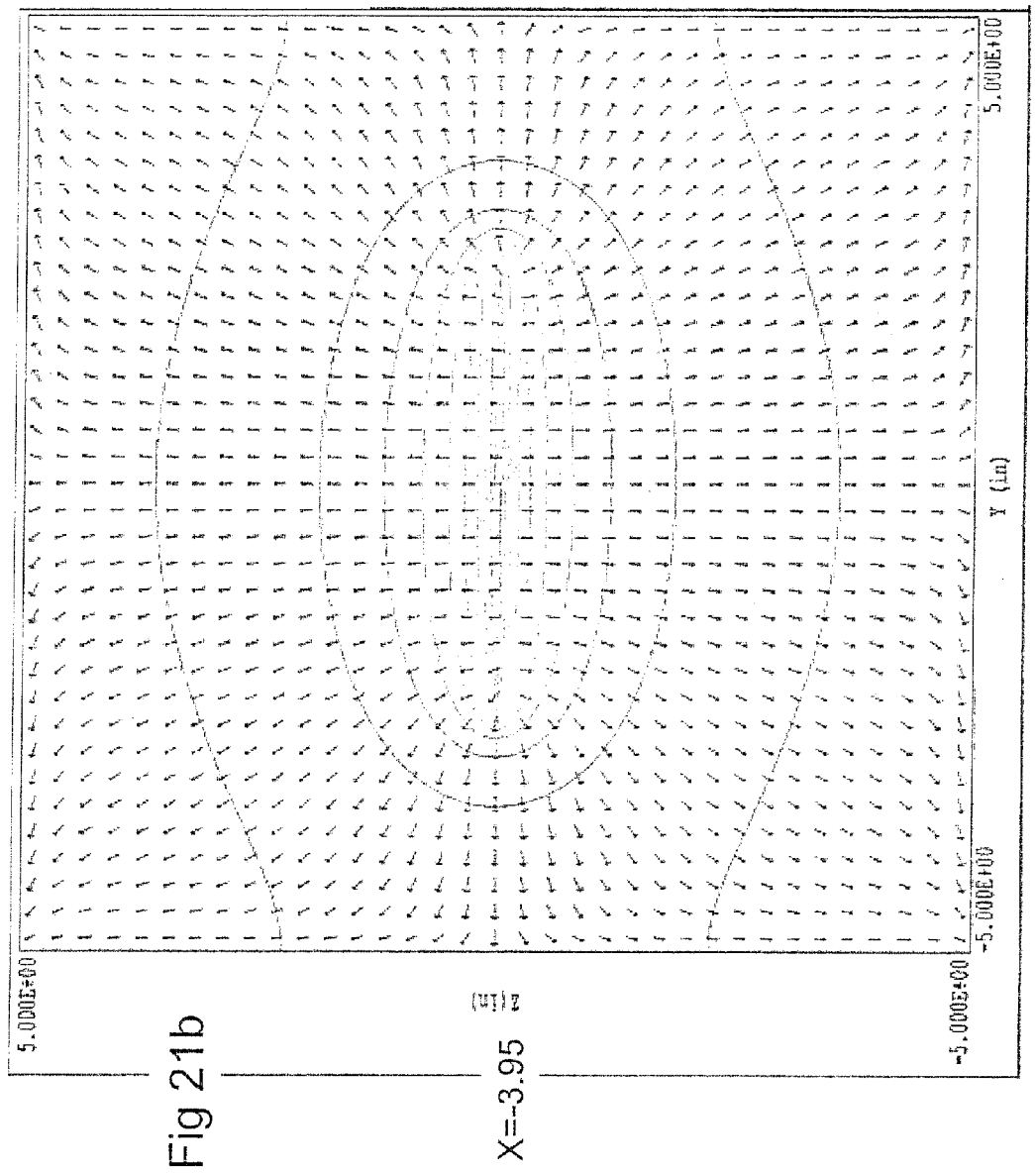

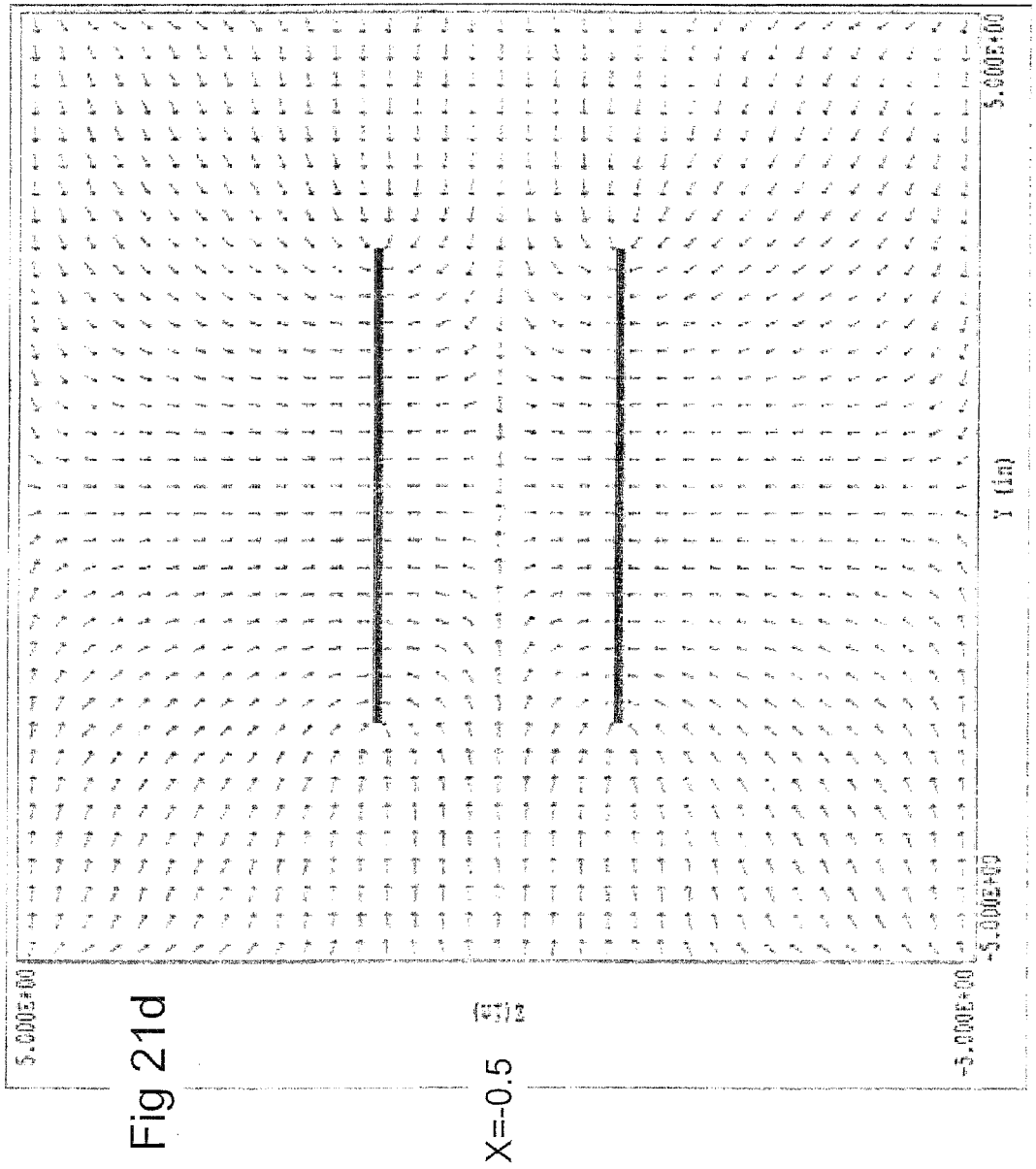

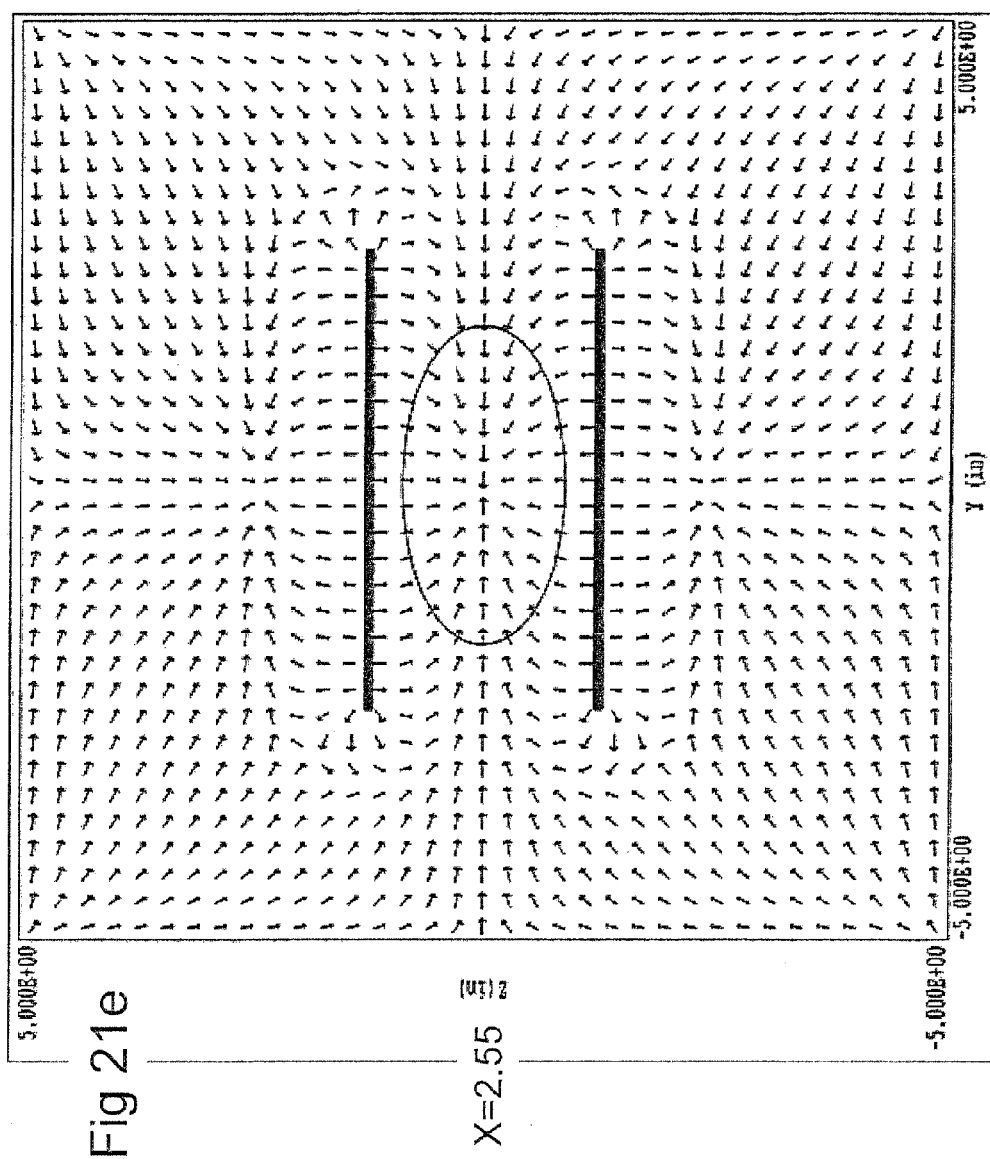

X=3.00

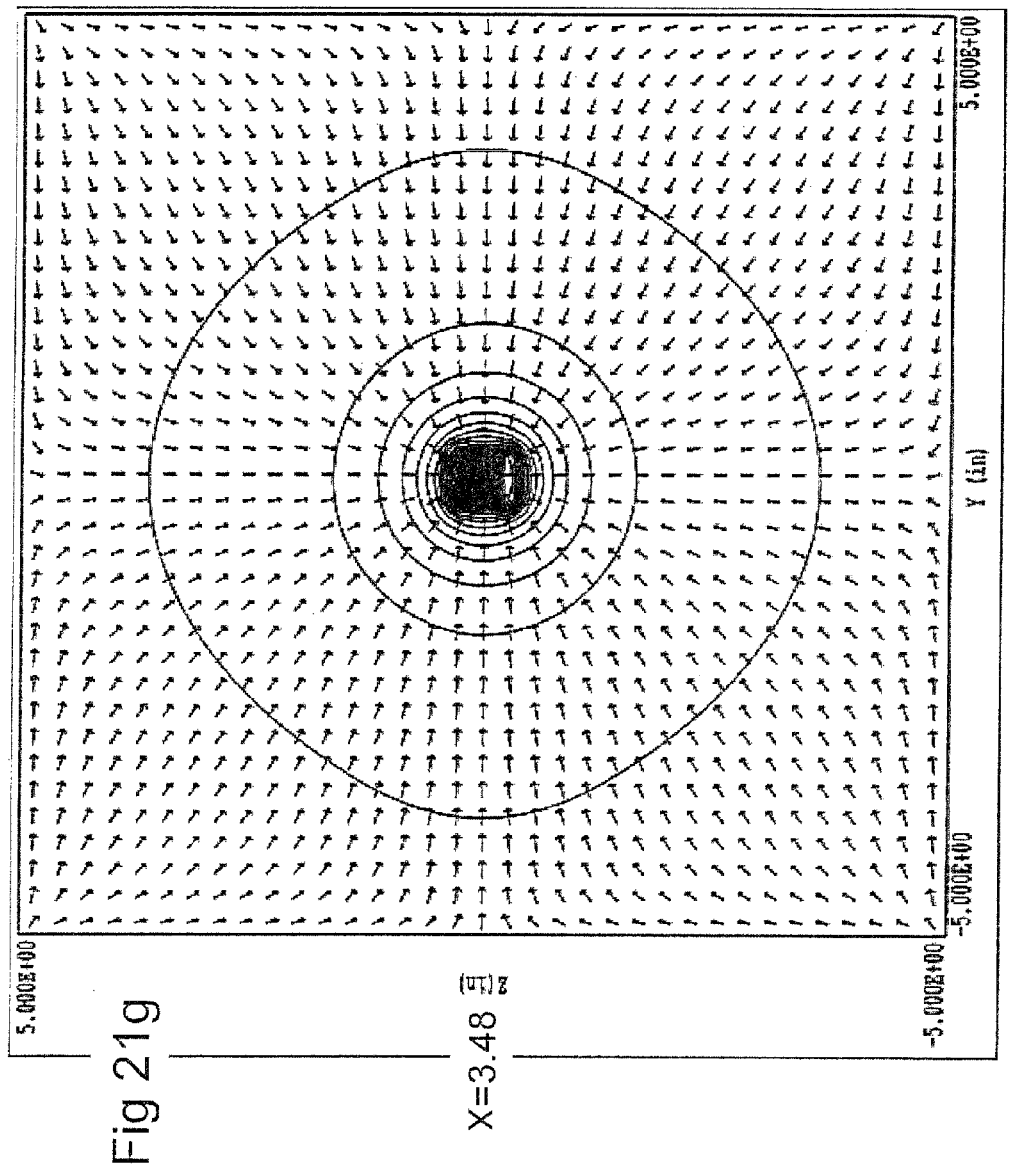

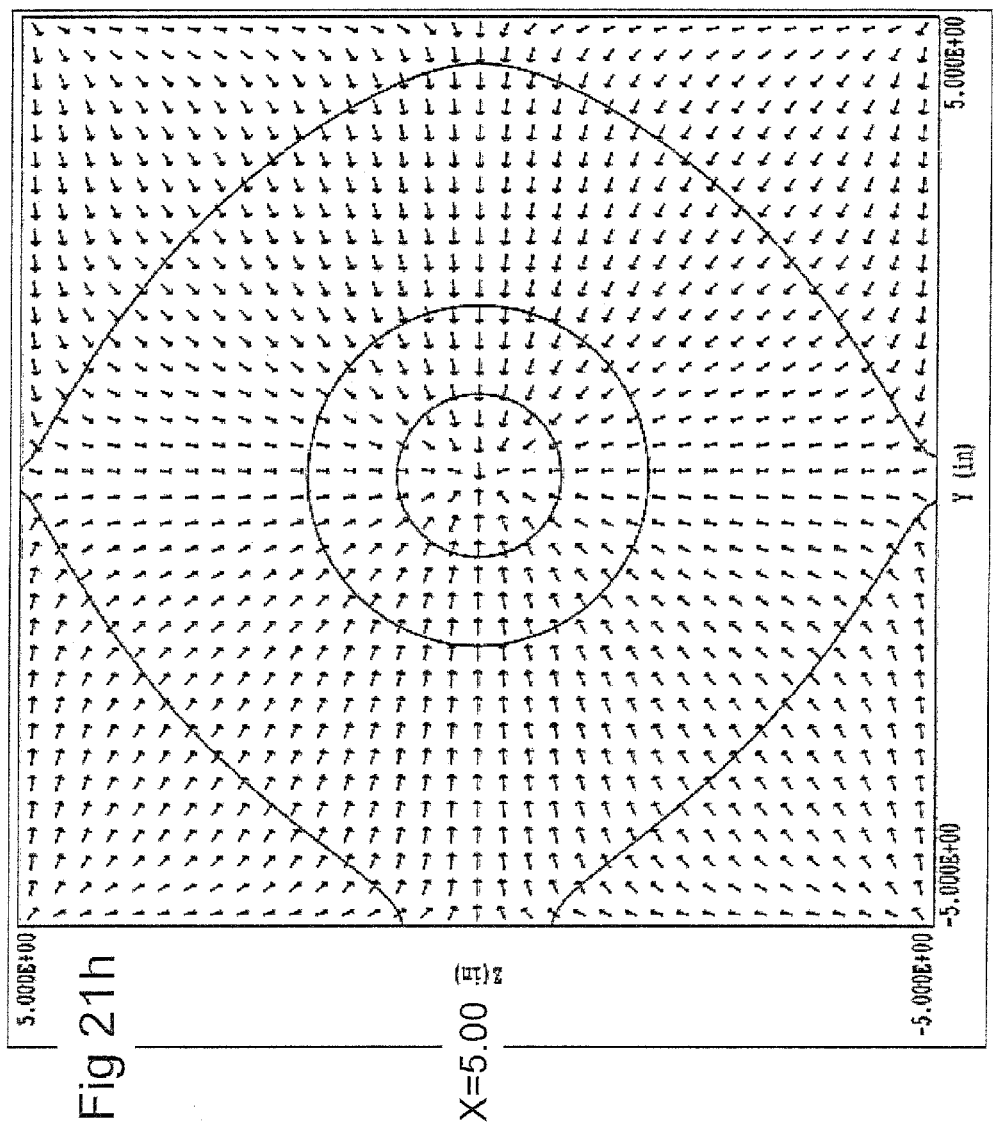

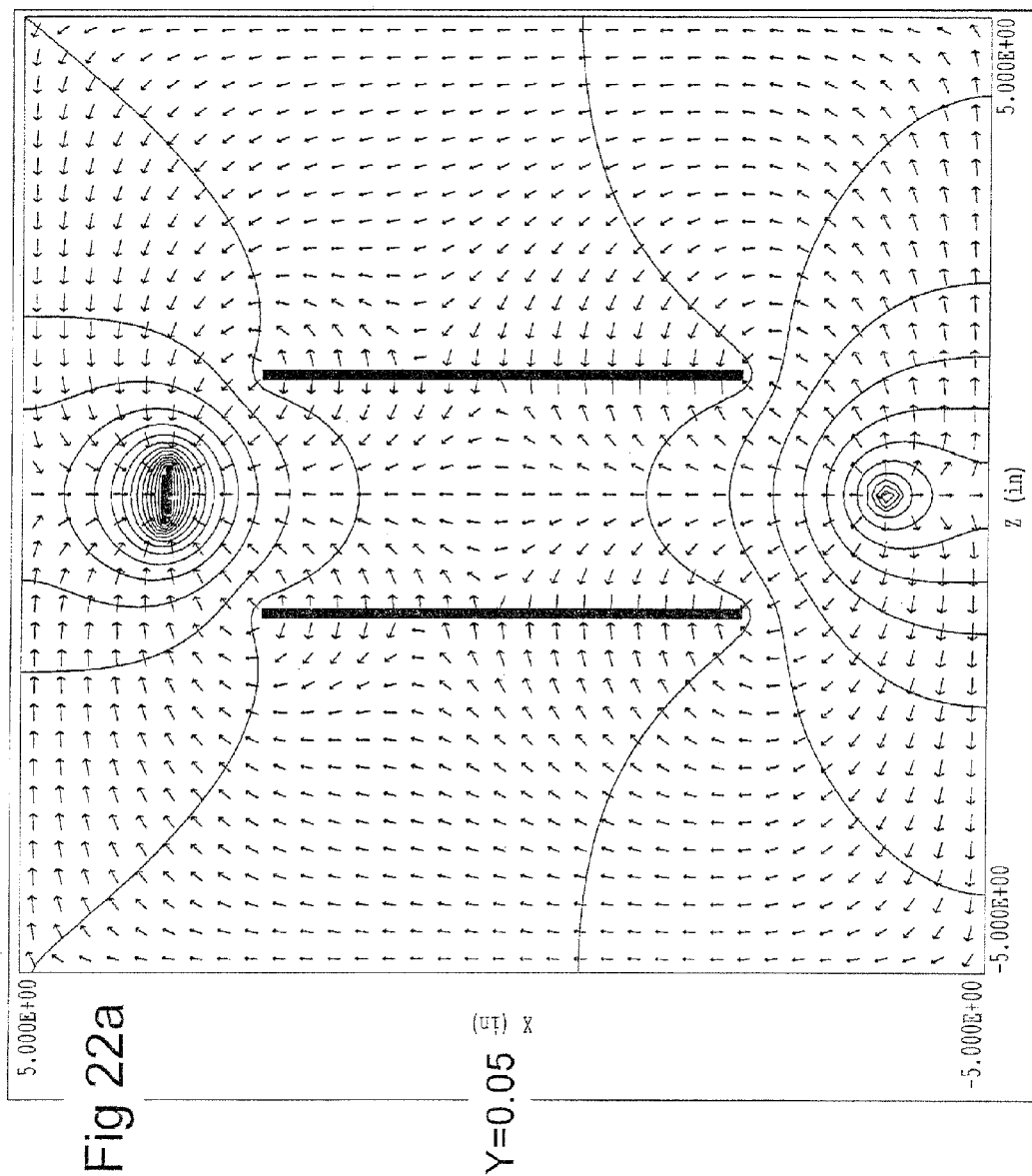

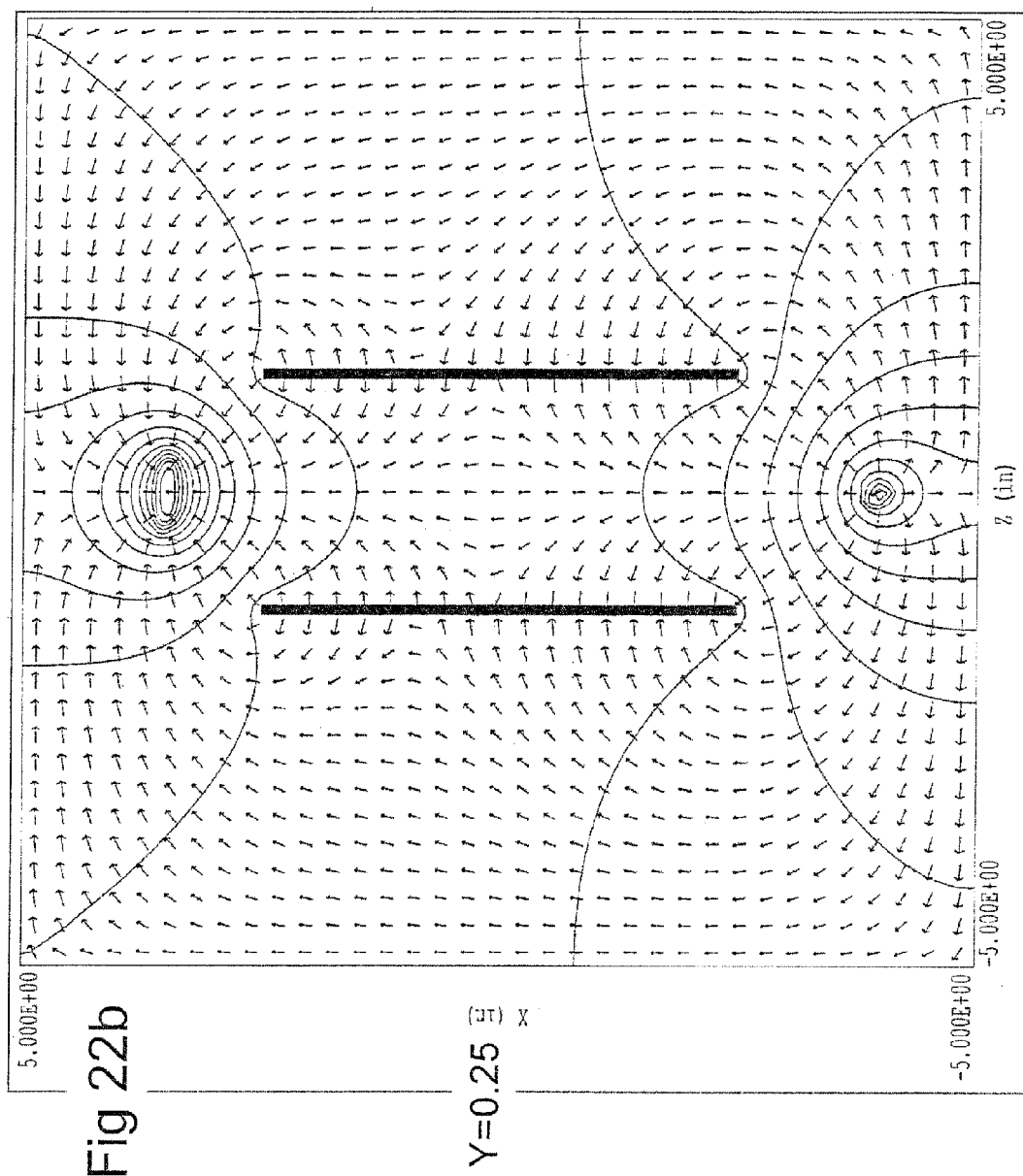

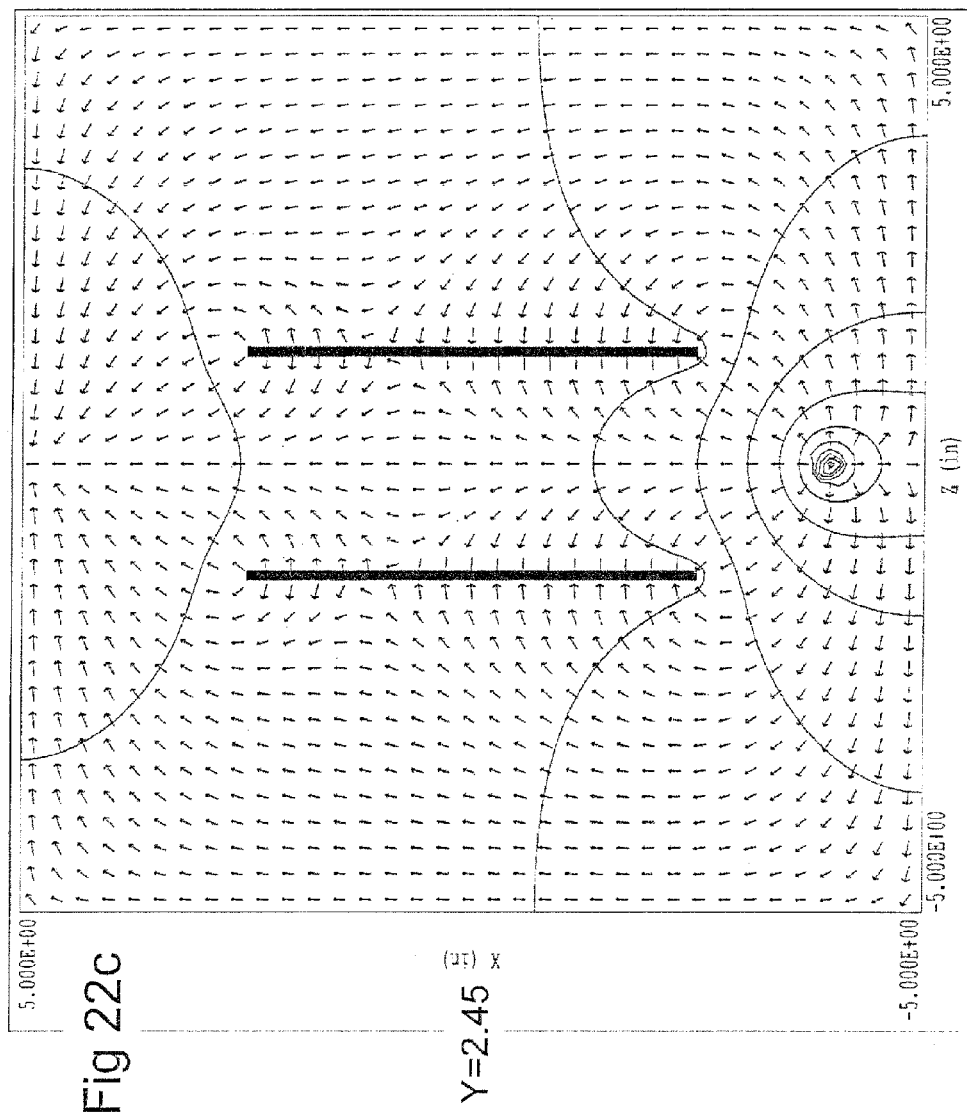

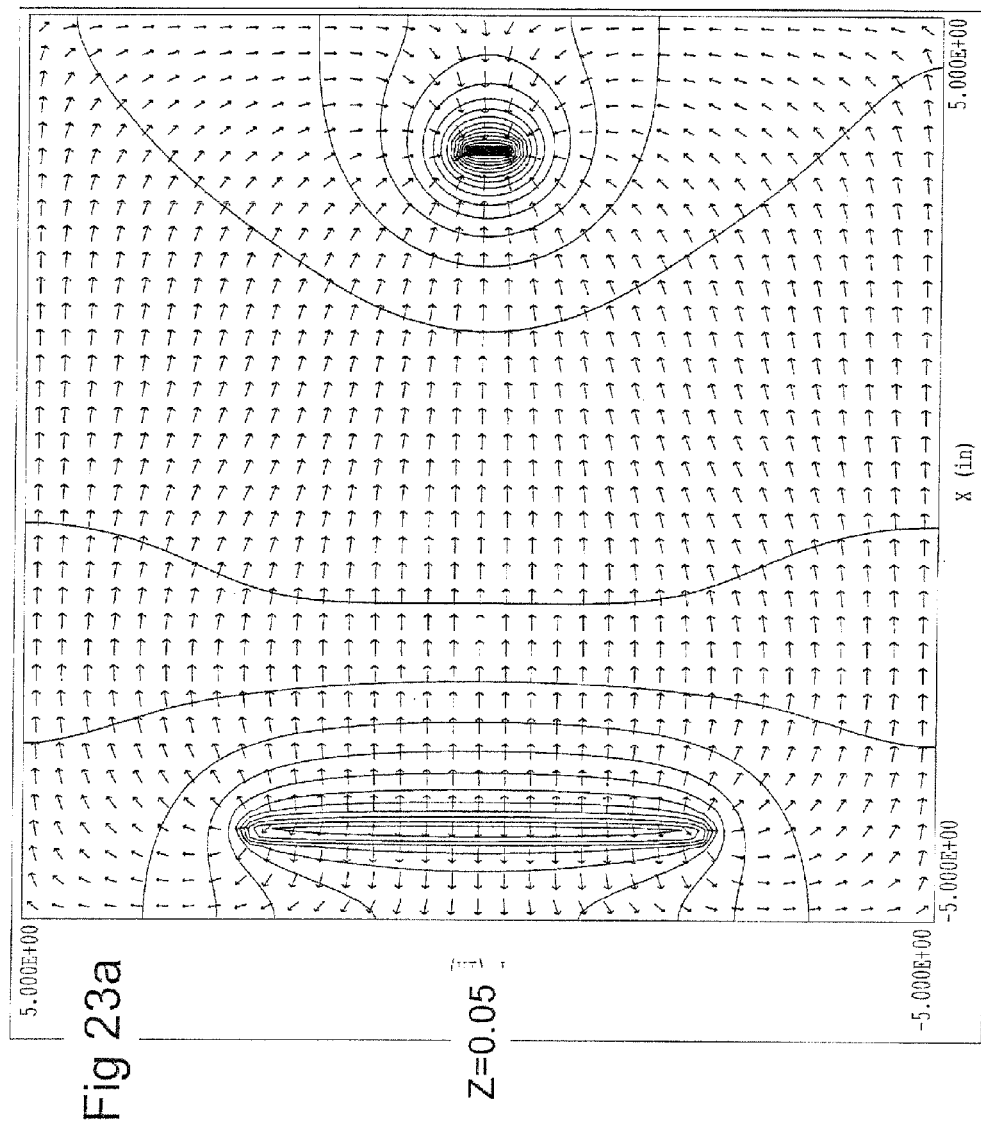

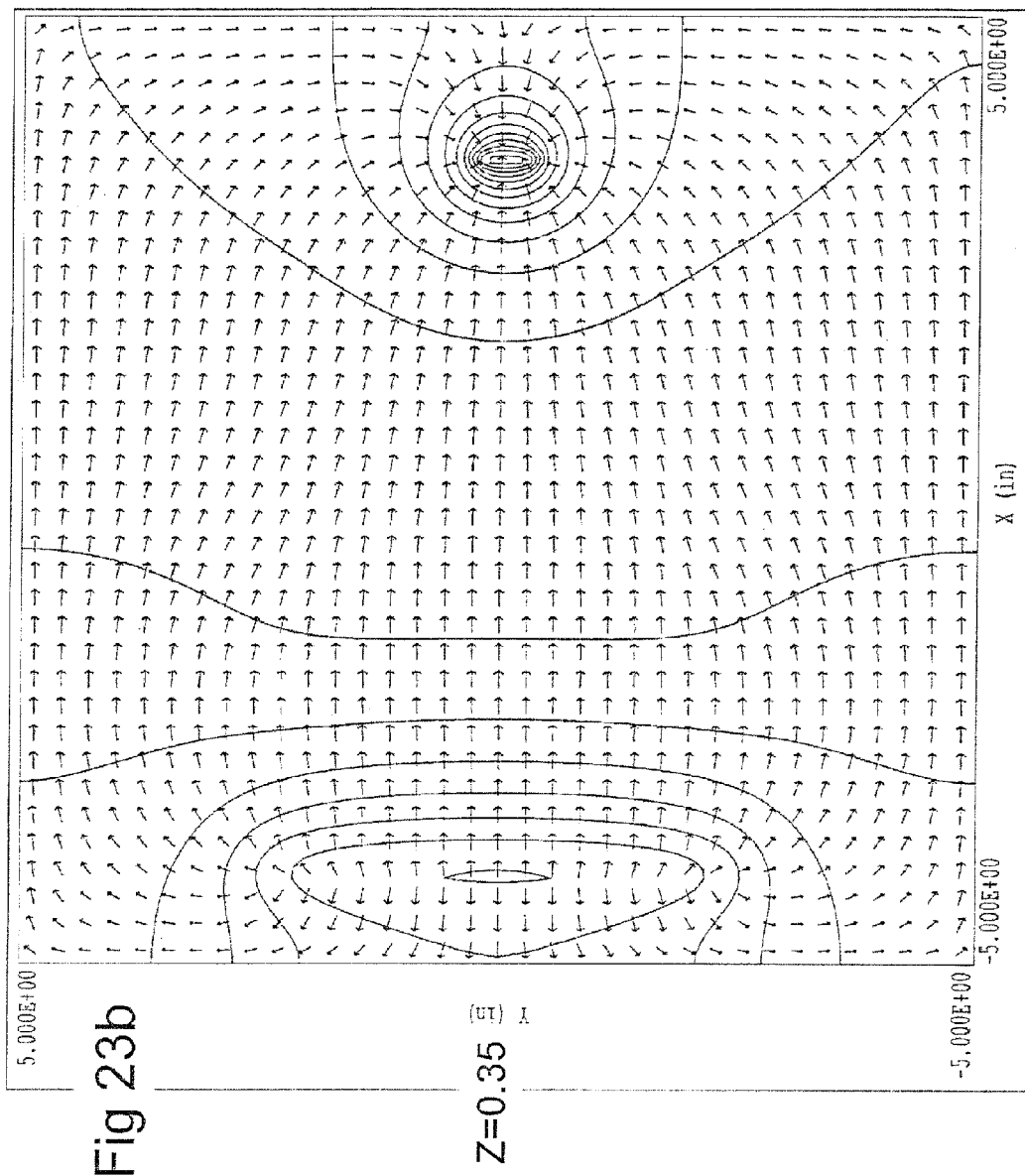

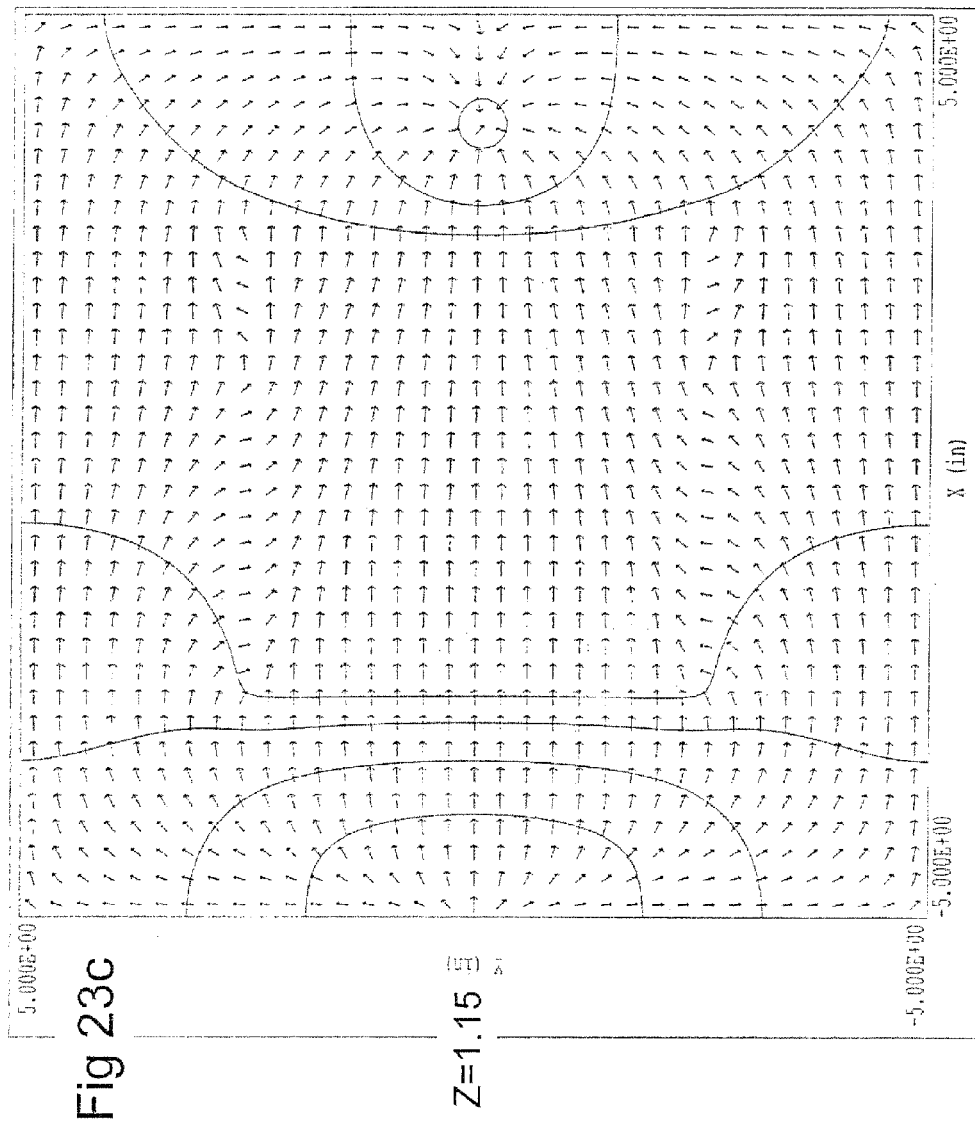

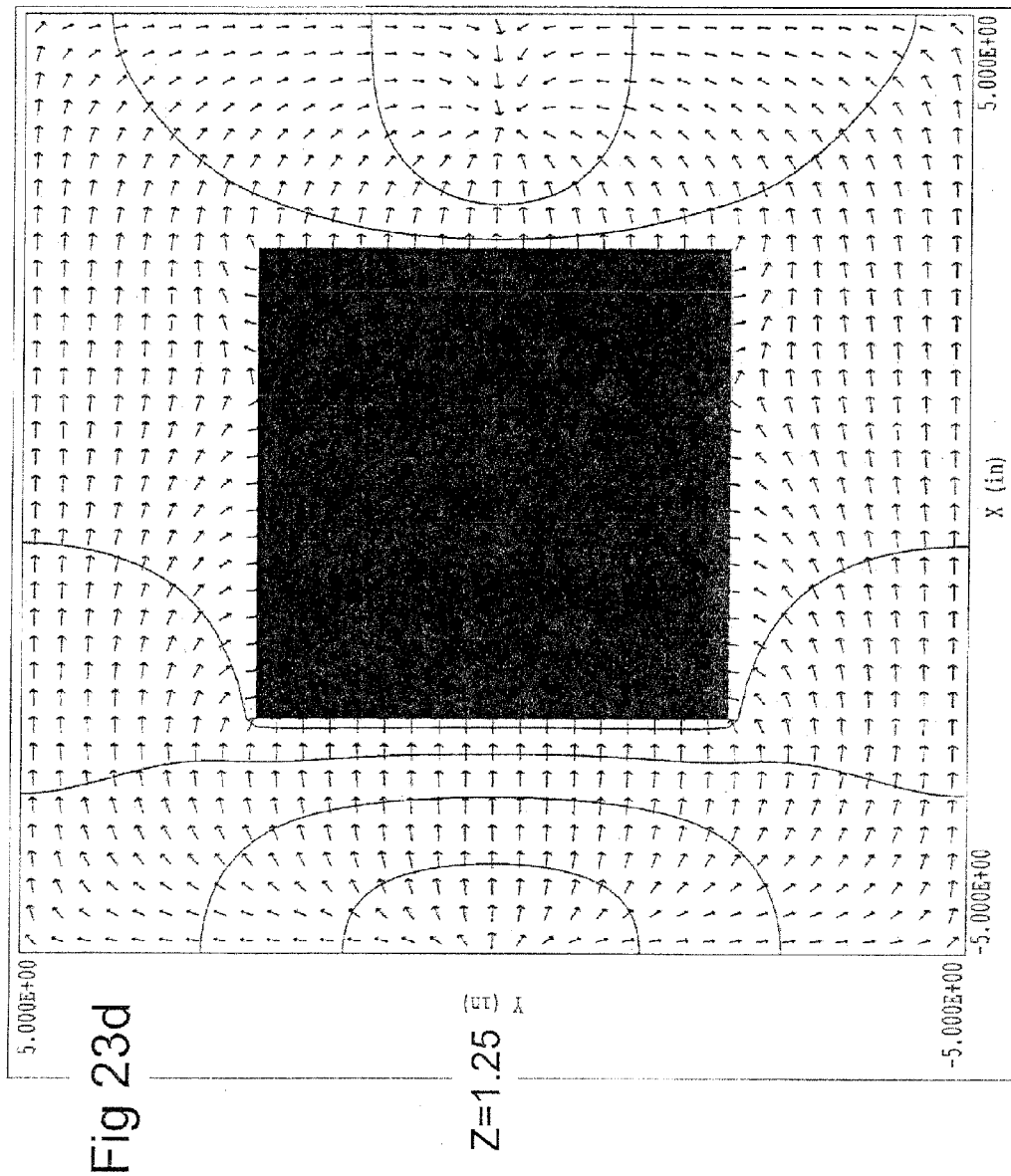

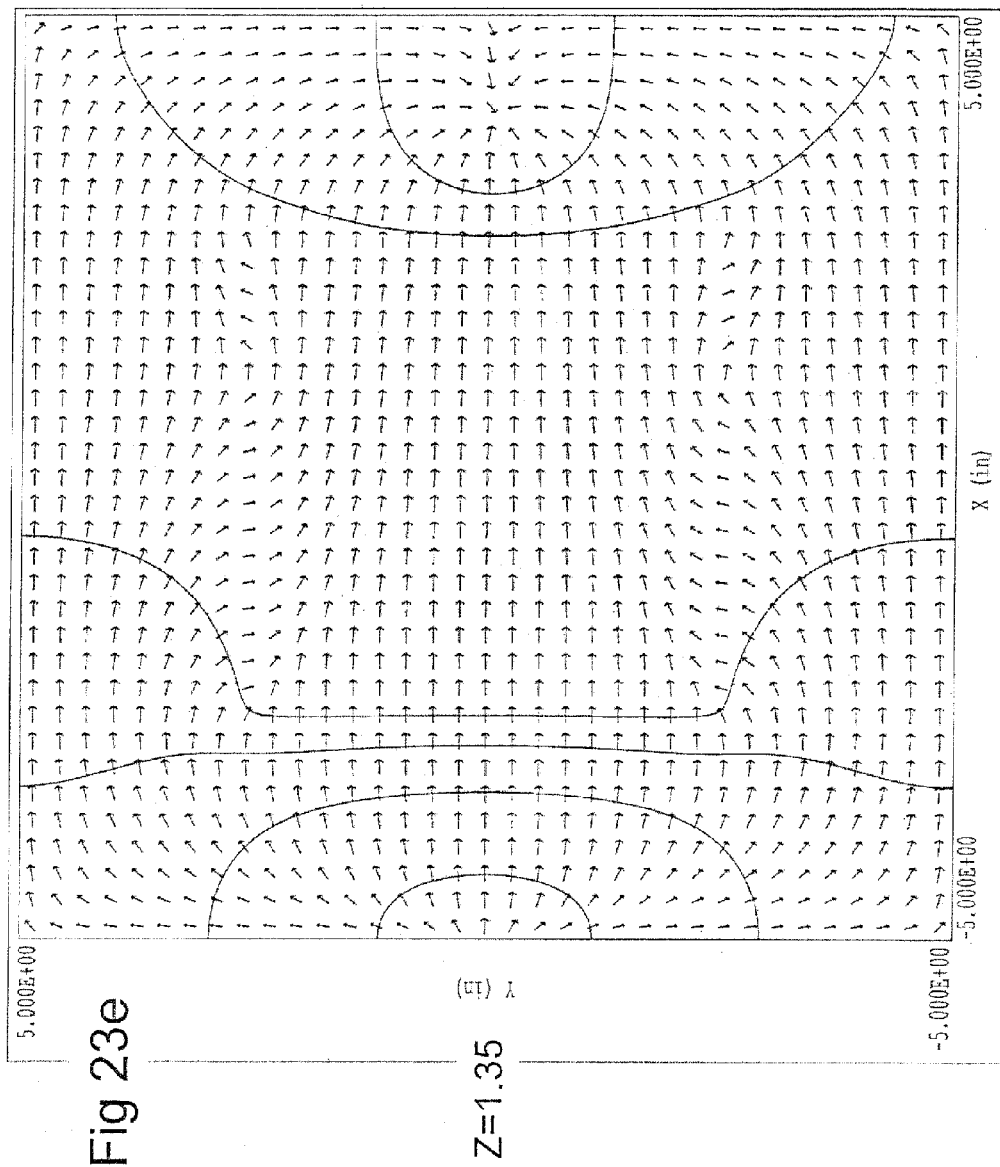

Z=5.00

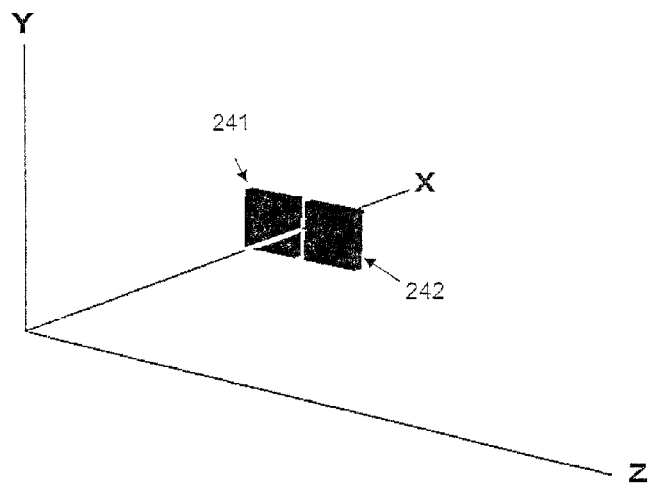
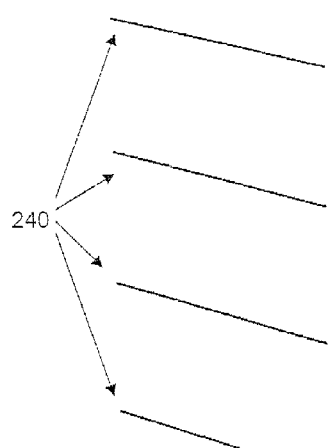
Fig 24a
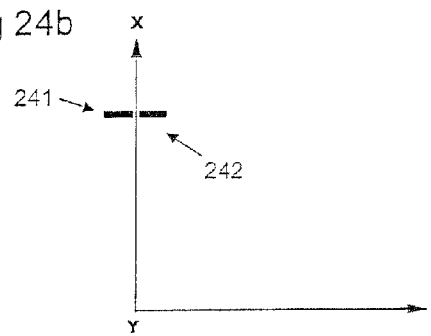
Fig 24b
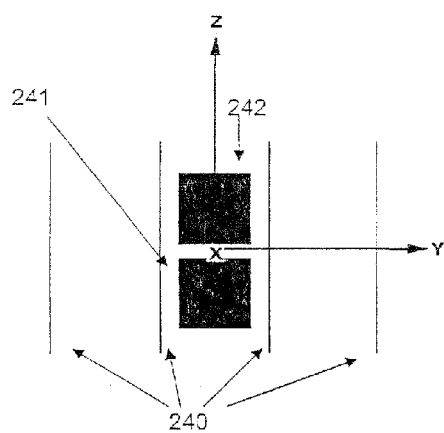
Fig 24c
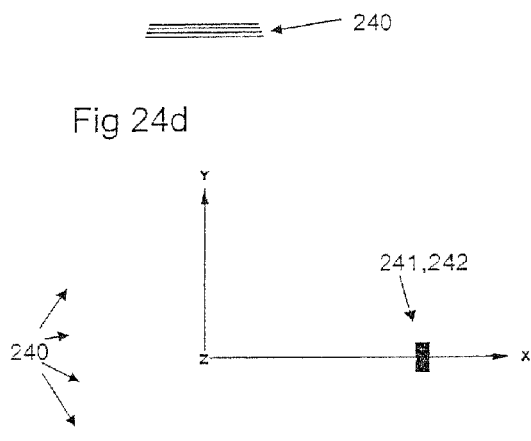
Fig 24d

ELECTROKINETIC DEVICE FOR CAPTURING ASSAYABLE AGENTS IN A DIELECTRIC FLUID

CROSS-REFERENCE TO RELATED APPLICATIONS

This application is a continuation of Gordon et al. Ser. No. 12/955,150 filed Nov. 30, 2010.

FEDERALLY SPONSORED RESEARCH OR DEVELOPMENT

Not Applicable.

MICROFICHE/COPYRIGHT REFERENCE

Not Applicable.

BACKGROUND OF THE INVENTION

1. Field of the Invention

The present invention relates to the collection of and sampling of assayable agents in a dielectric medium. This includes, but is not limited to, sampling air for agents whose presence or absence is determinable by bio-specific assays. The field includes sampling of air for biological agents, direction to, and deposition on, a collection means for an assay device. The agent-specific assays may include immunoassays, nucleic acid hybridization assays, or any other assays entailing ligand—antiligand interactions. Assays may include, but are not limited to, detection means which are colorometric, fluorescent, turbidimetric, electrochemical or voltammetric. Agents assayed include, but are not limited to, bio-warfare agents, pathogens, allergens or pollutants. Pathogens include screening for infectious airborne agents such as anthrax or tuberculosis organisms. Further dielectric media may include sampling of dielectric fluid medium such as oil for the food industry, or petrochemical and industrial oil.

2. Description of the Prior Art

In the prior art, there exist many examples of collection of agents from the air for bioassay. For example, the following publications describe various methods of allergen, pathogen and toxin collection for assay:

Yao et al (2009) in Aerosol Science volume 40, pages 492-502

Noss et al (2008) in Applied and Environmental Microbiology, volume 74, pages 5621-5627

King et al (2007) in Journal of Allergy and Clinical Immunology, volume 120, pages 1126-31

Earle et al (2007) in Journal of Allergy and Clinical Immunology, volume 119, pages 428-433

Peters et al (2007) in Journal of Urban Health: Bulletin of the New York Academy of Medicine, volume 84, pages 185-197

Yao and Mainelis (2006) in Journal of Aerosol Science, volume 37, pages 513-527

Platts-Mills et al (2005) in Journal of Allergy and Clinical Immunology, volume 116, pages 384-389

Sercombe et al (2004) in Allergy, volume 60, pages 515-520

Custis et al (2003) in Clinical and Experimental Allergy, volume 33, pages 986-991

Polzius et al (2002) in Allergy, volume 57, pages 143-145

Tsay et al (2002) in Clinical and Experimental Allergy, volume 32, pages 1596-1601.

Parvaneh et al (2000) in Allergy, volume 55, pages 1148-1154

McNerney et al (2010) in BMC infectious Diseases, volume 10, pages 161-166 and device in U.S. Pat. No. 7,384,793

Other known methods of sample collection include trapping of volatile organic compounds (VOC) on activated carbon, de-sorption and analysis by mass spectrometry. See Phillips et al (2010) in Tuberculosis, volume 90, pages 145-151 and references therein. VOC's are not considered encompassed by the present invention since the assays are strictly chemical in nature, and are not bio-specific as defined here. By bio-specific is meant assays wherein the result is determined by a biological specificity such as nucleic acid specificity, antibody specificity, receptor-ligand specificity and the like. While diagnostic specificity may be achieved by VOC analysis, this is inferred by presence and amount of groups of defined organic compounds.

The foregoing prior art publications describe "dry" methods using pumping and filtration, wiping, passive deposition, electrokinetic transport etc; usually followed by an extraction step and application of the extract to an assay.

Methods for collection in a liquid stream have been described in the patent literature:

Yuan and Lin in US Patent Application 2008/0047429A1

Saski et all in U.S. Pat. No. 6,484,594 issued in 2002.

While efficiently collecting agents from the air, such liquid streaming systems inevitably result in high dilution of the sample. There is a consequent trade-off in sensitivity unless the agents are re-concentrated.

Northrup et al in U.S. Pat. Nos. 7,705,739 and 7,633,606 describe an autonomously running system for air sampling and determination of airborne substances therein. They do not specify the exact method of air sampling, nor detail how it is transferred to an assay system.

There exist numerous commercially available systems for air purification based on filtration or electrostatic precipitation. For a general description see the Environmental Protection Agency article "Guide to Air Cleaners in the Home", U.S. EPA/OAR/ORIA/Indoor Environments Division (MC-6609J) EPA 402-F-08-004, May 2008. Numerous commercial examples of systems exist using either High Efficiency Particulate Air (HEPA) filters or electrostatic precipitation filters. Such systems are widely used for removal of particulate matter or allergens from air, including as part of domestic heating, ventilation and air conditioning (HVAC) systems. HEPA filters have the advantage of removal of particles down to the micron size range, whereas electrostatic precipitation methods have the advantage of entailing high volume flow with little or no pressure differential. See U.S. Pat. No. by Bourgeois, 3,191,362 as a detailed example for the technical specification of an electrostatic precipitation system. While efficiently removing agents from the air, such air purification systems do not lend themselves to collection of samples for analysis.

Electrokinetic-based air cleaning systems have been developed and formerly commercialized by the company Sharper Image (but now discontinued) under the trade name Ionic Breeze. The original electrokinetic principle was enunciated by Brown in U.S. Pat. No. 2,949,550. This was further improved by Lee in U.S. Pat. No. 4,789,801 for improving airflow and minimizing ozone generation. Further improvements for the commercially available system are described in U.S. Pat. Nos. by Taylor and Lee, 6,958,134; Reeves et al, 7,056,370; Botvinnik, 7,077,890; Lau et al, 7,097,695; Taylor et al, 7,311,762. In the foregoing descriptions of devices using electrokinetic propulsion, a common element is a high voltage electrode consisting of a wire. A very steep voltage gradient is generated orthogonally to the wire because of the very small cross-sectional area of the wire. The high voltage gradient causes the creation of a plasma consisting of charged particles, and kinetic energy is imparted to the charged particles by the high voltage gradient. The resulting net air flow is created by exchange of kinetic energy between charged and uncharged particles, and the net air flow is directed by the juxtaposition of planar electrodes which are at zero or opposite sign voltage to that of the wire electrode. Charged particles are electrostatically precipitated on to the planar electrodes, which may periodically be removed for cleaning. This body of work is directed toward air purification, not sample collection. However, as first described by Custis et al (2003), the Ionic Breeze device has been adapted for sample collection for allergen analysis by wiping down the electrodes with a paper tissue. The allergens were extracted from the tissue and subject to an immuno-assay. The Ionic Breeze was also used in the works of Peters et al (2007) and Platts-Mills et al (2005) for allergen collection for immunoassay analysis. Earlier, Parvaneh et al (2000) described an ionizer device with a "metal cup having a conductive surface as a collector plate", from which allergens are extracted for assay. It is not evident how the sample is collected on the inside of a metal cup and does not adhere to the entire surface. The device was made by Airpoint AB, Stockholm, Sweden. However, there is no public information concerning the manufacture or sale of such a product by Airpoint AB, there is insufficient information for one skilled in the art to be able to understand the details of the device, and no similar device was used by the same authors in subsequent publications on environmental allergen detection. There is no mention of focusing of the sample into a potential well created by a voltage gradient.

Yao et al (2009) and Yao and Mainelis (2006) have described methods for collection of bio-assayable agents on to an assay means or device. Yao and Manielis (2006) describe blocks of agar gel in electrical contact with planar electrodes, and Yao et al (2009) describe a microtiter plate interposed between planar electrodes. Both of these works describe a flow of air driven by a pump, and electrostatically precipitating the agents to be analyzed on to the assay means. The electrodes and the agar blocks have substantially the same area in these works.

McNerney et al (2010) describe a breathalyzer device, where the individual breathes or coughs into a breathing tube, the sample collects on the internal surface of a tube, is scraped with a plunger on to an optical biosensor, an immunological binding reaction is performed and the biosensor utilizes an evanescent wave illumination system to determine the presence or absence of *M. tuberculosis* by scattered light.

None of the above methods consider the use of an electric field gradient forming a potential well to focus the agents on to a collection means for an assay device.

SUMMARY OF THE INVENTION

The present invention encompasses the use of an electrode or electrodes to create a potential well that will draw charged particles out of a flowing dielectric fluid stream and focus them on to the collection means of an assay device. The potential well serves to efficiently capture the particles and enhance sensitivity by means of the focusing effect on the collection means. The flowing air stream is created either electrokinetically or mechanically. If not already electrically charged, charge is imparted to the agent to be analyzed by means of a high voltage wire electrode arrangement and consequent plasma generation; the agent is focused on to the collection means of the assay device by the potential well; and finally electrostatically precipitated thereon.

In one aspect of the invention, a device for collection of a sample from a dielectric fluid medium for a bio-specific assay device comprises an enclosure. Flow means direct fluid flow of the dielectric fluid medium in the enclosure. One or more wire electrodes in the enclosure subject dielectric fluid medium flowing in the enclosure to an ionizing plasma. Supporting means operatively associated with the enclosure support the bio-specific assay device. One or more capture electrodes are positioned proximate the supporting means to create a voltage potential well whereby charged particles thus generated within the dielectric fluid medium, or pre-existing in said dielectric fluid medium, are propelled into the supported bio-specific assay device thereby electroprecipitating the charged particles on to a sample collection region of the bio-specific assay device.

Other objects, features, and advantages of the invention will become apparent from a review of the entire specification, including the appended claims and drawings.

BRIEF DESCRIPTION OF THE DRAWINGS

FIG. 1 is a schematic cross-sectional representation of a prior art device for electrostatic precipitation as part of a HVAC system. This has been derived from technical literature from commercial suppliers;

FIG. 2 is a schematic cross-sectional representation of the Ionic Breeze prior art device, as published by Custis et al;

FIG. 3 is a cross-sectional representation of a device according to the present invention, wherein an collection means and assay device is located adjacent to a plasma stream propelled by a fan;

FIG. 4 is a cross-sectional representation of the assay device showing a detail of FIG. 3;

FIGS. 7a, b and c are various outputs from a computer simulation based on the prior art Ionic Breeze device. In this and the following FIGS. 8-19, a is the computer-aided design (CAD) input to simulation, b is the output represented by contour lines of voltage and c is the output represented as a 3-dimensional plot with voltage as the third dimension;

FIGS. 8a, b and c are similar to the simulation of the prior art device of FIGS. 7a. b and c, with a variation on the electrode geometry;

FIGS. 9a, b and c from a computer simulation of a further variation of FIGS. 7a, b and c and 8a, b and c showing a simplification of the prior art device with a reduction in the number of electrodes;

FIGS. 12a, b and c are outputs of the computer simulation of the present invention with an electrode creating a potential well downstream to the planar electrodes;

FIGS. 13a, b and c are outputs of the computer simulation of the present invention with an electrode creating a potential well adjacent to an aperture in a planar electrode;

FIGS. 15a, b and c are outputs of the computer simulation of the present invention similar to FIG. 14a, b and c, but with an assay device interposed in the potential well, the assay device having a different dielectric constant from that in FIGS. 14a, b and c;

FIGS. 16a, b and c are outputs of the computer simulation of the present invention similar to FIG. 13a, b and c, but with elements of assay device on both sides of electrode creating potential well;

FIGS. 17a, b and c are outputs of the computer simulation of the present invention similar to FIG. 10a, b and c, but additionally with an electrode creating a potential well downstream to the planar electrode;

FIGS. 18a, b and c are outputs of the computer simulation of the present invention similar to FIGS. 17a, b and c but with an assay device interposed in the potential well;

FIGS. 19a, b and c are outputs of the computer simulation of the present invention, with electrodes angled so as to enhance the air flow into the potential well;

FIGS. 20-25 are outputs of a higher level computer simulation program which models electrostatic fields in three dimensions;

FIG. 20a, b, c and d represent CAD outputs as various stereographic projections of a device according to the present invention;

FIGS. 22a, b c and d are electric field representations in successive planes along a second axis of the device of FIG. 20;

FIGS. 23a, b, c, d, e, f are electric field representations in successive planes along a third axis of the device of FIG. 20;

FIGS. 24a, b, c and d represent CAD outputs as various stereographic projections of a further device according to the present invention;

DETAILED DESCRIPTION OF THE INVENTION

Figure 5:
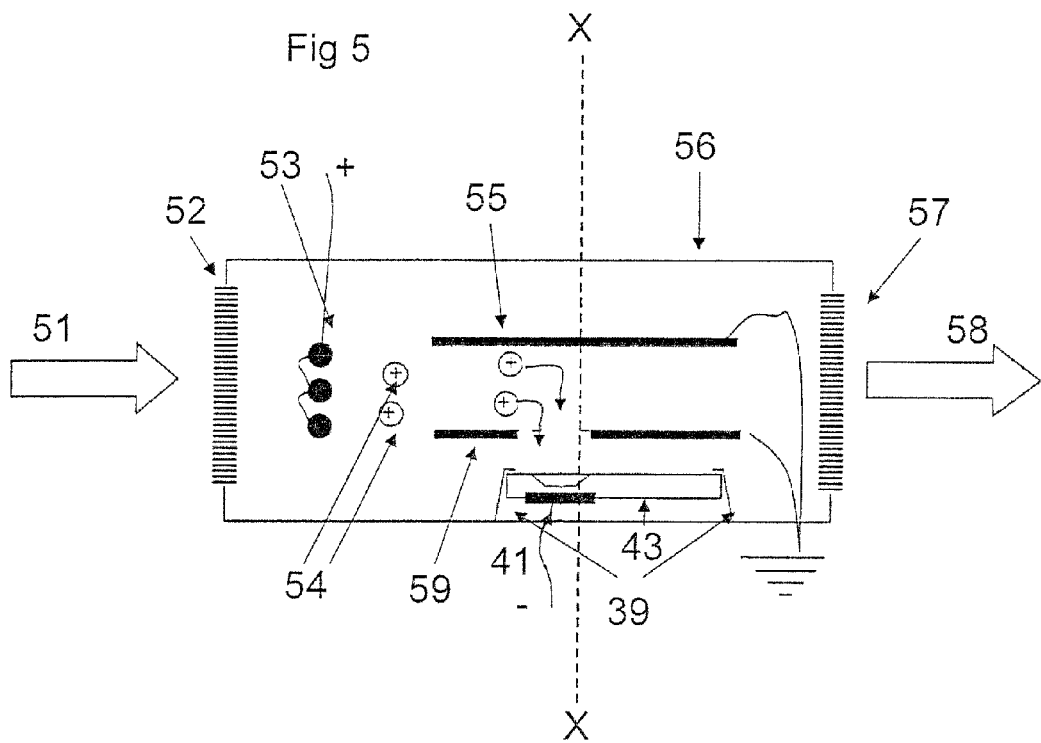
FIG. 5 is a cross-sectional representation of a device according to the present invention, wherein the flow is achieved by electrokinetic propulsion, and the collection means of the assay device is adjacent to an aperture in a planar electrode of the electrokinetic propulsion device.
Figure 6:
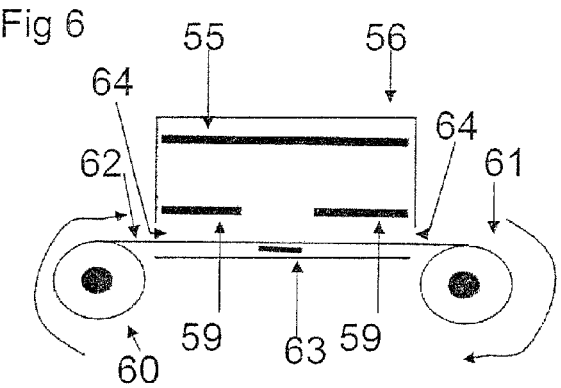
FIG. 6 represents a schematic cross section of an electrokinetic flow device wherein the assay device is a reel-to-reel collection device. The cross section of this figure corresponds to section X . . . X of FIG. 5.

In its simplest embodiment, the present invention comprises a series of wires held at high voltage in a flowing stream of air generated by a fan-like device and a collection means of the assay device exposed to the stream, and having an electrode juxtaposed so as to attract charged particles from the flowing stream. The juxtaposed electrode creates a potential well that will cause the charged particles to be electrostatically precipitated on a collection area of the assay device. Thus, FIG. 3 illustrates such a device in detail. The device comprises a non-conductive housing 35, an entrance grill 31 and exit grill 37. A pumping device, such as a fan 36, directs and pulls through a flowing airstream entering at 30 and exiting at 38. Wire electrodes 32, seen in cross-section in FIG. 3, are held at high voltage, in the range of kilovolts, and plasma generation results in charged particles 33 which are attracted out of the flowing airstream via a potential well on to a capture means 42 of the assay device 43. Assay device 43 incorporates an electrode 41 which is shown to be grounded with the common electrical symbol for grounding. The assay device 43 is removably supported and clamped in an indented aperture 39 in the housing 35. For clarity, the assay device 43 is separately illustrated in FIG. 4. Thus, to perform an assay, the assay device is clamped in aperture 39 in the housing 35 of the electrokinetic device of the present invention, exposed to a predetermined voltage, flow rate and time, then removed.

One form of assay would be a lateral flow immunochromatographic device, in which case the assay is initiated by application of a suitable chromatographic transport facilitating fluid to the sample well 42 and reading the result after a predetermined time. Numerous other simple assay systems can also be used, involving optical or electrochemical detection and determination of the presence or absence or amount of the agent to be assayed. Since the device of the present invention performs in a dielectric medium, conductive aqueous fluids would normally need to be added to the various assay types to initiate a detection reaction.

The understanding of the present invention is facilitated by the illustrations of prior art devices. Further, because the present invention can be fabricated by simple modifications of prior art devices, figures including drawings of several prior art devices have been included. FIG. 1 has been derived from various technical specifications of HVAC systems for domestic housing. Air flow is driven by a fan16, provide inlet flow 11 and outlet flow 18, entering via a grill 12, a coarse pre-filter 13 and the high voltage wire electrodes, grounded electrodes 15, upon which charged particles are electrostatically precipitated, and exit grill 17. Prefilters are not normally required in the function of the present invention.

In a further embodiment of the present invention, FIG. 5 shows a device with the flow of the dielectric fluid propelled by electrokinetic means. The device consists of a non-conductive housing 56, and entrance grills and exits grills 52 and 57, respectively, for the inflowing and outflowing dielectric fluid, 51 and 58, respectively. Wires 53, seen in cross section in FIG. 5, are maintained at a positive high voltage, and electrokinetic flow is directed by grounded planar electrodes 55 and 59. An aperture exists in the electrode 59, below which is located a collection means and assay device, removeably supported in clamps 39 in the housing 56. As in FIG. 4, the collection means incorporates an electrode 41 which is small in dimensions compared with the grounded planar electrodes 59. The electrode 41 in this case is held at a high negative voltage in the kilovolt range. The planar electrodes 55 and 59 cause the charged particles 54 to be first transported with the net fluid flow, but when they reach the potential well created by the negative electrode 41, they are diverted from the stream on to the collection area of the collection means 43. Thus, to perform an assay, the assay device is placed in a suitable aperture 39 in the housing 56 of the electrokinetic device of the present invention, exposed to predetermined voltages of the wires 53 and the electrode 41 and predetermined time, then removed. One form of assay would be a lateral flow immunochromatographic device, in which case the assay is initiated by application of a suitable chromatographic transport facilitating fluid to the sample well 42 and reading the result after a predetermined time. Numerous other simple assay systems can also be used, involving optical or electrochemical detection and determination of the agent to be assayed. Since the device of the present invention performs in a dielectric medium, conductive aqueous fluids would normally need to be added to the various assay types to initiate a detection reaction.

In another embodiment of the present invention, an alternative means of sample collection may be used to create a continuous record of the agent to be analyzed. FIG. 6 illustrates such an embodiment. The device of FIG. 6 is comparable to the device of FIG. 5 in all respects except for the omission of the assay device and replacement by a reel-to-reel sample collection means. The reel to reel device supports and moves the sample collection means orthogonally to the net flow of the dielectric fluid. Accordingly, the illustration of FIG. 6 represents a section X . . . X through the device of FIG. 5. The reels 61 and 62 rotate in the directions indicated by arrows, transporting the sample collection means, 62, through slots 64 in the housing 56. An electrode 63, mounted in the housing, is held at a negative voltage in the kilovolt range. Similarly to FIG. 5, charged particles will be swept out of the flowing stream by the potential well created by electrode 53, and deposited on the sample collection means 62. Thus, to perform an assay, the wire electrode 53 and the electrode 63, whose area is small compared with the grounded planar electrodes 59, are set at predetermined voltages and the reel-to-reel transport device moves the sample collection means for a predetermined time. The sample collection device material may include a passive fibrous or membranous material, or an activated material that will capture the sample in place until the time of assay; or may be a structured material such as micro-pillar type, and may have embedded capture molecules, such as provide ligand-anti-ligand reactions. Upon completion of the predetermined time, the take-up reel 61 is removed and subject to hydration prior to assay, in such a way that the captured agent to be analyzed remains positioned on the capture means, either by active or passive immobilization, or by capture via a ligand-anti-ligand interaction. The assay is performed and the disposition of values along the length of the capture means provides a time record of the presence or amount of the agent measured. The continuous record may be colorimetric, in which case the record is a visual display of the presence or amount of the agent as a function of time. The continuous record may also be digital, in which the record can be presented as a graphic representation of the amount or presence of the agent as a function of time.

FIG. 2 is reproduced from the publication of Custis et al (2003). The prior art device of FIG. 2 comprises a housing 24, electrokinetically driven air flow entering at 20 and exiting at 25, wire electrodes 21, and planar electrodes 23. Conjectural lines of constant voltage (voltage contours) are shown as broken circles surrounding the electrodes 21, and conjectural particle movement in the airstream by arrows 22. This illustrates the particles impinging on and being electrostatically precipitated on the planar electrodes, 23, which are removable. Samples for analysis are collected by wiping from the planar electrodes with tissue, extraction and application of the extract to an immunoassay, according to the procedure of Custis et al. The advantage of the present invention is that such separate wiping and extraction steps are not required. Further, while the contour lines of equal voltage in the prior art of Custis et al are conjectural, computer simulations are available which facilitate the design of the devices of the current invention without undue experimentation. Brown in FIG. 2 of U.S. Pat. No. 2,949,550 also drew conjectural lines of voltage gradient. The voltage gradient will determine the force and direction experienced by a charged particle. Voltage gradients can be rigorously determined by computer simulation, eliminating undue experimentation.

The computer simulation of the devices of the present invention are performed with the use of a software package provided by the company Field Precision LLC, PO Box 13595, Albuquerque, N. Mex. 87192, U.S.A. This software provided by Field Precisions LLC utilizes finite element analysis based on Coulomb's Law and Gauss's Law. The work is described in "Field Solutions on Computers" (ISBN 0-8493-1668-5), author Stanley Humphries, published by CRC press. Description of the software and the conditions for purchase are provided by Field Precisions LLC. The version used here is the free students version, comprising the program Mesh65 to design devices and EStat 6.0 to generate the output. The drawings of FIG. 7a, b, and c to FIG. 19 a, b and c are generated with this software package. FIGS. 20a, b, c and d to 25a and b are generated with the more advanced 3-dimensional programs, Geometer, Metamesh, HiPhi and PhiView. U.S. EPA/OAR/ORIA/Indoor Environments Division (MC-6609J) EPA 402-F-08-004, May 2008

For further illustration of the use of the computer simulation, and to demonstrate how the present invention differs from the prior art, representations of prior art devices and arrangements are shown in FIG. 7a, b and c to FIG. 11a, b and c. For better understanding of the application of the software package, a detailed description of the process is given for FIG. 7a, b and c. A representation of the Ionic Breeze configuration (FIG. 2) is created in the Mesh program in FIG. 7a. A bounding box of 4 units×4 units is defined, and within this box are placed two points, 70, which represent the wire electrodes, and three lines, 71, which represent the planar electrodes. The symmetry is defined as planar. This determines that all cross sections are equivalent extending in the third dimension out of the plane. This version of the software performs the computation in two dimensions, thus simplifying the calculations. The Mesh program saves the file in a CAD format (suffix .DXF) and also converts to a script which is recognized by the EStat program (suffix .MOU). The EStat then provides for the addition of dimensions (units=inches), material properties such as dielectric constants (1 for air), and voltages (1000 for wire electrodes, 0 for planar electrodes). With these parameters, a new file (suffix .EIN) is created. The mathematical solution of the simulation is then performed on the .EIN file, creating a file with the solution (suffix .EOU). Various graphical representations of the solution of the .EOU file are then available. FIG. 7b shows the contour plot output, with contour lines, lines of equal voltage, given a numerical value label according to the voltage. FIG. 7c shows the surface plot format. Here perspective drawing is used to express the voltage as a height in the third dimension. The surface plot representation is particularly useful as the steepness and direction of the slope in the surface represents voltage gradient and direction. Thus, the surface plot represents the force and direction vector to which a charged particle is subject. It is immediately apparent from FIG. 7c that charged particles generated at the wire electrodes, or pre-existing in the air, will be propelled down the gradient into the three valleys and directed on to the surfaces of the planar electrodes.

Figure 21A:
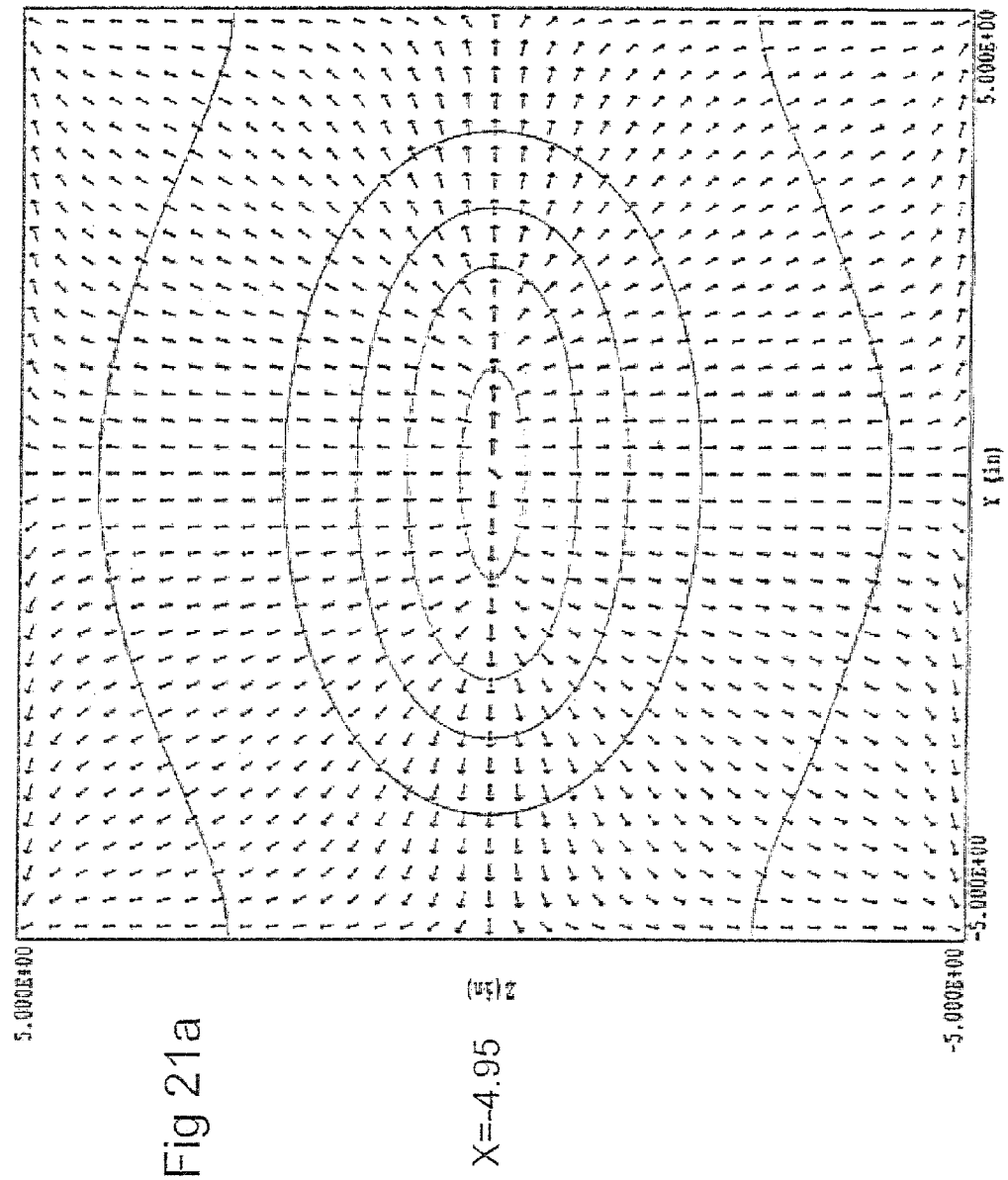
FIGS. 21a, b, c, d, e, f, g and h are electric field representations in successive planes proceeding along one axis of the device of FIG. 20.

The various configurations in the remaining FIG. 8a, b, and c to FIG. 21a, b and c are all generated in this way.

For the establishment of design concepts for the present invention, the effect of the thickness of the planar electrodes is shown in FIGS. 8a, b and c. In FIGS. 7a, b and c the planar electrodes are represented as having zero thickness, whereas in FIGS. 8a, b and c they are represented as plates with a finite thickness of 1/20". In all other respects, these two sets of figures are identical. It can be readily seen that altering from an infinitely thin electrode to one that has finite and practical thickness has no impact on the resulting voltage gradients. The family of U.S. Pat. Nos. 7,056,370, 7,097,695 and 7,311,762 teach the improvement of reduction of thickness of the electrodes over the prior art, U.S. Pat. No. 4,789,801. However, further reduction of thickness has no benefit for the current invention.

Figure 10C:
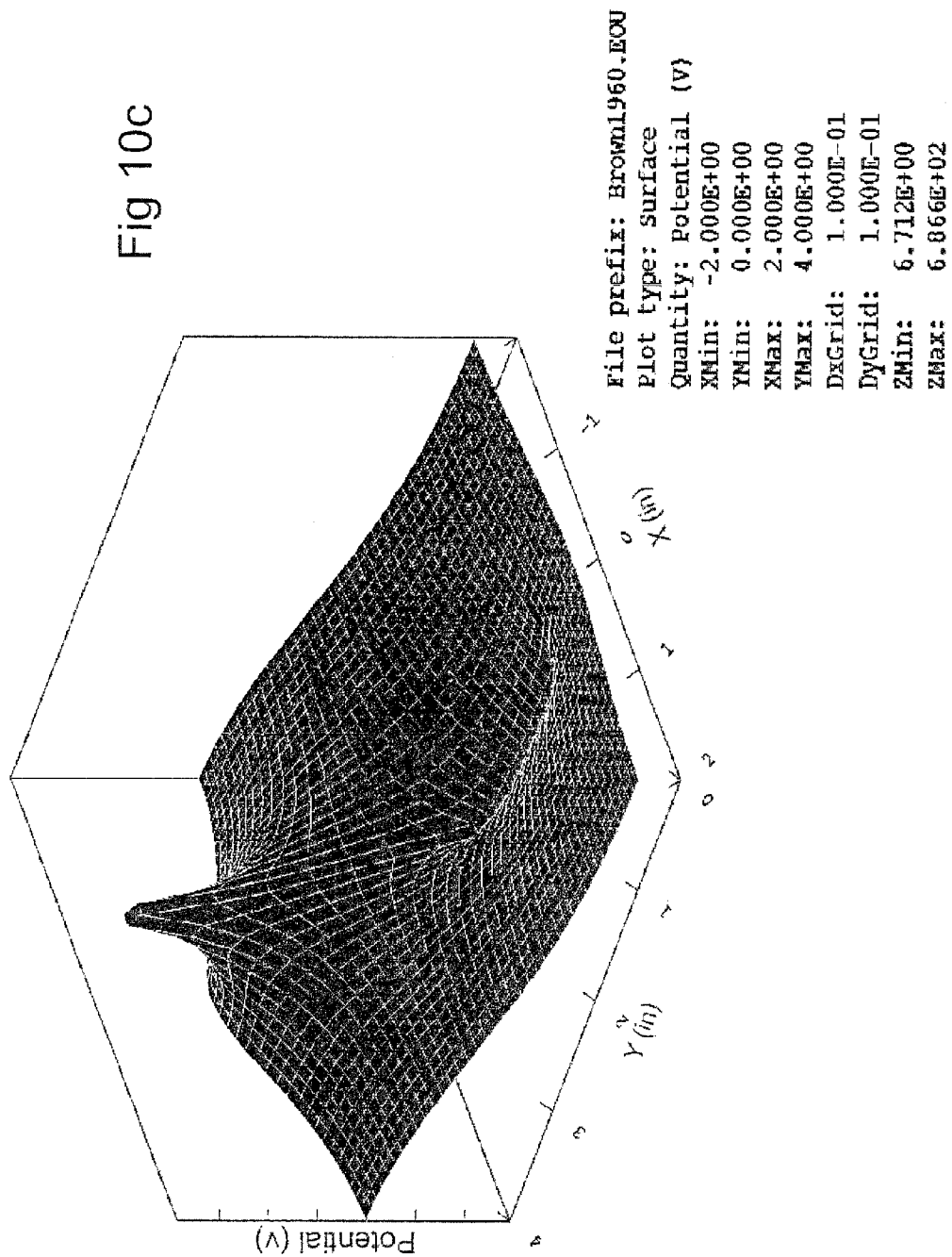
FIGS. 10a, b and c are outputs from the computer simulation of the foregoing figures showing a further simplification and being representative of the prior art device in U.S. Pat. No. 2,949,550.

For the purposes of the present invention, a somewhat simpler arrangement of electrodes would be advantageous for facilitating the placement of a third electrode creating a potential well for the capture of the assayable agent on to the collection means of the assay device. Accordingly, the computer simulations in FIGS. 9a, b and c and 10a, b and c show the effect of successive reduction in the number of electrodes. FIG. 9a shows one high voltage wire electrode 90 and two plate electrodes at 0 voltage, 91. The contour plot FIG. 9b and the surface plot FIG. 9c show charged particles generated as plasma at the wire electrode 90, or pre-existing in the air, will be propelled down the gradient into the two valleys and directed on to the surfaces of the planar electrodes. Similarly, FIG. 10a shows a design with a single high voltage wire electrode, 100 and a single plate electrode at zero voltage, 101. The physical arrangement of FIG. 10a corresponds to the original electrokinetic design of Brown in U.S. Pat. No. 2,949,550. The contour plot FIG. 10b and the surface plot FIG. 10c show charged particles generated as plasma at the wire electrode 100, or pre-existing in the air, will be propelled down the gradient into the valleys and directed on to the surfaces of the planar electrode.

Figure 11B:
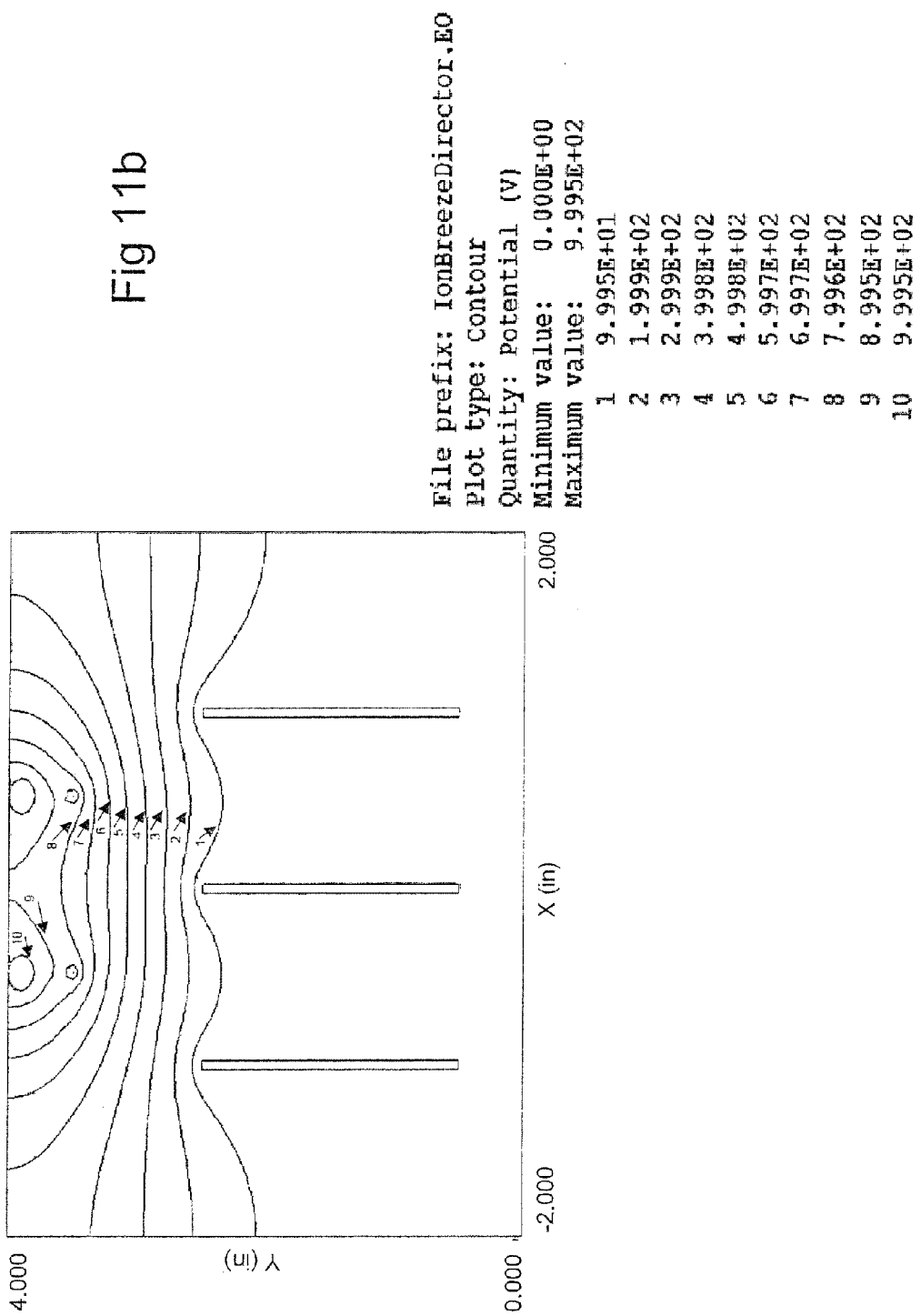
FIGS. 11a, b and c are outputs from the computer simulation of a prior are device corresponding to that of FIGS. 7a, b and c with the juxtaposition of additional electrodes upstream, as described in U.S. Pat. No. 6,958,134.
Figure 11C:
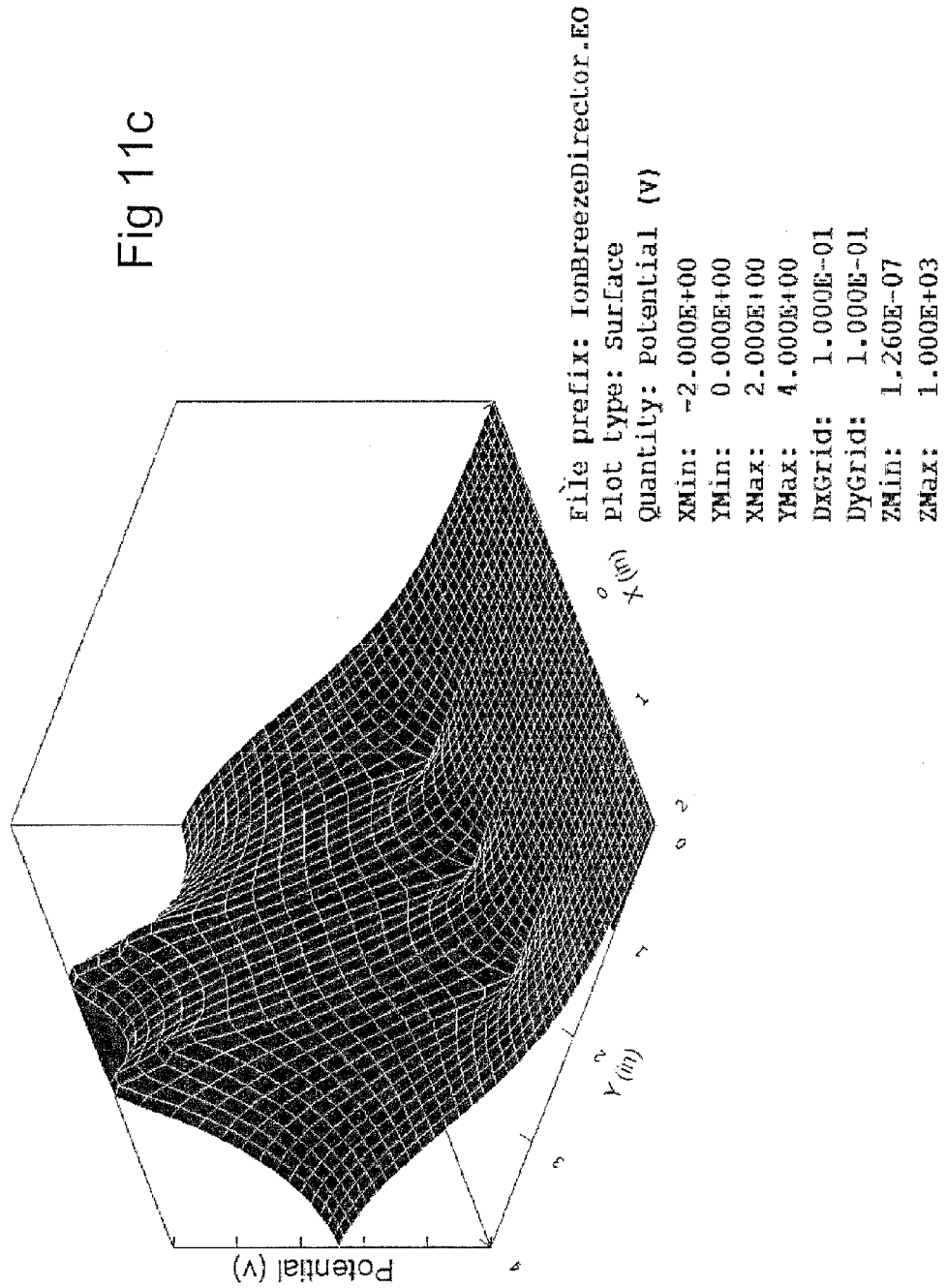

The design of FIG. 11a is identical with the design of FIG. 8a except for the addition of two rod electrodes, 112, of 0.2 inches diameter and disposed upstream of the wire electrodes 110 and the plate electrodes 111. The electrodes 112 are held at 1000 volts, as are the wire electrodes 110. The plots of FIGS. 11b and 11c show that the steepness of the voltage gradient is compromised by the presence of the rod electrodes 112, and the generation of plasma and electrokinetic propulsion would be reduced, although charges particles would still be directed into the potential valleys adjacent to the planar electrodes 111. It is to be emphasized that no focusing effect, in the sense used in the current invention, is created. It is to be noted that Taylor and Lee in the U.S. Pat. No. 6,958,134, teach that the placement of upstream electrodes serves to assist in the control of the flow of ionized particle. Nowhere do Taylor and Lee teach the use of an electrode of small dimensions compared with the planar electrode as a means of creating a potential well to capture charged particles from a flowing fluid stream. FIG. 11a, b and c shows that the focusing effect taught by Taylor and Lee is distinct from the focusing as used in the present invention, as will be made clear from the embodiments of the present invention, which follow.

One embodiment of the present invention is shown in FIG. 12a. This consists of two wire electrodes 120, three plate electrodes, 121 and a capture electrode, 123. This is comparable to the prior art device of FIG. 7a, b and c, but with the addition of capture electrode 123, according to the present invention. Electrodes 120 are at 1000 volts, the plates 121 at 0 volts and the capture electrode 123 is at −1000 volts. The contour plot of FIG. 12b and the surface plot of FIG. 12c show that electrokinetically driven charged particles generated by the plasma at the wire electrodes 120 will be driven to the potential valleys in the neighborhood of the plate electrodes 121, but these valleys are downward sloping as is clear in the surface plot of FIG. 12c. Consequently, the flow of charged particles will be propelled in the direction of the capture electrode 123, and eventually will be trapped in the potential well created by the capture electrode 123. Note that the downward slope of the valleys in the neighborhood of the planar electrodes 121 is less apparent in the contour plot FIG. 12b than in the surface plot FIG. 12c. This is because the plot interval is adjusted for clarity by the simulation program.

A more preferred embodiment of the current invention I illustrated in FIG. 13a, b and c. The electrode arrangement is based on the prior art device of FIGS. 9a, b and c, with the following modifications according to the present invention. The electrode 132 is fabricated with a slot 134, and juxtaposed with dimensions comparable to the slot 134 is the capture electrode 133. See also the electrode arrangement of FIG. 5. This arrangement of creating a potential well off-set laterally to the main electrokinetic fluid flow, may, in certain designs according to the present invention, be more convenient for the insertion of a capture means and assay device than directly in the fluid stream. In spite of this off-set arrangement, the contour plot of FIG. 13b and the surface plot of FIG. 13c show the flow of charged particles will be propelled in the direction of the capture electrode 133, and eventually will be trapped in the potential well created by the capture electrode 133.

Figure 14C:
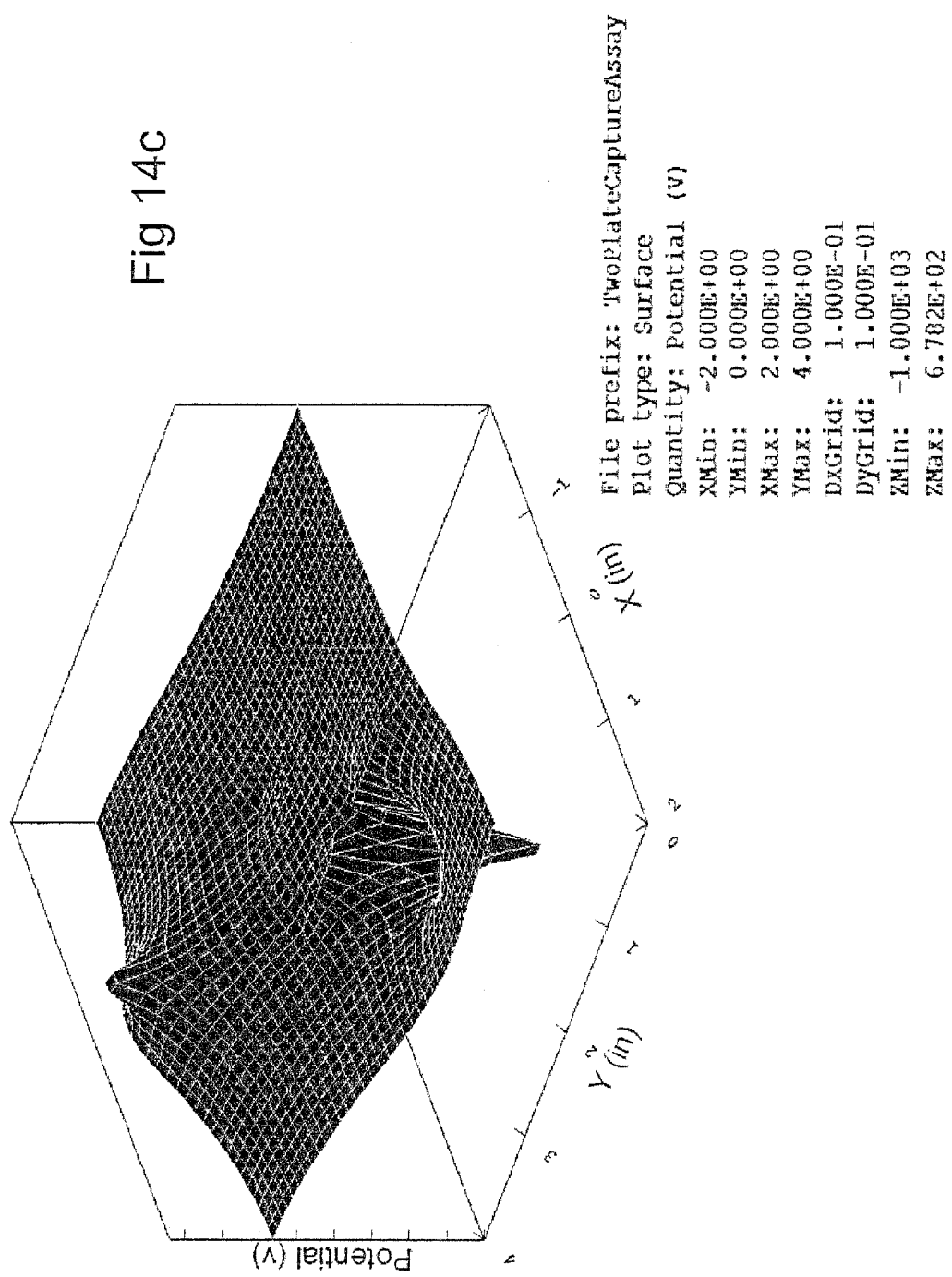
FIGS. 14a, b and c are outputs of the computer simulation of the present invention similar to FIG. 13a, b and c, but with an assay device interposed in the potential well.

For simplicity and ease of understanding, no capture means or assay device was included in FIGS. 13a, b and c. In FIGS. 14a, b and c, a representation of a capture means and/or assay device, 144, is included. This is placed between the slotted plate electrode 142 and the capture electrode 143. A dielectric constant value of 2.0 for the capture means and/or assay device is input into the computer simulation. Reference values for typical dielectric constants may be obtained from Handbook of Chemistry and Physics, CRC Press, Boca Raton, Fla., 91$^{st}$ Edition, 2010, section 13. The value 2.0 is that for dry paper. Comparing FIGS. 13a, b and c with FIGS. 14a, b and c, the presence of paper as a capture means has no significant impact on the electric field distribution.

From the same web site, polystyrene resin has dielectric constant in the range 2.4-2.6. In order to cover the span of likely materials for capture means and assay devices, a dielectric constant of 3.0 was applied to the capture means and/or assay device 154 in the computer simulation of FIG. 15a, b and c. Again, no significant perturbation of the electric field distribution results, comparing FIGS. 13a, b and c, 14a, b and c and 15a, b and c. These foregoing simulations thus show that there is great freedom in choice and disposition of capture means and assay devices in designs of the present invention.

Capture means can be placed on both sides of the capture electrode, as illustrated by 164 and 165 in FIG. 16a. As in the preceeding FIGS. 13a, b and c, 14a, b and c and 15a, b and c, there is no significant impact on the electric field distribution.

A device according to the present invention based on the prior art device of FIG. 10a, b and c is shown in FIG. 17a, b and c. This consists of a single wire electrode 170, a single planar electrode 171 and, additionally, a capture electrode 172, situated downstream of the planar electrode 171. This arrangement may be designed to capture charged particles from the fluid flow by concentrating the stream on a center line with the capture electrode centrally placed. Further, the device according to the resent invention in FIG. 18a, b and c shows the additional placing of a capture means, 183, of dielectric constant 2.0, between the planar electrode 181 and the capture electrode 182.

A preferred design according to the present invention is shown in FIGS. 19a, b and c. Here three wire electrodes 190, and three planar electrodes 191, are disposed at angles so as to maximize the fluid flow to converge on the capture electrode, 192, thus optimizing the combination of fluid flow and electrokinetically directed flow in to the potential well created by the capture electrode.

The foregoing computer simulation package is adequate to describe the prior art devices where all sections are equivalent for planes extending into a third dimension. However, it would be desirable to create devices that focus a charged particle stream in three dimensions, thus providing a true focusing effect. For this purpose, a higher level software package from Field Precision LLC is used. This package rigorously solves the same basic physical equations in three dimensional space by the same method of finite element analysis. The program is executed in three stages. The program Geometer has three-dimensional CAD features and is used for the creation of the initial design and visualization, for example, by creation of stereographic diagrams. The program Metamesh takes the output from Geometer and creates the mesh for finite element analysis, and also inputs dimensions and various electrical and physical properties of the components. Hiphi solves the equations for the files created by Metamesh and Phiview performs further optional calculations and provides for a variety of options for representing the output. Thus, the device created in Geometer is displayed in FIG. 20a, b c and d. Here, the prior art device of FIGS. 9a, b and c is provided with an additional capture electrode according to the present invention. The wire electrode 200 is 10 inches in length, the plate electrodes 201 are 10×10 inch squares and the capture electrode 202 is 0.5×0.5 inches. Plate electrodes 201 and capture electrode 202 are 0.1 inch thick. FIG. 20a is a general stereographic view showing the orientations of the x, y and z axes. FIG. 20b is a view of the device looking down the x-axis, FIG. 20c is a view of the device looking down the y-axis and FIG. 20d is a view of the device looking down the z-axis. The definition of the axes and the orientation of the parts relative to these axes is important for the understanding of FIGS. 21-23 since these represent successive planes progressing through the device along the three axes. The device according to the current invention in FIGS. 20-23 is provided with a voltage of 1000 at the wire electrode 200, 0 volts at the plate electrodes 201 and −1000 volts at the capture electrode 202. The Phiview program can represent innumerable planes along each of the three axes, but for the purposes of illustration, only those planes which lie at critical junctures in the device are represented here. Thus, FIG. 21a is in the y-z plane at the position X=−4.95

Figure 21F:
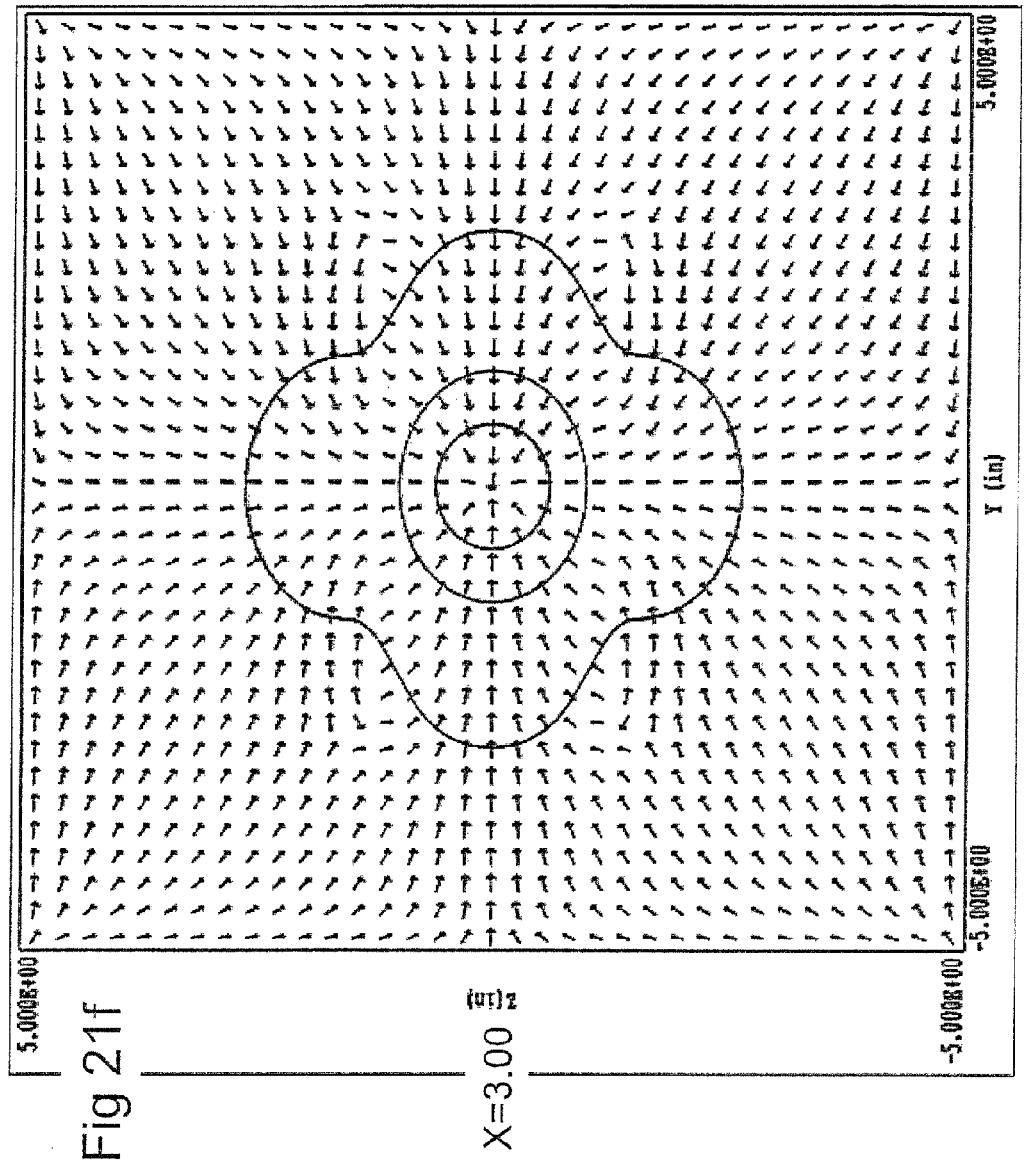
Figure 22D:
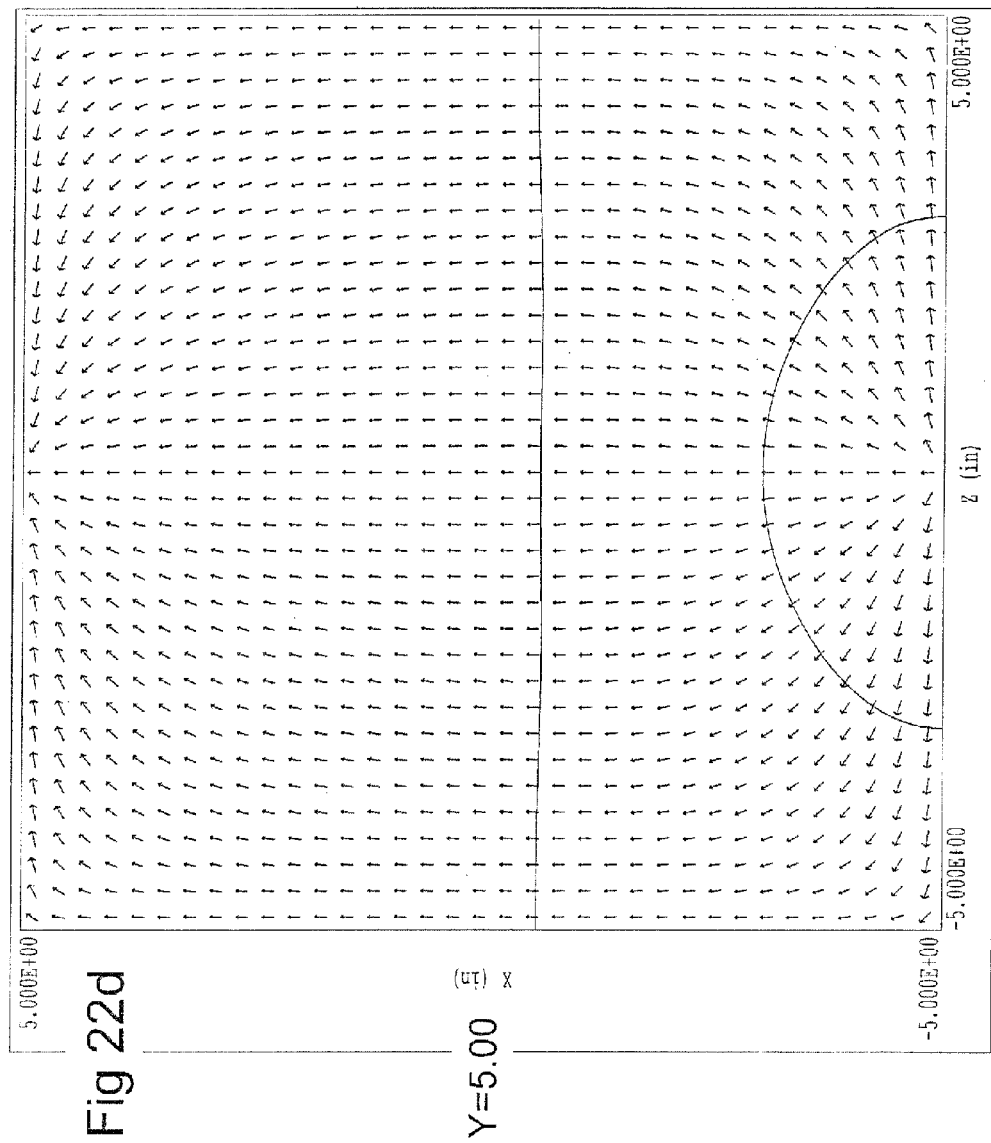

The position of the plane is indicated on the vertical axis of each figure. The contour lines of constant voltage are at approximately 100 volt intervals. The density of the contours is an indication of the field strength and hence the force applied to charged particles. The arrows are vectors representing field direction in each cell for which there has been a calculation. Thus, in FIG. 21a there is a moderate force field propelling charge particles away from the center line. Note that this is only the component of the vector in the Y-Z plane, and here, as everywhere else, the final direction is the result of vectors in all three dimensions. The successive FIGS. 21b-21h then step successively through the entire device. FIG. 21b cuts through the plane in which the wire electrode 200 lies, and shows very high field strength propagating out from the wire. Next, FIGS. 21c-e cut through orthogonally to the planar electrodes at the extremities and at the center. The field intensity is relatively low in this region, being less than 10 volts per inch, as indicated by one or less contour lines. FIG. 21f falls intermediate between the planar electrodes and shows increasing voltage gradient in the direction of the center of the section. FIG. 21g shows a section through the capture electrode and shows extremely high voltage gradient forming the potential well. Finally, the plane at x=5 inches shows moderating field strength, but continued direction of vectors to the center line. Surprisingly, any charged particles exiting the device will be swept into the center of the y-z plane, and from FIGS. 22a and 23a, back into the potential well along the X axis.

FIGS. 22a-d show successive x-z planes progressing from the origin outward along the y axis. No sections for negative values of y are shown since the device is symmetrical around the origin of the y-axis. A similar consideration holds for FIGS. 23 a-f along the z-axis.

Figure 23F:
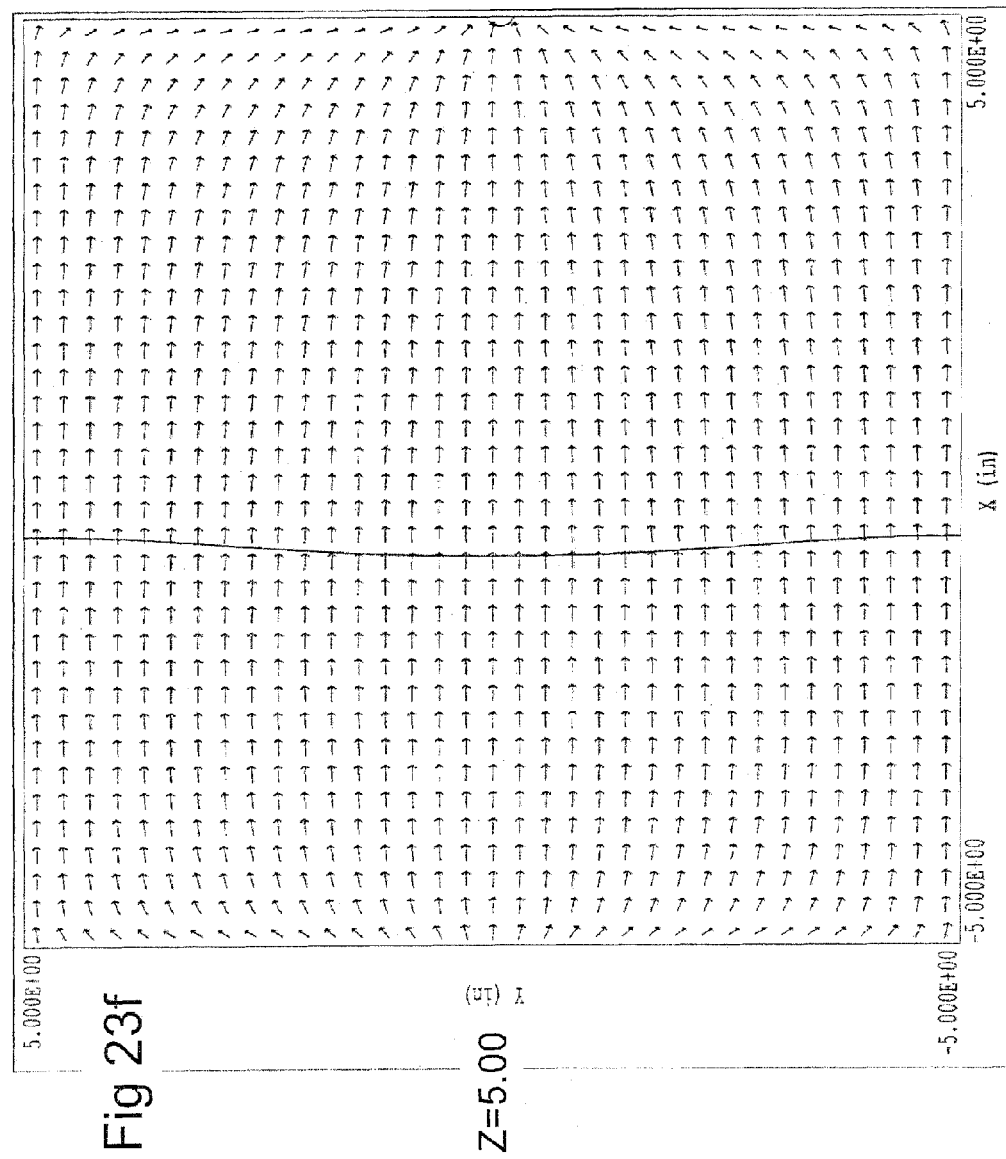
Figure 25A:
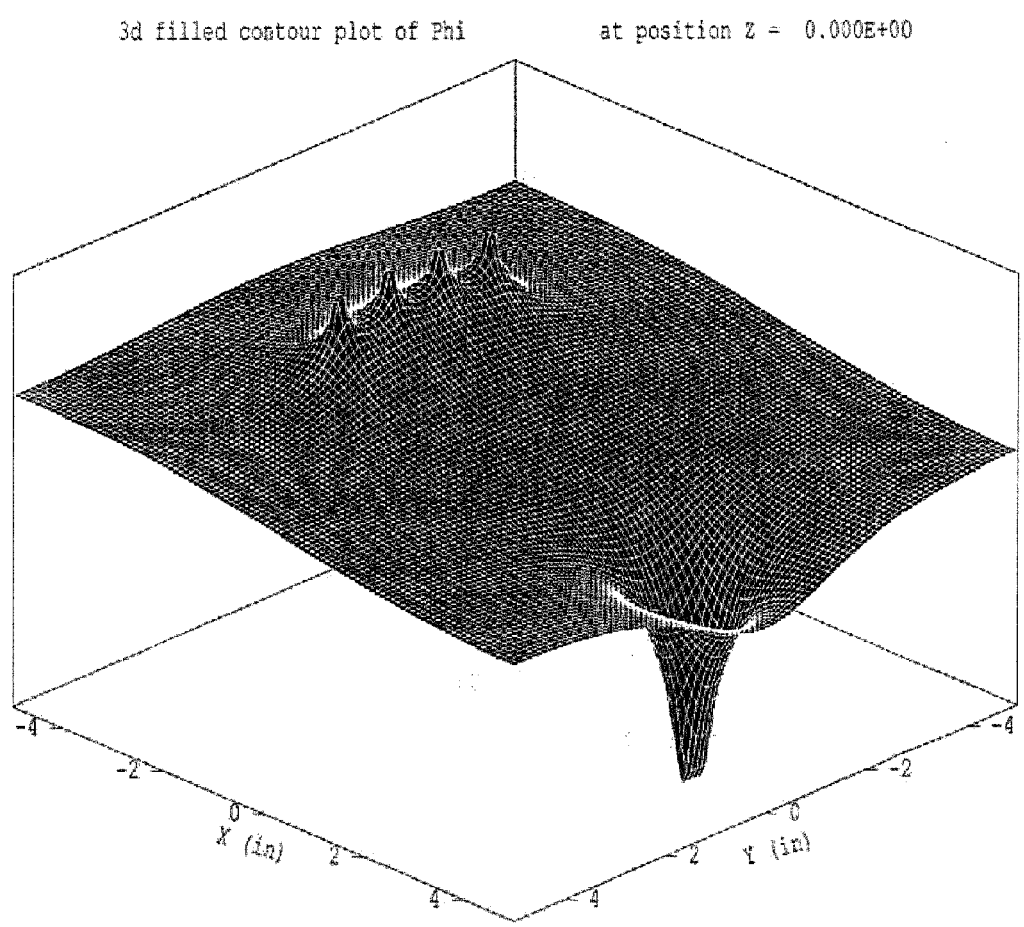
FIGS. 25a and b are electric field representations in two planes along one axis of the device of FIG. 24.
Figure 25B:
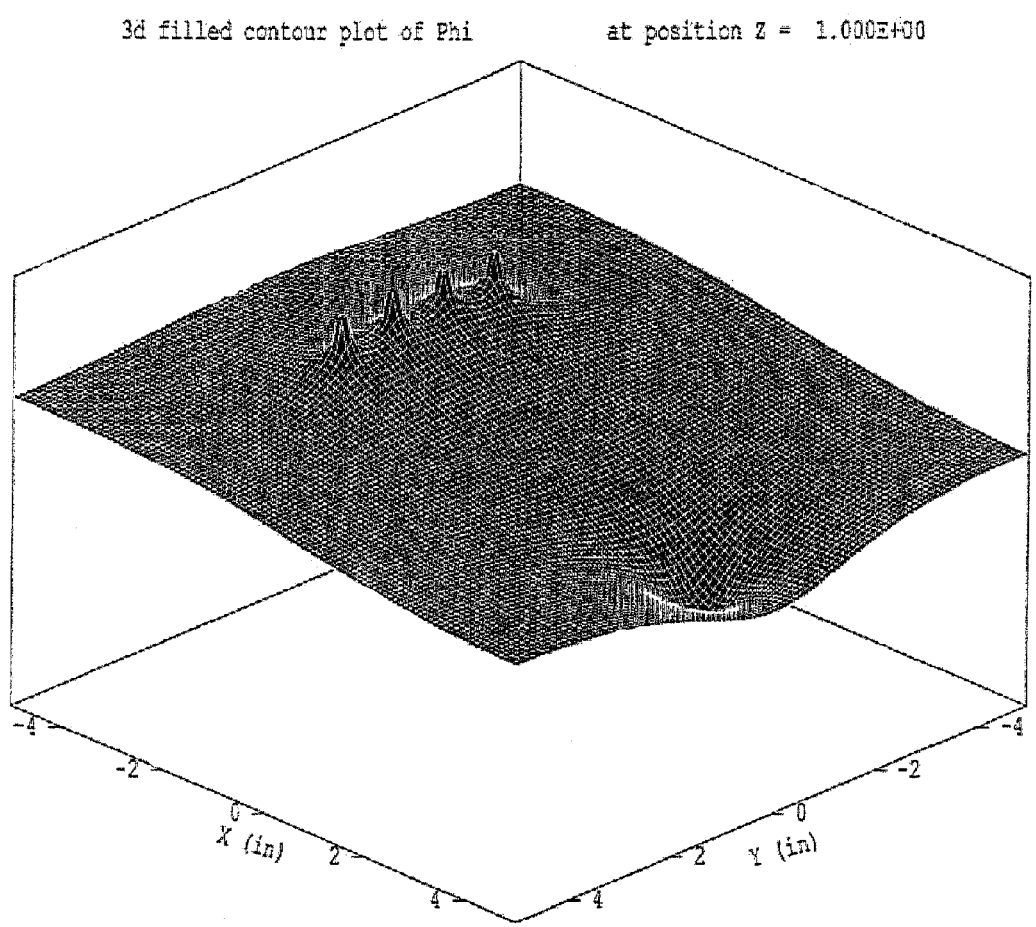

FIG. 22a confirms the findings of the two dimensional analysis software package, with the exception that out of the neighborhood of the center line of FIG. 22a, vectors direct the stream away from the plate electrodes, or downstream. Further, every section of FIG. 23 shows the x-y components of the vectors pointing downstream. Hence, the electroprecipitation on the plate electrodes will be minimal. FIG. 23a shows the section including the wire electrode in the x-y plane, and including the capture electrode. In this section, the forces propelling charged particles from the wire electrode into the potential well of the capture electrode are apparent. FIG. 23b is a section of the x-y plane just proximal to the capture electrode, and then 23c, 23d and 23e proximal to, cutting through and distal to the plate electrode, which is visible in FIG. 23d.

A further embodiment of the present invention is illustrated in stereographic projections in FIGS. 24a, b and c generated in the Geometer program. This embodiment is intended to function as a breathalyzer device for breath-borne pathogens such as *M. tuberculosis*. This can be implemented using a structure similar to FIG. 3 but eliminating the fan 36. Instead, the user blows into the entrance grill 31. The entrance grill 31 directs breathed air flow in the enclosure. FIG. 24*a* represents a general perspective view of the electrode arrangement, showing all three X, Y and Z axes. FIG. 24*b* is a view looking down the Y-axis, FIG. 24*c* is a view looking down the X-axis and FIG. 24*d* is a view looking down the Z-axis. The FIG. 24 shows only the arrangement of the electrodes, and, for ease of understanding, the supporting structures which are made of materials in a range of dielectric constants that do not influence the electric field, are omitted. The device includes 4 wire electrodes for generating plasma and two capture electrodes which may be used for collection means for two different assay types. Thus, capture electrode 241 may be used for an optical sensor device utilizing an immunoassay, as described in detail in U.S. Pat. No. 7,384,793, while capture electrode 242 may be used as a capture device for the nucleic acid amplification based system Xpert MTB/RIF as described in Blakemore et al (2010) in Journal of Clinical Microbiology, volume 48, pages 2495-2501, Helb et al (2010) in Journal of Clinical Microbiology, volume 48, pages 229-237, and references therein. The performance of this embodiment is processed with MetaMesh and results generated with HiPhi. FIGS. 25*a* and *b* represent two views created from PhiView. These two views selected from the complete three dimensional analysis are sufficiently representative to demonstrate the performance. FIG. 25*a* is a pseudo-3D contour plot showing the electric field distribution in an X-Y plane intersecting the origin of the Z-axis. The Z-axis is not a physical Z-axis but represents the range 0-1000 volts. It can be seen from FIGS. 24*a, b, c* and *d* that this plane will intersect all four wire electrodes and midway between the two capture electrodes. It thus shows the formation of potential peaks at the wire electrodes for the generation of plasma and a potential well in the neighborhood of the capture electrodes, which will serve to capture and electroprecipitate charged particles. A further contour plot in FIG. 25*b* is the voltage distribution in a parallel plane displaced 1 inch out on the physical Z-axis. This plane skirts the extremity of the wire electrodes, which are 2 inches in length. Here, too, can be seen the potential peaks at the wire electrodes and the residual potential well that is here 0.5 inches beyond the extremity of the capture electrode. The ability to incorporate two capture electrodes in this case enhances the sensitivity of the assay by providing for two entirely different assay systems for the same analyte. A further improvement is for the electrode 242 to be replaced by a wire mesh of the same dimensions. A wire mesh electrode has the advantage of creating even greater localized voltage gradients in close proximity to the wires, and thus enhance the capture effect. Following sample collection, the wire mesh electrode is removed, immersed in 2 ml of the NaOH-isopropanol sample treatment reagent, shaken for 5 seconds, incubated at room temperature for 15 minutes, shaken again, and transferred to the Xpert MTB/RIF cartridge and subject to the standard procedure for that assay device. The NaOH-isopropanol reagent is provided by Cepheid Inc, the manufacturer of the Xpert MTB/RIF assay device.

Further multiplex capability can be attained by the use of a multiplicity of capture electrodes. While FIGS. 24a, b and c and 25a, b and c show the disposition of electrodes in the breathalyzer device, further details of mouthpiece, housing, and interface with an assay device are described in the specifications of U.S. Pat. No. 7,384,793 as well as collection means and assay device commercialized by Rapid Biosensor Systems Limited, Babraham, Cambridge, UK. A tubular or elliptical section housing can be constructed to accommodate the mouthpiece, with entrance diameter optimized to match the dimensions of the wire electrodes and the exit diameter optimized to match the dimensions of the capture electrodes. The breath will then have maximum contact with wire electrodes, and exit flow can be concentrated over the capture electrodes.

It is apparent that the software packages provided by Field Precision LLC are useful for achieving optimal designs without undue experimentation. Such programs have been under development for several years. P. L. Levin et al ("A Unified Boundary-element Finite-element Package" in IEEETransactions on Electrical Insulation 1993, volume 28, pages 161-167) made such a package available. Examples of application of such software packages for the design of electrostatic precipitation devices are given by S. Vlad ("Numerical Computation of Conducting Particle Trajectories in Plate-type Electrostatic Separators" in IEEE Transactions on Industry Applications 2003, volume 39, pages 66-71) and by A. Bendoaoud et al ("Experimental Study of Corona Discharge Generated in a Modified Wire-plate Electrode Configuration for Electrostatic Process Applications" in IEEE Transactions on Industry Applications 2010, volume 46, pages 666-671). Optimization of the designs of the present invention is not limited to the software packages provided by Field Precision LLC.

A key element of the present invention is the provision of a potential well that will act as a trap for charged particles of interest in a flowing fluid stream. It is possible to design innumerable devices within the scope of this invention, and the configuration shown in the illustrations of this document are intended to be exemplary only. It is surprising that creation of a potential well provides a universal and efficient trap for charged particles and provides for seamless transfer on to a measuring or detection device. The sensitivity of the measurement of the detection or detection device is considerably enhanced by the ability to sample large volumes of fluid and to concentrate the charged particles on to a small area of a detection device. Because the properties, disposition and dimensions of non-conducting materials do not significantly affect the voltage field distribution, there are unlimited possibilities for the design and fabrication of devices for practical applications, using, for example any of a wide range of plastic or polymeric non-conducting materials.

In the devices described in the foregoing, the area of the capture electrode is small compared with other electrodes in the system, thus providing a large voltage gradient. In the examples, typical ratios of areas of capture electrodes are 20:1. Depending on the construction of the specific device, this ratio may vary in the range 5:1 to 1000:1 or even greater, limited only by the performance requirements of the specific system. The capture electrode is usually in the form of a rectangular plate, but may also take the form of a metal grid or mesh. In the case of a multiplicity of wire electrodes for generating plasma, these are usually arrayed as parallel wires, but may also be arranged as a rectangular grid, depending on the requirements or constraints of a specific design. The only constraint is that the geometry of the capture electrode may not be such as to create a potential well with gradient so steep as to initiate plasma generation, and generate charged particles that will be launched out of the potential well.

On the contrary, the wire electrodes must be of dimensions small enough that they will create a potential gradient sufficient to cause the generation of plasma. The wire electrodes advantageously do not exceed 1.0 mm in diameter and in one embodiment may have a diameter of approximately 0.1 mm. However, the geometry of the wires may be varied and may also take the form of spikes with pointed tips. In this case, the pointed tip may give rise to a local potential gradient high enough to give rise to the formation of charged plasma.

The voltages applied must be sufficiently large to create the conditions for the functioning of the invention, but voltages can be varied to optimize the performance. The voltage values may be positive or negative at either the wire electrodes or the capture electrodes. For functioning, only relative voltages are important, so that any electrode may also be set at ground or low voltage, for example, for safety reasons.

For reduction to practice, the devices of the current invention can be fabricated from simple modifications of existing devices. Thus, all the specifications for details of hardware, electronic control, aesthetic considerations, dimensions, portability, power supply from ac mains or battery, are all described in detail in the prior art references given in this document, and so need no further elaboration here.

Further applications to capture of entities to be assayed in dielectric media other than air can be created using the same principles as enunciated throughout this document. The dielectric fluid medium may further include non-conductive liquids, such as oils. Oils may be sampled for the presence of contaminants, contaminating organisms or bio-degrading organisms.

What we claim is:

1. A device for collection of a sample from a dielectric fluid medium for a bio-specific assay device, comprising:
    an enclosure;
    flow means for directing fluid flow of said dielectric fluid medium in said enclosure;
    one or more wire electrodes in said enclosure to subject dielectric fluid medium flowing in said enclosure to an ionizing plasma;
    supporting means operatively associated with said enclosure for supporting the bio-specific assay device; and
    one or more capture electrodes positioned proximate said supporting means to create a voltage potential well whereby charged particles thus generated within said dielectric fluid medium, or pre-existing in said dielectric fluid medium, are propelled into the supported bio-specific assay device thereby electroprecipitating said charged particles on to a sample collection region of said bio-specific assay device.

2. The device according to claim 1 wherein the dielectric fluid is air and the flow means directs air flow.

3. The device according to claim 1 wherein the dielectric fluid is a non-conducting liquid and the flow means directs liquid flow.

4. The device according to claim 1 wherein substantially planar electrodes are provided in the enclosure to effect electrokinetic flow of said dielectric fluid medium.

5. The device according to claim 1 wherein the flow means comprises a pump.

6. The device according to claim 1 wherein the flow means comprises a fan.

7. The device according to claim 2 wherein the flow means is adapted to be breathed in by a user.

8. The device according to claim 1 wherein the wire electrodes are approximately 0.1 mm diameter.

9. The device according to claim 1 wherein the wire electrodes do not exceed 1 mm in diameter.

10. The device according to claim 1 wherein the sum of the longest dimensions of the capture electrodes does not exceed one fifth of the sum of the length of the wire electrodes.

11. The device according to claim 1 wherein the assay device comprises a lateral flow assay device.

12. The device according to claim 1 wherein the assay device comprises an immunosensor based assay device.

13. The device according to claim 1 wherein the assay device comprises an enzyme immunoassay device.

14. The device according to claim 1 wherein the assay device comprises a nucleic acid hybridization assay device.

15. The device according to claim 14 wherein the nucleic acid hybridization assay device comprises a polymerase chain reaction nucleic acid sequence amplification process.

16. The device according to claim 2 wherein the assay device monitors the air in an enclosed space of the enclosure.

17. The device according to claim 1 wherein the supporting means comprises a sample collection device that is continuously moved relative to the voltage potential well to provide a time record of the presence or amount of the species determined by the assay device.

* * * * *

UNITED STATES PATENT AND TRADEMARK OFFICE
CERTIFICATE OF CORRECTION

| | | |
|---|---|---|
| PATENT NO. | : 8,038,944 B1 | Page 1 of 1 |
| APPLICATION NO. | : 13/028495 | |
| DATED | : October 18, 2011 | |
| INVENTOR(S) | : Julian Gordon et al. | |

It is certified that error appears in the above-identified patent and that said Letters Patent is hereby corrected as shown below:

In the Claims

Column 15, Line 12-13, Claim 7 - should read

-- 7. The device according to claim 2 wherein the flow means is adapted to be breathed into by a user. --

Signed and Sealed this
Thirteenth Day of May, 2014

Michelle K. Lee
*Deputy Director of the United States Patent and Trademark Office*